(12) United States Patent
Adachi et al.

(10) Patent No.: US 12,077,546 B2
(45) Date of Patent: Sep. 3, 2024

(54) BICYCLIC PYRIDINE DERIVATIVE

(71) Applicant: Sumitomo Pharma Co., Ltd., Osaka (JP)

(72) Inventors: Satoshi Adachi, Osaka (JP); Hidefumi Yoshinaga, Osaka (JP); Hajime Shibata, Osaka (JP); Yusuke Shioda, Osaka (JP); Riko Nagahama, Osaka (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 18/506,804

(22) Filed: Nov. 10, 2023

(65) Prior Publication Data

US 2024/0150370 A1   May 9, 2024

Related U.S. Application Data

(63) Continuation of application No. 18/554,525, filed as application No. PCT/JP2022/017396 on Apr. 8, 2022.

(30) Foreign Application Priority Data

Apr. 10, 2021 (JP) ................. 2021-066825
Sep. 15, 2021 (JP) ................. 2021-150394

(51) Int. Cl.
| | |
|---|---|
| C07D 471/04 | (2006.01) |
| A61P 25/00 | (2006.01) |
| C07D 213/65 | (2006.01) |
| C07D 215/12 | (2006.01) |
| C07D 221/04 | (2006.01) |
| C07D 401/06 | (2006.01) |
| C07D 491/048 | (2006.01) |
| C07D 495/04 | (2006.01) |

(52) U.S. Cl.
CPC .......... C07D 491/048 (2013.01); A61P 25/00 (2018.01); C07D 213/65 (2013.01); C07D 215/12 (2013.01); C07D 221/04 (2013.01); C07D 401/06 (2013.01); C07D 471/04 (2013.01); C07D 495/04 (2013.01)

(58) Field of Classification Search
CPC .................................... C07D 491/48
USPC ........................................ 514/302
See application file for complete search history.

(56) References Cited

FOREIGN PATENT DOCUMENTS

| ES | 2131020 A1 | 7/1999 |
|---|---|---|
| JP | 2003-524620 A | 8/2003 |
| JP | 2013-512926 A | 4/2013 |
| JP | 2019-525939 A | 9/2019 |
| WO | WO 00/056729 | 9/2000 |
| WO | WO 2011/069063 A2 | 6/2011 |
| WO | WO 2016/130796 A1 | 8/2016 |
| WO | WO 2018/023072 A2 | 2/2018 |
| WO | WO 2018/151861 A1 | 8/2018 |
| WO | WO 2019/028165 A1 | 2/2019 |
| WO | 2018078360 * | 2/2020 |
| WO | WO 2022/204150 A1 | 9/2022 |

(Continued)

OTHER PUBLICATIONS

International Search Report issued Jun. 28, 2022 in PCT/JP2022/017396 filed Apr. 8, 2022, 9 pages.
Database Registry Dec. 1, 2017 (Dec. 1, 2017), Anonymous : "—Cyclobutanamine, 1-(6,7-dihydro-5H-cyclopenta[b]pyridin-7-yl)—(CA Index Name)", XP055975824, retrieved from STN Database accession No. 2149426-89-9XP; XP055975824.
Database Registry Dec. 11, 2017 (Dec. 11, 2017), Anonymous : "—Cyclobutanamine, 1-(5,6,7,8-tetrahydro-8-quinolinyl)—(CA Index Name) ", XP055975821, retrieved from STN Database accession No. 2155575-38-3XP; XP055975821.
Beattie Doreen E, et al.: "5,6,7,8-Tetrahydroquinolines. 5. Antiulcer and antisecretory activity of 5,6,7,8-tetrahydroquinolinethioureas and related heterocycles", Journal of Medicinal Chemistry, American Chemical Society, US, vol. 20, No. 5, Jan. 1, 1977 (Jan. 1, 1977), US , pp. 718-721, XP002969401, ISSN: 0022-2623, DOI:10.1021/jm00215a020XP; XP002969401.

(Continued)

*Primary Examiner* — Niloofar Rahmani
(74) *Attorney, Agent, or Firm* — Oblon, McClelland, Maier & Neustadt, L.L.P.

(57) ABSTRACT

The present disclosure provides bicyclic pyridine derivatives.
A compound represented by formula I:

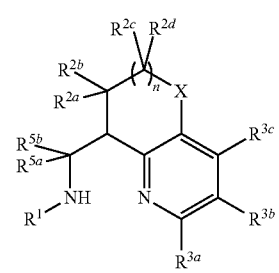

or a pharmaceutically acceptable salt thereof,
wherein
X is a oxygen atom, sulfur atom, NR, or CR'R", n is 0 or 1, $R^1$, $R^{2a}$, $R^{2b}$, $R^{2c}$, $R^{2d}$, R, R' and R" are each independently a hydrogen atom, a halogen atom, optionally substituted $C_{1-6}$ alkyl, or an optionally substituted $C_{6-10}$ aryl, or two of $R^{2a}$, $R^{2b}$, $R^{2c}$, $R^{2d}$, R, R', and R", together with a carbon atom or a nitrogen atom to which they are attached, form a 3- to 6-membered saturated carbocyclic ring or saturated heterocyclic ring, and $R^{3a}$, $R^{3b}$, $R^{3c}$ and $R^{5a}$ and $R^{5b}$, are as defined in the description.

25 Claims, 2 Drawing Sheets

(56) References Cited

FOREIGN PATENT DOCUMENTS

WO    WO 2022/217232 A1    10/2022
WO    WO 2022/217265 A1    10/2022

OTHER PUBLICATIONS

Dedic Nina, Dworak Heather, Zeni Courtney, Rutigliano Grazia, Howes Oliver D.: "Therapeutic Potential of TAAR1 Agonists in Schizophrenia: Evidence from Preclinical Models and Clinical Studies", International Journal of Molecular Sciences, vol. 22, No. 24, pp. 13185, XP055975819, DOI: 10.3390/ijms222413185 XP; XP055975819.
B Joseph et al., Heterocycles vol. 41 No. 12 p. 2769 1995.
"SciFinder RN search result", Search Results by the applicant, Oct. 27, 2023.

\* cited by examiner

[Fig.1]
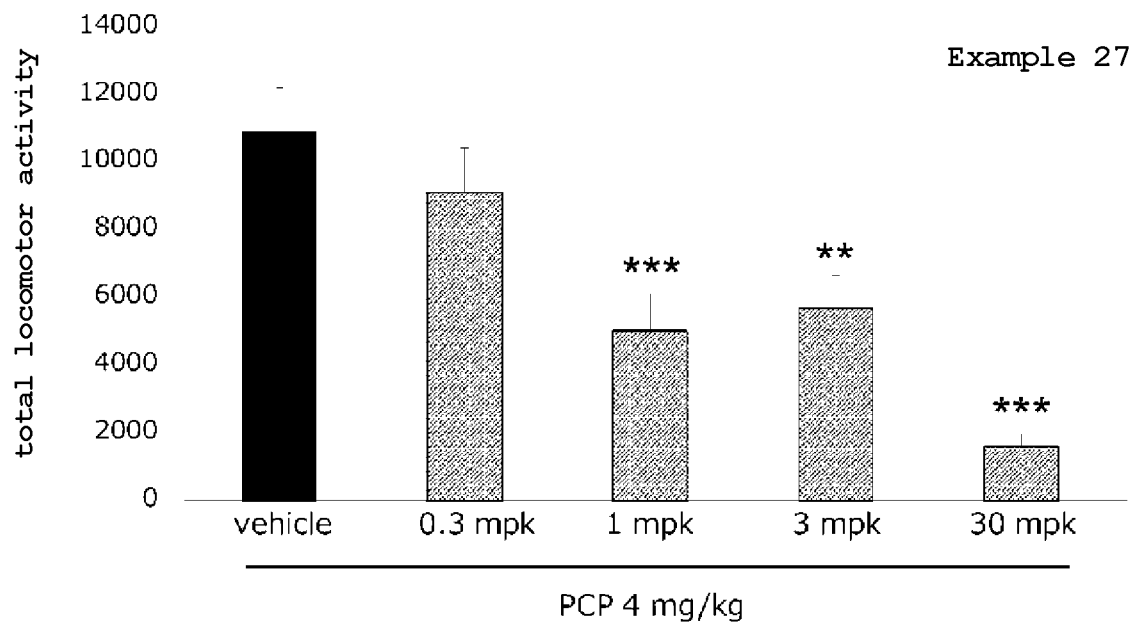
[Fig.2]
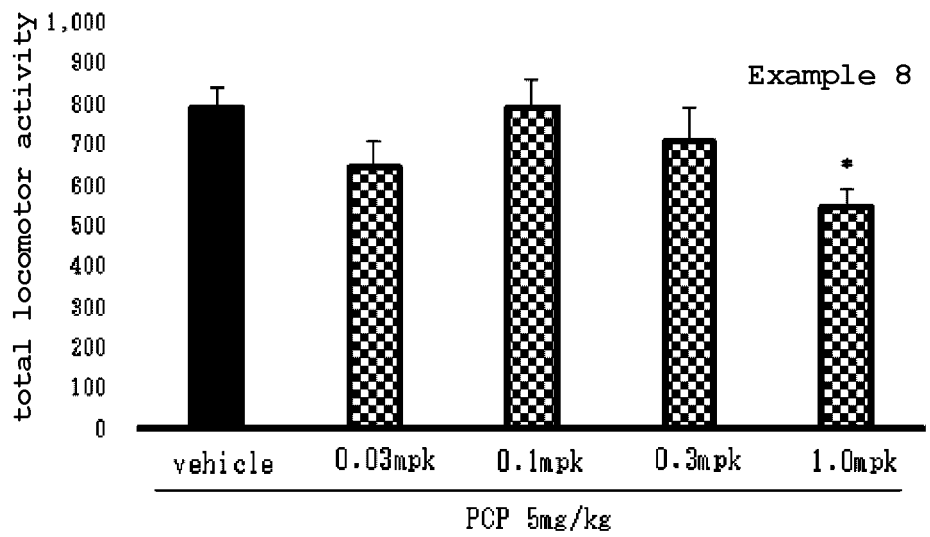

[Fig.3]
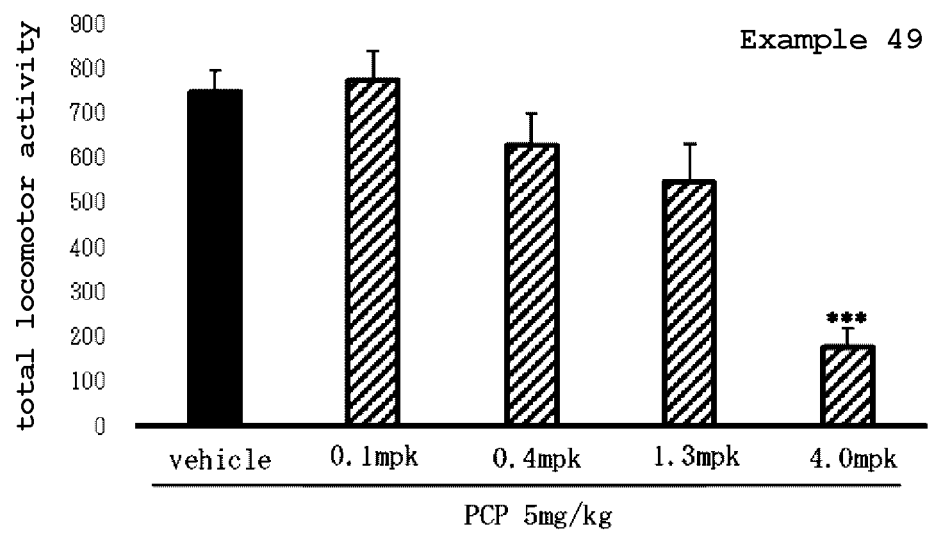

BICYCLIC PYRIDINE DERIVATIVE

CROSS-REFERENCE TO RELATED APPLICATIONS

The present application is a continuation of U.S. application Ser. No. 18/554,525, filed Oct. 9, 2023, which is a 35 U.S.C. § 371 national stage patent application of International Patent Application No. PCT/JP2022/017396, filed on Apr. 8, 2022, which is based on and claims the benefits of priority to Japanese Application No. 2021-066825, filed on Apr. 10, 2021 and Japanese Application No. 2021-150394, filed on Sep. 15, 2021. The entire contents of all the above applications are incorporated herein by reference.

TECHNICAL FIELD

The present disclosure relates to a bicyclic pyridine derivative having agonist activity on a trace amine-associated receptor TAAR1 receptor, or a pharmaceutically acceptable salt thereof, and a therapeutic agent for neuropsychiatric disorders containing the derivative as an active ingredient.

BACKGROUND ART

Trace amines (TA), which are a type of biogenic amines, include p-tyramine, β-phenylethylamine, tryptamine, and octopamine. Although its structure and metabolism are similar to those of classical biogenic amines typically including serotonin, dopamine, and norepinephrine, they exist only in very small amounts under the physiological conditions of the living body (Non-Patent Document 1). TA is known to play an important role in regulating nerve transmission in the central and peripheral nervous systems. Dysregulation of TA has been suggested to be involved in various central nervous system diseases including schizophrenia, mood disorders, attention deficit hyperactivity disorder, Parkinson's disease, migraine, and eating disorders, and it is expected that improving the dysregulation lead to the establishment of new disease treatment methods (Non-Patent Document 2).

Nine genes have been reported in TA receptors in humans. The TAAR1 receptor is a G protein-coupled receptor and is activated through Gαs using TA as a ligand. It has also been reported that other amines, catecholamine metabolites, dopamine agonists and the like act as ligands (Non-Patent Documents 1 and 3). It is known that downstream signals suppress dopamine uptake and promote dopamine release in a PKC-dependent manner by phosphorylating dopamine transporters via cAMP-PKA/PKC (Non-patent Document 4, 5). In the central nervous system, the TAAR1 receptor is expressed in the monoaminergic nuclei of origins including the ventral tegmental area and the raphe nucleus, as well as the limbic system, and also regulates glutamate neurotransmission and serotonin neurotransmission, thus, it is suggested that the TAAR1 receptor may act on various monoamine functions (Non-Patent Document 1).

6q23, the gene locus encoding TAAR1, is a region associated with multiple psychiatric diseases, and monoaminergic neurotransmission regulated by TAAR1 shows a strong relationship with neuropsychiatric disorders, hence, it is expected that TAAR1 receptor selective ligands will be effective in treating these diseases. In addition, low-molecular-weight compounds which exhibit TAAR1 receptor agonism that have been reported to date have shown antipsychotic and antidepressant effects in multiple disease models using rodents, and exhibited cognitive function-improving effects also in evaluation using non-human primates, thus, can be expected to have antipsychotic, antidepressant, and cognitive function-improving effects in humans as well (non-clinical literature 6).

DOCUMENT LIST

Non-Patent Document

[Non-Patent Document 1] Beth Borowsky et. al., Proc Natl Acad Sci USA. 98, 8966-8971, 2001
[Non-Patent Document 2] Branchek, T. A. and Blackburn, T. P. et. al., Curr. Opin. Pharmacol. 3, 90-97, 2003
[Non-Patent Document 3] James R. Bunzow et. al., Mol Pharmacol. 60, 1181-1188, 2001
[Non-Patent Document 4] Zhihua Xie and Gregory M. Miller et. al., Journal of Pharmacology and Experimental Therapeutics 321, 128-136, 2007
[Non-Patent Document 5] Zhihua Xie and Gregory M. Miller et. al., Journal of Pharmacology and Experimental Therapeutics, 330, 316-325, 2009
[Non-Patent Document 6] F G Revel et. al., Molecular Psychiatry, 18, 543-556, 2013

SUMMARY OF THE INVENTION

Means for Solving the Problem

The present disclosure provides novel compounds that have agonist activity on the trace amine-associated receptor TAAR1 receptor and are useful as therapeutic agents for neuropsychiatric disorders.

The present inventors have found that a compound represented by the following formula I or a pharmaceutically acceptable salt thereof (hereinafter sometimes referred to as "the disclosed compound") has agonist activity on the trace amine-associated receptor TAAR1 receptor, providing the present disclosure.

Accordingly, the present disclosure is, for example, as follows.

[Item 1]
A compound represented by formula I

[Chemical Formula 1]

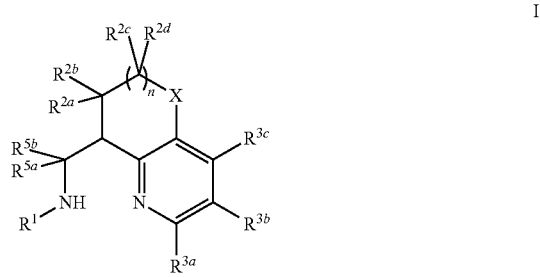

or a pharmaceutically acceptable salt thereof,
wherein
X is an oxygen atom, a sulfur atom, NR, or CR'R",
n is 0 or 1,
$R^1$ is a hydrogen atom, optionally substituted $C_{1-6}$ alkyl, or optionally substituted $C_{3-6}$ alkenyl,
$R^{2a}$, $R^{2b}$, $R^{2c}$, $R^{2d}$, R, R', and R" are each independently a hydrogen atom, a halogen atom, optionally substituted $C_{1-6}$ alkyl, or optionally substituted $C_{6-10}$ aryl, or two of $R^{2a}$, $R^{2b}$, $R^{2c}$, $R^{2d}$, R, R', and R", together with a carbon atom or a nitrogen atom to which they are attached, form a 3- to 6-membered saturated carbocyclic ring or saturated heterocyclic ring, $R^{3a}$, $R^{3b}$, and $R^{3c}$ are each independently a hydrogen atom, optionally substituted $C_{1-6}$ alkyl, a halogen atom, —$OR^4$, or optionally substituted $C_{6-10}$ aryl, $R^4$ is optionally substituted $C_{1-6}$ alkyl or optionally substituted 3- to 6-membered saturated carbocyclic ring, and $R^{5a}$ and $R^{5b}$ are each independently a hydrogen atom or optionally substituted $C_{1-6}$ alkyl, or $R^{5a}$ and $R^{5b}$, together with a carbon atom to which they are attached, form a 3- to 6-membered saturated carbocyclic ring, wherein, the optionally substituted $C_{1-6}$ alkyl and optionally substituted $C_{3-6}$ alkenyl are optionally substituted with a halogen atom, hydroxy, or $C_{1-6}$ alkoxy, and the optionally substituted $C_{6-10}$ aryl and optionally substituted 3- to 6-membered saturated carbocyclic ring are optionally substituted with a halogen atom, hydroxy, $C_{1-6}$ alkyl, or $C_{1-6}$ alkoxy, provided that the following (1) to (19) are excluded:

(1) a compound wherein n is 0, X is an oxygen atom, and $R^{2a}$ and $R^{2b}$ are hydrogen atoms;

(2) a compound wherein n is 1, X is an oxygen atom, and $R^{2a}$, $R^{2b}$, $R^{2c}$, $R^{2d}$, $R^{3a}$, $R^{3b}$, and $R^{3c}$ are hydrogen atoms;

(3) a compound wherein n is 1, X is $CH_2$, $R^1$, $R^{2a}$, $R^{2b}$, $R^{2c}$, $R^{2d}$, $R^{3b}$, $R^{3c}$, $R^{5a}$, and $R^{5b}$ are hydrogen atoms, and $R^{3a}$ is a hydrogen atom or $CH_3$;

(4) a compound wherein n is 1, X is an oxygen atom, $R^1$, $R^{2a}$, $R^{2b}$, $R^{2c}$, $R^{2d}$, $R^{3b}$, $R^{3c}$, $R^{5a}$, and $R^{5b}$ are hydrogen atoms, and $R^{3a}$ is $CH_3$;

(5) a compound wherein n is 1, X is an oxygen atom, R', $R^{2a}$, $R^{2b}$, $R^{3a}$, $R^{3b}$, $R^{3c}$, $R^{5a}$, and $R^{5b}$ are hydrogen atoms, and $R^{2c}$ and $R^{2d}$ are $CH_3$;

(6) a compound wherein n is 1, X is an oxygen atom, $R^1$, $R^{2a}$, $R^{2b}$, $R^{2c}$, $R^{2d}$, $R^{3a}$, $R^{3c}$, $R^{5a}$, and $R^{5b}$ are hydrogen atoms, and $R^{3b}$ is $CH_3$;

(7) a compound wherein n is 1, X is an oxygen atom, $R^1$, $R^{2a}$, $R^{2b}$, $R^{2d}$, $R^{3a}$, $R^{3b}$, $R^{3c}$, $R^{5a}$, and $R^{5b}$ are hydrogen atoms, and $R^{2c}$ is $CH_3$;

(8) a compound wherein n is 0, X is $CH_2$, $R^1$, $R^{2a}$, $R^{2b}$, $R^{3b}$, $R^{3c}$, $R^{5a}$, and $R^{5b}$ are hydrogen atoms, and $R^{3a}$ is $CH_3$;

(9) a compound wherein n is 1, X is $CH_2$, $R^1$, $R^{2a}$, $R^{2b}$, $R^{2d}$, $R^{3a}$, $R^{3b}$, $R^{3c}$, $R^{5a}$, and $R^{5b}$ are hydrogen atoms, and $R^{2c}$ is $CH_3$;

(10) a compound wherein n is 1, X is $CH_2$, $R^1$, $R^{2a}$, $R^{2b}$, $R^{2c}$, $R^{2d}$, $R^{3a}$, $R^{3c}$, $R^{5a}$, and $R^{5b}$ are hydrogen atoms, and $R^{3b}$ is $CH_3$ and a bromine atom;

(11) a compound wherein n is 1, X is an oxygen atom, R', $R^{2a}$, $R^{2b}$, $R^{3a}$, $R^{3b}$, $R^{3c}$, $R^{5a}$, and $R^{5b}$ are hydrogen atoms, and $R^{2c}$ and $R^{2d}$, together with a carbon atom to which they are attached, form a cyclobutyl ring;

(12) a compound wherein n is 1, X is an oxygen atom, $R^{2a}$, $R^{2b}$, $R^{2c}$, $R^{2d}$, $R^{3a}$, $R^{3b}$, $R^{3c}$, $R^{5a}$, and $R^{5b}$ are hydrogen atoms, and $R^1$ is $CH_3$;

(13) a compound wherein n is 0, X is $CH_2$, $R^{2a}$, $R^{2b}$, $R^{3a}$, $R^{3b}$, $R^{3c}$, $R^{5a}$, and $R^{5b}$ are hydrogen atoms, and $R^1$ is a hydrogen atom, optionally substituted $C_{1-6}$ alkyl, or optionally substituted $C_{3-6}$ alkenyl;

(14) a compound wherein n is 1, X is $CH_2$, $R^{2a}$, $R^{2b}$, $R^{2c}$, $R^{2d}$, $R^{3a}$, $R^{3b}$, $R^{3c}$, $R^{5a}$, and $R^{5b}$ are hydrogen atoms, and $R^1$ is a hydrogen atom, optionally substituted $C_{1-6}$ alkyl, or optionally substituted $C_{3-6}$ alkenyl;

(15) a compound wherein n is 0, X is $CH_2$, $R^{2a}$, $R^{3a}$, $R^{3b}$, $R^{3c}$, $R^{5a}$, and $R^{5b}$ are hydrogen atoms, $R^{2b}$ is a hydrogen atom and $CH_3$, and $R^1$ is a hydrogen atom and $CH_3$;

(16) a compound wherein n is 1, X is $CH_2$, $R^{2c}$, $R^{2d}$, $R^{3a}$, $R^{3b}$, $R^{3c}$, $R^{5a}$, and $R^{5b}$ are hydrogen atoms, $R^{2a}$ and/or $R^{2b}$ is $CH_3$, and $R^1$ is a hydrogen atom and $CH_3$;

(17) a compound wherein n is 1, X is $CH_2$, $R^{2c}$, $R^{2d}$, $R^{3a}$, $R^{3b}$, $R^{3c}$, $R^{5a}$, and $R^{5b}$ are hydrogen atoms, $R^{2a}$ and $R^{2b}$, together with a carbon atom, form cyclopropane, and $R^1$ is a hydrogen atom and $CH_3$;

(18) a compound wherein n is 0 or 1, X is $CH_2$, and $R^{5a}$ or $R^{5b}$ is optionally substituted $C_{1-6}$ alkyl; and

(19) a compound wherein n is 0, X is $CH_2$, $R^1$, $R^{2a}$, $R^{2b}$, $R^{3a}$, $R^{3c}$, $R^{5a}$, and $R^{5b}$ are hydrogen atoms, and $R^{3b}$ is a bromine atom.

[Item 2]

The compound or the pharmaceutically acceptable salt thereof of item 1, represented by the following formula:

[Chemical Formula 2]

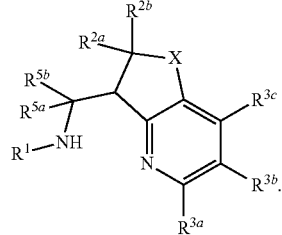

[Item 3]

The compound or the pharmaceutically acceptable salt thereof of item 1, represented by the following formula:

[Chemical Formula 3]

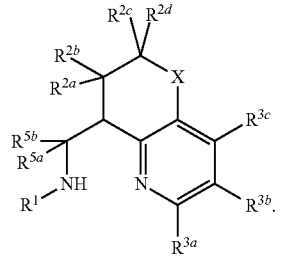

[Item 4]

The compound or the pharmaceutically acceptable salt thereof of any one of items 1 to 3, wherein $R^1$ is a hydrogen atom.

[Item 5]

The compound or the pharmaceutically acceptable salt thereof of any one of items 1 to 3, wherein $R^1$ is $C_{1-6}$ alkyl optionally substituted with a halogen atom.

[Item 6]

The compound or the pharmaceutically acceptable salt thereof of item 5, wherein $R^1$ is methyl.

[Item 7]

The compound or the pharmaceutically acceptable salt thereof of any one of items 1 to 6, wherein $R^{2a}$ and $R^{2b}$ are hydrogen atoms.

[Item 8]
The compound or the pharmaceutically acceptable salt thereof of any one of items 1 to 6, wherein $R^{2a}$ is a hydrogen atom, and $R^{2b}$ is optionally substituted $C_{1-6}$ alkyl.

[Item 9]
The compound or the pharmaceutically acceptable salt thereof of any one of items 1 to 6, wherein $R^{2a}$ and $R^{2b}$ are optionally substituted $C_{1-6}$ alkyl.

[Item 10]
The compound or the pharmaceutically acceptable salt thereof of any one of items 1 to 6, wherein $R^{2a}$ and $R^{2b}$ are halogen atoms.

[Item 11]
The compound or the pharmaceutically acceptable salt thereof of any one of items 1 to 6, wherein $R^{2a}$ and $R^{2b}$, together with a carbon atom to which they are attached, form a 3- to 6-membered saturated carbocyclic ring.

[Item 12]
The compound or the pharmaceutically acceptable salt thereof of any one of items 1 to 6, wherein $R^{2a}$ is optionally substituted $C_{6-10}$ aryl, and $R^{2b}$ is a hydrogen atom.

[Item 13]
The compound or the pharmaceutically acceptable salt thereof of any one of items 1 to 6, wherein $R^{2a}$ or $R^{2b}$ is a group substituted with hydroxy or $C_{1-6}$ alkoxy.

[Item 13-1]
The compound or the pharmaceutically acceptable salt thereof of any one of items 1 to 13, wherein X is CR'R", and R' and R" are hydrogen atoms.

[Item 13-2]
The compound or the pharmaceutically acceptable salt thereof of any one of items 1 to 13, wherein X is CR'R", R' is a hydrogen atom, and R" is optionally substituted $C_{1-6}$ alkyl.

[Item 13-3]
The compound or the pharmaceutically acceptable salt thereof of any one of items 1 to 13, wherein X is CR'R", and R' and R" are optionally substituted $C_{1-6}$ alkyl.

[Item 14]
The compound or the pharmaceutically acceptable salt thereof of any one of items 1 and 3 to 13-3, wherein n is 1, and $R^{2c}$ and $R^{2d}$ are hydrogen atoms.

[Item 15]
The compound or the pharmaceutically acceptable salt thereof of any one of items 1 and 3 to 13-3, wherein n is 1, $R^{2c}$ is a hydrogen atom, and $R^{2d}$ is optionally substituted $C_{1-6}$ alkyl.

[Item 16]
The compound or the pharmaceutically acceptable salt thereof of any one of items 1 and 3 to 13-3, wherein n is 1, and $R^{2c}$ and $R^{2d}$ are optionally substituted $C_{1-6}$ alkyl.

[Item 17]
The compound or the pharmaceutically acceptable salt thereof of any one of items 1 and 3 to 13-3, wherein n is 1, and $R^{2c}$ and $R^{2d}$ are halogen atoms.

[Item 18]
The compound or the pharmaceutically acceptable salt thereof of any one of items 1 and 3 to 13-3, wherein n is 1, and $R^{2c}$ and $R^{2d}$, together with a carbon atom to which they are attached, form a 3- to 6-membered saturated carbocyclic ring.

[Item 19]
The compound or the pharmaceutically acceptable salt thereof of any one of items 1 and 3 to 13-3, wherein n is 1, $R^{2c}$ is optionally substituted $C_{6-10}$ aryl, and $R^{2d}$ is a hydrogen atom.

[Item 20]
The compound or the pharmaceutically acceptable salt thereof of any one of items 1 and 3 to 13-3, wherein $R^{2c}$ or $R^{2d}$ is a group substituted with hydroxy or $C_{1-6}$ alkoxy.

[Item 21]
The compound or the pharmaceutically acceptable salt thereof of any one of items 1 to 20, wherein $R^{3a}$, $R^{3b}$, and $R^{3c}$ are each independently a hydrogen atom, or a halogen atom.

[Item 22]
The compound or the pharmaceutically acceptable salt thereof of any one of items 1 to 21, wherein $R^{3a}$, $R^{3b}$, and $R^{3c}$ are each a hydrogen atom.

[Item 22-1]
The compound or the pharmaceutically acceptable salt thereof of any one of items 1 to 21, wherein at least one of $R^{3a}$, $R^{3b}$, and $R^{3c}$ is optionally substituted $C_{1-6}$ alkyl or a halogen atom.

[Item 23]
The compound or the pharmaceutically acceptable salt thereof of any one of items 1 to 22-1, wherein $R^{5a}$ and $R^{5b}$ are each a hydrogen atom.

[Item 24]
The compound or the pharmaceutically acceptable salt thereof of any one of items 1 to 22-1, wherein $R^{5a}$ is a hydrogen atom, and $R^{5b}$ is optionally substituted $C_{1-6}$ alkyl.

[Item 25]
The compound or the pharmaceutically acceptable salt thereof of any one of items 1 to 22-1, wherein $R^{5a}$ and $R^{5b}$ are each optionally substituted $C_{1-6}$ alkyl.

[Item 26]
The compound or the pharmaceutically acceptable salt thereof of any one of items 1 to 25, wherein X is an oxygen atom.

[Item 27]
The compound or the pharmaceutically acceptable salt thereof of any one of items 1 to 25, wherein X is a sulfur atom.

[Item 28]
The compound or the pharmaceutically acceptable salt thereof of any one of items 1 to 25, wherein X is NR.

[Item 29]
The compound or the pharmaceutically acceptable salt thereof of any one of items 1 to 25, wherein X is CR'R".

[Item 29-1]
The compound or the pharmaceutically acceptable salt thereof of any one of items 1 to 3, 5, 7 to 21, 22-1, and 23 to 29, wherein
  $R^1$ is $C_{1-6}$ alkyl optionally substituted with a halogen atom, and
  at least one of $R^{3a}$, $R^{3b}$, and $R^{3c}$ is optionally substituted $C_{1-6}$ alkyl or a halogen atom.

[Item 29-2]
The compound or the pharmaceutically acceptable salt thereof of item 29-1, wherein
  $R^1$ is methyl, and
  at least one of $R^{3a}$, $R^{3b}$, and $R^{3c}$ is methyl, a fluorine atom, or a chlorine atom.

[Item 30]
The compound or the pharmaceutically acceptable salt thereof of item 1, wherein
  X is an oxygen atom,
  n is 0,
  $R^1$ is $C_{1-6}$ alkyl optionally substituted with a halogen atom,
  $R^{2a}$ is a hydrogen atom, and $R^{2b}$ is optionally substituted $C_{1-6}$ alkyl, at least one of $R^{3a}$, $R^{3b}$, and $R^{3c}$ is optionally substituted $C_{1-6}$ alkyl or a halogen atom, and
$R^{5a}$ and $R^{5b}$ are each a hydrogen atom.

[Item 31]

The compound or the pharmaceutically acceptable salt thereof of any one of items 1 to 30, wherein a hydrogen atom of the compound is a deuterium.

[Item 32]

The compound or the pharmaceutically acceptable salt thereof of item 1, selected from the following group of compounds:

1-[(2R,3S)-6-fluoro-2-methyl-2,3-dihydrofuro[3,2-b]pyridin-3-yl]methanamine;
1-[(2R,3S)-2-methyl-2,3-dihydrofuro[3,2-b]pyridin-3-yl]methanamine;
N-methyl-1-[(2R,3S)-2-methyl-2,3-dihydrofuro[3,2-b]pyridin-3-yl]methanamine;
1-[(2R,3S)-6-fluoro-2-methyl-2,3-dihydrofuro[3,2-b]pyridin-3-yl]-N-methylmethanamine;
1-[(2R,3S)-6-fluoro-2-methyl-2,3-dihydrofuro[3,2-b]pyridin-3-yl]-N—($^2$H$_3$)methylmethanamine;
rel-1-[(3'S)-5'-methyl-3'H-spiro[cyclopropane-1,2'-furo[3,2-b]pyridin]-3'-yl]methanamine;
rel-1-[(3'S)-5'-fluoro-3'H-spiro[cyclopropane-1,2'-furo[3,2-b]pyridin]-3'-yl]methanamine;
rel-1-[(3S)-2,2,5-trimethyl-2,3-dihydrofuro[3,2-b]pyridin-3-yl]methanamine;
rel-1-[(3'S)-3'H-spiro[cyclopropane-1,2'-furo[3,2-b]pyridin]-3'-yl]methanamine; and
rac-1-(5-fluoro-2,2-dimethyl-2,3-dihydrofuro[3,2-b]pyridin-3-yl)methanamine.

[Item 33]

A pharmaceutical composition comprising the compound or the pharmaceutically acceptable salt thereof of any one of items 1 to 32.

[Item 34]

The pharmaceutical composition of item 33, wherein the pharmaceutical composition is for treating or preventing a disease or disorder associated with TAAR1.

[Item 35]

The pharmaceutical composition of item 33 or 34, wherein the pharmaceutical composition is for treating or preventing a neurological or psychiatric disorder.

[Item 36]

The pharmaceutical composition of item 35, wherein the neurological or psychiatric disorder is depression, bipolar disorder, pain, schizophrenia, obsessive-compulsive disorder, addiction, social disorder, attention deficit/hyperactivity disorder, anxiety disorder, movement disorder, epilepsy, autism, cognitive dysfunction, psychosis in Alzheimer's disease/Parkinson's disease, irritation/aggression of Parkinson's disease, or hyperphagia.

[Item 37]

A method of treating or preventing a disease or disorder associated with TAAR1 in a subject, characterized by administering to the subject an effective amount of the compound or the pharmaceutically acceptable salt thereof of any one of items 1 to 32.

[Item 38]

A method of treating or preventing a neurological or psychiatric disorder in a subject, characterized by administering to the subject an effective amount of the compound or the pharmaceutically acceptable salt thereof of any one of items 1 to 32.

[Item 39]

The method of item 38, wherein the neurological or psychiatric disorder is depression, bipolar disorder, pain, schizophrenia, obsessive-compulsive disorder, addiction, social disorder, attention deficit/hyperactivity disorder, anxiety disorder, movement disorder, epilepsy, autism, cognitive dysfunction, psychosis in Alzheimer's disease/Parkinson's disease, irritation/aggression of Parkinson's disease, or hyperphagia.

[Item 40]

The compound or the pharmaceutically acceptable salt thereof of any one of items 1 to 32 for use as a drug.

[Item 41]

The compound or the pharmaceutically acceptable salt thereof of item 40, wherein the drug is for treating or preventing a disease or disorder associated with TAAR1.

[Item 42]

The compound or the pharmaceutically acceptable salt thereof of item 40 or 41, wherein the compound or the pharmaceutically acceptable salt thereof is for treating or preventing a neurological or psychiatric disorder.

[Item 43]

The compound or the pharmaceutically acceptable salt thereof of item 42, wherein the neurological or psychiatric disorder is depression, bipolar disorder, pain, schizophrenia, obsessive-compulsive disorder, addiction, social disorder, attention deficit/hyperactivity disorder, anxiety disorder, movement disorder, epilepsy, autism, cognitive dysfunction, psychosis in Alzheimer's disease/Parkinson's disease, irritation/aggression of Parkinson's disease, or hyperphagia.

[Item 44]

A TAAR1 agonist, which is the compound or the pharmaceutically acceptable salt thereof of any one of items 1 to 32.

[Item 45]

Use of the compound or the pharmaceutically acceptable salt thereof of any one of items 1 to 32 in modulation of a TAAR1 receptor.

[Item 46]

A therapeutic agent for a psychiatric disease or central nervous system disease comprising the compound or the pharmaceutically acceptable salt thereof of any one of items 1 to 32 as an active ingredient.

[Item 47]

The therapeutic agent of item 46, wherein the psychiatric disease or central nervous system disease is an organic psychiatric disorder including symptoms; a psychiatric or behavioral disorder due to use of a psychoactive substance; schizophrenia, a schizophrenic disorder, or a delusional disorder; a mood [emotional] disorder; a neurotic disorder, a stress-related disorder, or a somatic symptom disorder; a nonorganic sleep disorder; a disorder that is not due to sexual dysfunction or organic disorder or disease; a pervasive developmental disorder; a behavioral or emotional disorder that generally develops in childhood or adolescence; an extrapyramidal disorder or movement disorder; other degenerative diseases of the nervous system; or a sleep disorder.

[Item 48]

The therapeutic agent of item 46, wherein the psychiatric disease or central nervous system disease is schizophrenia, a positive symptom of schizophrenia, a negative symptom of schizophrenia, a bipolar disorder with a psychiatric characteristic, a depressive disorder with a psychiatric characteristic, a psychotic symptom associated with dementia, a psychotic symptom associated with Alzheimer's disease, a psychotic symptom associated with Lewy body dementia, a psychotic symptom associated with Parkinsonian dementia, a psychotic symptom associated with Parkinson's disease, or irritation, agitation, or aggression associated with Alzheimer's disease.

[Item 49]

The therapeutic agent of item 46, wherein the psychiatric disease or central nervous system disease is schizophrenia, a psychotic symptom associated with dementia, a psychotic symptom associated with Alzheimer's disease, a psychotic symptom associated with Lewy body dementia, or irritation, agitation, or aggression associated with Alzheimer's disease.

[Item 50]

A method for treating a psychiatric disease or central nervous system disease comprising administering a therapeutically effective amount of the compound or the pharmaceutically acceptable salt thereof of any one of items 1 to 32 to a patient in need thereof.

[Item 51]

Use of the compound or the pharmaceutically acceptable salt thereof of any one of items 1 to 32 for the manufacture of a therapeutic agent for a psychiatric disease or central nervous system disease.

[Item 52]

The compound or the pharmaceutically acceptable salt thereof of any one of items 1 to 32 for use in the treatment of a psychiatric disease or central nervous system disease.

[Item 53]

A therapeutic agent for a psychiatric disease or central nervous system disease, comprised of a combination of the compound or the pharmaceutically acceptable salt thereof of any one of items 1 to 32 and at least one agent selected from the group consisting of an antidepressant, an antianxiety drug, a schizophrenia treating drug, a dopamine replacement drug, a dopamine receptor agonist, a Parkinson's disease treating drug, an antiepileptic drug, an analgesic, a hormonal formulation, a migraine treating drug, a B adrenergic receptor antagonist, a dementia treating drug, a mood disorder treating drug, an antiemetic, a sleep inducing agent, and an anticonvulsive drug.

[Item 54]

A therapeutic agent comprising the compound or the pharmaceutically acceptable salt thereof of any one of items 1 to 32 as an active ingredient for the treatment of a psychiatric disease or central nervous system disease by concomitant use with at least one agent selected from the group consisting of an antidepressant, an antianxiety drug, a schizophrenia treating drug, a dopamine replacement drug, a dopamine receptor agonist, a Parkinson's disease treating drug, an antiepileptic drug, an analgesic, a hormonal formulation, a migraine treating drug, a B adrenergic receptor antagonist, a dementia treating drug, a mood disorder treating drug, an antiemetic, a sleep inducing agent, and an anticonvulsive drug.

Effect of the Invention

The disclosed compound has potent agonist activity on the TAAR1 receptor. Furthermore, in a preferable embodiment, this is highly selective for the inhibitory effect on other GPCRs such as dopamine D2 receptor, adrenergic α1 receptor and adrenergic α2 receptor, as well as hERG channel. Therefore, preferable disclosed compounds are useful as highly safe therapeutic agents for neuropsychiatric disorders.

BRIEF DESCRIPTION OF THE DRAWING

FIG. 1 A diagram showing the results of a phencyclidine-induced hyperlocomotion suppression test (Test Example 2-1) for the compound of Example 27.

FIG. 2 A diagram showing the results of a phencyclidine-induced hyperlocomotion suppression test (Test Example 2-2) for the compound of Example 8.

FIG. 3 A diagram showing the results of a phencyclidine-induced hyperlocomotion suppression test (Test Example 2-2) for the compound of Example 49.

MODE FOR CARRYING OUT THE INVENTION

Hereinafter, the present disclosure will be described while showing the best mode. Throughout the present specification, references to the singular should be understood to include the plural unless specifically stated otherwise. Accordingly, singular articles (e.g., "a", "an", "the", etc. in English) should be understood to also include the plural concept, unless specifically stated otherwise. Further, it should be understood that the terms used herein have the meanings commonly used in the art unless otherwise specified. Accordingly, unless defined otherwise, all technical and scientific terms used herein have the same meaning as commonly understood by one of ordinary skill in the art to which this disclosure belongs. In case of conflict, the present specification (including definitions) will control.

Definitions of terms particularly used in the present specification and/or basic technical contents thereof will be explained below as appropriate.

In the present specification, "or (matawa)" is used when "at least one or more" of the items listed in the sentence can be employed. The same shall apply to "or (moshikuwa)". When reference is made herein to "within a range" of two values, the range includes the two values themselves.

The number of substituents in the group defined as "optionally substituted" or "substituted" is not particularly limited as long as the substitution is possible. Furthermore, unless otherwise specified, the description of each group also applies when the group is a part or substituent of another group.

In the present specification, the number of carbon atoms in the definition of "substituent" may be expressed as, for example, "$C_{1-6}$". Specifically, the expression "$C_{1-6}$ alkyl" has the same meaning as an alkyl group having 1 to 6 carbon atoms.

"Halogen" includes fluorine, chlorine, bromine and iodine.

"$C_{1-6}$ alkyl" means a linear or branched saturated hydrocarbon group having 1 to 6 carbon atoms. Preferable examples of $C_{1-6}$ alkyl include "$C_{1-4}$ alkyl", more preferably "$C_{1-3}$ alkyl". Specific examples of "$C_{1-3}$ alkyl" include methyl, ethyl, propyl, 1-methylethyl and the like. Specific examples of "$C_{1-4}$ alkyl" include butyl, 1,1-dimethylethyl, 1-methylpropyl, 2-methyl propyl and the like, in addition to those listed as specific examples of "$C_{1-3}$ alkyl" described above. Specific examples of "$C_{1-6}$ alkyl" include pentyl, 1,1-dimethylpropyl, 1,2-dimethylpropyl, 1-methylbutyl, 2-methylbutyl, 4-methylpentyl, 3-methylpentyl, 2-methylpentyl, 1-methylpentyl, hexyl and the like, in addition to those listed as specific examples of "$C_{1-4}$ alkyl" described above.

"$C_{3-6}$ alkenyl" refers to a linear or branched saturated hydrocarbon group having 3 to 6 carbon atoms and having 1 to 3 double bonds (however, in the formula I, when $R^1$ is "$C_{3-6}$ alkenyl", there is no double bond on the carbon of "$C_{3-6}$ alkenyl" adjacent to a nitrogen atom bonded to R'), and preferably "$C_{3-5}$ alkenyl", and more preferably "$C_{3-4}$ alkenyl". Specific examples of "alkenyl" include allyl, 2-methylallyl and the like.

"$C_{1-6}$ alkoxy" means "$C_{1-6}$ alkyloxy", and the "$C_{1-6}$ alkyl" moiety has the same meaning as the above-mentioned "$C_{1-6}$ alkyl". Preferable examples of "$C_{1-6}$ alkoxy" include "$C_{1-4}$ alkoxy", and more preferably "$C_{1-3}$ alkoxy". Specific examples of "$C_{1-3}$ alkoxy" include methoxy, ethoxy, propoxy, 1-methylethoxy and the like. Specific examples of "$C_{1-4}$ alkoxy" include, butoxy, 1,1-dimethylethoxy, 1-methylpropoxy, 2-methylpropoxy and the like, in addition to those listed as specific examples of "$C_{1-3}$ alkyl" described above. Specific examples of "$C_{1-6}$ alkoxy" include pentyloxy, 1,1-dimethylpropoxy, 1,2-dimethylpropoxy, 1-methylbutoxy, 2-methylbutoxy, 4-methylpentyloxy, 3-methylpentyloxy, 2-methylpentyloxy, 1-methylpentyloxy, hexyloxy and the like, in addition to those listed as specific examples of "$C_{1-4}$ alkyl" described above.

"3- to 6-membered saturated heterocycle" refers to a saturated ring constituted of 3 to 6 atoms containing 1 to 2 atoms selected independently from the group consisting of a nitrogen atom, an oxygen atom and a sulfur atom, in addition to a carbon atom, and includes those having a partially unsaturated bond and those having a bridged structure. "3- to 6-membered saturated heterocycle" is preferably "4- to 6-membered monocyclic saturated heterocycle" and more preferably includes "5- or 6-membered monocyclic saturated heterocycle". Specific examples of "5- or 6-membered monocyclic saturated heterocycle" include, for example, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, oxoimidazolidinyl, dioxoimidazolidinyl, oxooxazolidinyl, dioxooxazolidinyl, dioxothiazolidinyl, tetrahydrofuranyltetrahydropyranyl and the like. Examples of "4- to 6-membered monocyclic saturated heterocycle" include oxetanyl, azetidinyl and the like, in addition to those listed as specific examples of "5- or 6-membered monocyclic saturated heterocycle" described above.

"3- to 6-membered saturated carbocycle" refers to a cyclic saturated hydrocarbon having 3 to 6 carbon atoms, and includes those having a partially unsaturated bond and those having a bridged structure. Preferable examples of "3- to 6-membered saturated carbocycle" include "5- or 6-membered monocyclic saturated carbocycle." Specific examples of "5- or 6-membered monocyclic saturated carbocycle" include cyclopentane, cyclohexane and the like. Specific examples of "3- to 6-membered saturated carbocycle" include cyclopropane, cyclobutane and the like, in addition to those listed as specific examples of "5- or 6-membered monocyclic saturated carbocycle" described above.

"$C_{6-10}$ aryl" means a monocyclic or bicyclic aromatic hydrocarbon group having 6 to 10 carbon atoms. Specific examples of "$C_{6-10}$ aryl" include phenyl, 1-naphthyl, 2-naphthyl and the like. "$C_{6-10}$ aryl" is preferably phenyl. "$C_{6-10}$ aryl" may have a condensed ring structure.

With respect to "substituent" of optionally substituted $C_{1-6}$ alkyl, optionally substituted $C_{3-6}$ alkenyl, $C_{1-6}$ alkoxy, optionally substituted 3- to 6-membered saturated carbocycle, optionally substituted the 3- to 6-membered saturated heterocycle and the optionally substituted aryl group, one or more substituents of any type may be present at any chemically possible position, and when there are two or more substituents, each substituent may be the same or different. Specific examples of the substituent include a halogen atom, a $C_{1-6}$ alkyl group, a $C_{1-4}$ alkoxy group, a cyano group, a benzyloxy group, a phenyl group, a hydroxy group, a methanesulfonyl group, and a substituted or unsubstituted amino group.

Specific examples of the substituent on optionally substituted $C_{1-6}$ alkyl and optionally substituted $C_{3-6}$ alkenyl are a halogen atom, hydroxy or $C_{1-6}$ alkoxy, and specific examples of the substituent on optionally substituted $C_{6-10}$ aryl and optionally substituted 3- to 6-membered saturated carbocycle are a halogen atom, hydroxy, $C_{1-6}$ alkyl or $C_{1-6}$ alkoxy.

In the disclosed compounds represented by the formula I, preferable examples of X, n, $R^1$, $R^{2a}$, $R^{2b}$, $R^{2c}$, $R^{2d}$, R, R', R'', $R^{3a}$, $R^{3b}$, $R^{3c}$, $R^4$, $R^{5a}$, and $R^{5b}$ are as follows, but the technical scope of the present disclosure is not limited to the range of the compounds listed below.

Preferable embodiments include those wherein n is 0.

Preferable embodiments include those wherein n is 1.

Preferable embodiments include those wherein $R^1$ is a hydrogen atom.

Preferable embodiments include those wherein $R^1$ is $C_{1-6}$ alkyl optionally substituted with a halogen atom.

Preferable embodiments include those wherein $R^1$ is methyl.

Preferable embodiments include those wherein $R^{2a}$ and $R^{2b}$ are hydrogen atoms.

Preferable embodiments include those wherein $R^{2a}$ is a hydrogen atom and $R^{2b}$ is an optionally substituted $C_{1-6}$ alkyl.

Preferable embodiments include those wherein $R^{2a}$ and $R^{2b}$ are optionally substituted $C_{1-6}$ alkyl.

Preferable embodiments include those wherein $R^{2a}$ and $R^{2b}$ are halogen atoms.

Preferable embodiments include those wherein $R^{2a}$ and $R^{2b}$, together with a carbon atom to which they are attached, form a 3- to 6-membered saturated carbocycle.

Preferable embodiments include those wherein $R^{2a}$ is optionally substituted $C_{6-10}$ aryl and $R^{2b}$ is a hydrogen atom.

Preferable embodiments include those wherein $R^{2a}$ or $R^{2b}$ is a group substituted with hydroxy or $C_{1-6}$ alkoxy.

Preferable embodiments include those wherein n is 1 and $R^{2c}$ and $R^{2d}$ are hydrogen atoms.

Preferable embodiments include those wherein n is 1, $R^{2c}$ is a hydrogen atom, and $R^{2d}$ is optionally substituted $C_{1-6}$ alkyl.

Preferable embodiments include those wherein n is 1 and $R^{2c}$ and $R^{2d}$ are optionally substituted $C_{1-6}$ alkyl.

Preferable embodiments include those wherein n is 1 and $R^{2c}$ and $R^{2d}$ are halogen atoms.

Preferable embodiments include those wherein n is 1 and $R^{2c}$ and $R^{2d}$, together with a carbon atom to which they are attached, form a 3- to 6-membered saturated carbocycle.

Preferable embodiments include those wherein n is 1, $R^{2c}$ is optionally substituted $C_{6-10}$ aryl, and $R^{2d}$ is a hydrogen atom.

Preferable embodiments include those wherein $R^{2c}$ or $R^{2d}$ is a group substituted with hydroxy or $C_{1-6}$ alkoxy.

Preferable embodiments include those wherein $R^{3a}$, $R^{3b}$, and $R^{3c}$ are each independently a hydrogen atom, an optionally substituted $C_{1-6}$ alkyl, or a halogen atom.

Preferable embodiments include those wherein $R^{3a}$, $R^{3b}$, and $R^{3c}$ are each independently a hydrogen atom or a halogen atom.

Preferable embodiments include those wherein $R^{3a}$, $R^{3b}$, and $R^{3c}$ are each a hydrogen atom.

Preferable embodiments include those wherein $R^{3a}$, $R^{3b}$, and $R^{3c}$ are each optionally substituted $C_{1-6}$ alkyl.

Preferable embodiments include those wherein at least one of $R^{3a}$, $R^{3b}$, and $R^{3c}$ is optionally substituted $C_{1-6}$ alkyl or halogen atom.

Preferable embodiments include those wherein $R^{5a}$ and $R^{5b}$ are each a hydrogen atom.

Preferable embodiments include those wherein $R^{5a}$ is a hydrogen atom and $R^{5b}$ is optionally substituted $C_{1-6}$ alkyl.

Preferable embodiments include those wherein $R^{5a}$ and $R^{5b}$ are each optionally substituted $C_{1-6}$ alkyl.

Preferable embodiments include those wherein X is an oxygen atom.

Preferable embodiments include those wherein X is a sulfur atom.

Preferable embodiments include those wherein X is NR.

Preferable embodiments include those wherein X is CR'R''.

Preferable embodiments include those wherein $R^1$ is $C_{1-6}$ alkyl optionally substituted with a halogen atom, and at least one of $R^{3a}$, $R^{3b}$, and $R^{3c}$ is optionally substituted $C_{1-6}$ alkyl or halogen atoms.

Preferable embodiments include those wherein $R^1$ is methyl, and at least one of $R^{3a}$, $R^{3b}$, and $R^{3c}$ is methyl, a fluorine atom, or a chlorine atom.

Preferable embodiments include those wherein X is an oxygen atom, n is 0, $R^1$ is $C_{1-6}$ alkyl optionally substituted with a halogen atom, $R^{2a}$ is a hydrogen atom, $R^{2b}$ is optionally substituted $C_{1-6}$ alkyl, at least one of $R^{3a}$, $R^{3b}$, and $R^{3c}$ is optionally substituted $C_{1-6}$ alkyl or halogen atom, and $R^{1a}$ and $R^b$ are each a hydrogen atom.

The compounds of the formula I may also exist as tautomers. Accordingly, the disclosed compounds also include tautomers of compounds represented by the formula I.

The compounds of the formula I may also have at least one asymmetric carbon atom. Therefore, the disclosed compounds include not only racemates of the compounds represented by the formula I but also optically active forms of these compounds. If the compound represented by the formula I has two or more asymmetric carbon atoms, stereoisomerism may occur. Accordingly, the disclosed compounds also include stereoisomers of these compounds and mixtures thereof. In the structural formula, "rac." means racemic form, "chiral" means optically active form, and "abs." means absolute configuration.

Further, derivatives obtained by converting any one or more atoms of the compound represented by the formula I into isotopes are also included in the compound represented by the formula I. For example, deuterium-converted products wherein $^1H$ is converted to $^2H(D)$ and products obtained by conversion into radioactive isotopes such as $^{11}C$ and $^{18}F$ are also included in the compound represented by the formula I.

The compounds of the formula I and their pharmaceutically acceptable salts may also exist in the form of hydrates and/or solvates, and therefore, these hydrates or solvates such as ethanol solvates are also included in the disclosed compound. Furthermore, the disclosed compounds include all embodiments of crystalline forms.

When the compound represented by the formula I has an acidic group, examples of pharmaceutically acceptable salts include alkali metal salts such as sodium salts, potassium salts and the like, and alkaline earth metal salts such as calcium salts, magnesium salts and the like, inorganic metal salts such as zinc salts, and organic base salts such as triethylamine, triethanolamine, trihydroxymethylaminomethane, amino acids and the like.

If the compound of the formula I has a basic group, examples thereof include inorganic acid salts such as hydrochloride, hydrobromide, sulfate, phosphate, nitrate and the like, and organic acid salts such as acetate, propionate, succinate, lactate, malate, tartrate, citrate, maleate, fumarate, methanesulfonate, p-toluenesulfonate, benzenesulfonate, ascorbate and the like.

The method for producing the disclosed compound will be described below with examples, but the present disclosure is not limited thereto.

Production Method

The disclosed compound is synthesized by a method that combines the production method shown below and a known synthesis method.

The compounds in the reaction formula may each form a salt, and examples of the salt include those similar to the salt of the compound represented by the formula I. Note that these reactions are merely illustrative, and the disclosed compounds can also be produced by other methods as appropriate based on the knowledge of those skilled in organic synthesis.

In each production method described below, even if the use of a protecting group is not specifically specified, if there is a functional group that requires protection, the desired product may be obtained by protecting the functional group as necessary and deprotecting it after completion of the reaction or after performing a series of reactions.

As the protecting group, usual protecting groups described in literatures (T W Greene and P G M Wuts, "Protective Groups in Organic Synthesis", 3rd Ed., John Wiley and Sons, inc., New York (1999)) and the like, can be used. More specifically, examples of amino protecting groups include benzyloxycarbonyl, tert-butoxycarbonyl, acetyl, benzyl and the like. Examples of hydroxy protection include trialkylsilyl, acetyl, benzyl and the like.

Introduction and removal of protecting groups can be carried out by methods commonly used in organic synthetic chemistry (e.g., T. W. Greene and P. G. M. Wuts, "Protective Groups in Organic Synthesis", 3rd Ed., John Wiley and Sons, inc., New York (1999)) or methods similar thereto.

Production Method 1

Among the compounds represented by the formula I, the compound represented by the formula (1a) is produced, for example, by a method shown below.

[Chemical Formula 4]

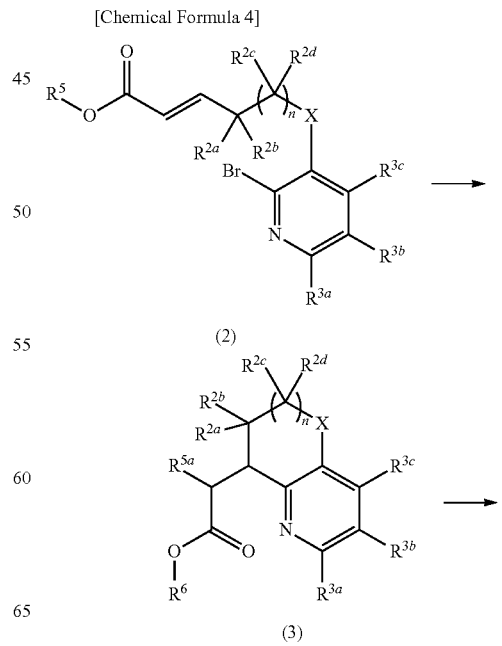

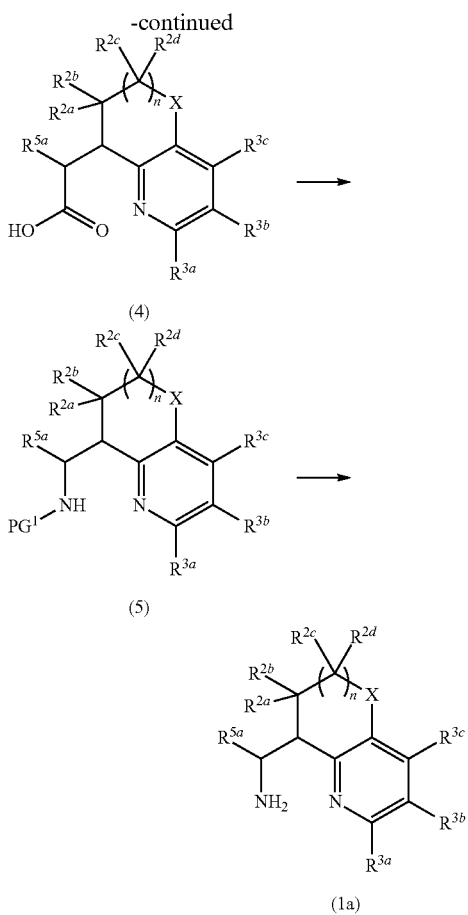

wherein, n, $R^{2a}$, $R^{2b}$, $R^{2c}$, $R^{2d}$, $R^{3a}$, $R^{3b}$, $R^{3c}$, $R^{5a}$ and X have the same meanings as in the item 1, and $R^6$ represents optionally substituted $C_{1-6}$ alkyl, and $PG^1$ represents an alkyl carbamate such as tert-butoxycarbonyl or benzyloxycarbonyl.

The compound (1a) is produced by treating the compound (5) with an appropriate acid when $PG^1$ is tert-butoxycarbonyl. The treatment temperature usually ranges from −20° C. to the boiling point of the solvent used. The reaction time varies depending on conditions such as reaction temperature, acid used, raw materials, solvent and the like, but is usually 10 minutes to 48 hours.

Specific examples of the inert solvent include halogenated hydrocarbons such as chloroform, dichloromethane and the like, aromatic hydrocarbons such as benzene, toluene and the like, ether solvents such as diethyl ether, tetrahydrofuran, 1,4-dioxane, 1,2-dimethoxyethane and the like, lower alcohols such as methanol, ethanol, 2-propanol and the like, aprotic polar solvents such as acetonitrile, dimethylformamide, N-methyl-2-pyrrolidinone, dimethyl sulfoxide and the like, and mixed solvents thereof.

Specific examples of the acid include inorganic acids such as hydrochloric acid, sulfuric acid and the like, and organic acids such as trifluoroacetic acid and the like.

When $PG^1$ is benzyloxycarbonyl, the compound (1a) is produced by hydrogenolyzing the compound (5) in a suitable inert solvent under normal pressure or pressurized hydrogen atmosphere. Specific examples of the catalyst used in this hydrogenolysis reaction include palladium-based catalysts such as palladium-carbon, palladium hydroxide-carbon and the like. The reaction temperature usually ranges from 0° C. to the boiling point of the solvent used. The reaction time varies depending on conditions such as reaction temperature, catalyst used, raw materials, solvent and the like, but is usually 10 minutes to 48 hours.

Specific examples of the inert solvent include ester solvents such as ethyl acetate and the like, aromatic hydrocarbons such as benzene, toluene and the like, ether solvents such as diethyl ether, tetrahydrofuran (THF), 1,4-dioxane, 1,2-dimethoxyethane and the like, alcohol solvents such as methanol, ethanol, 2-propanol and the like, aprotic polar solvents such as dimethylformamide, N-methyl-2-pyrrolidinone, dimethyl sulfoxide and the like, and mixed solvents thereof.

The compound (5) is produced by reacting the compound (4) with diphenylphosphoric azide in a suitable inert solvent in the presence of an appropriate base at room temperature for about 1 hour, and reacting with stirring at an appropriate temperature of 50° C. to 100° C. for 1 hour, and then reacting with an alcohol such as benzyl alcohol, tert-butanol or the like at an appropriate temperature of 50° C. to 100° C.

The compound (5) is also produced by reacting the compound (4) with diphenylphosphoric azide in a suitable inert solvent in the presence of an appropriate base at room temperature for about 1 hour, heating with stirring at an appropriate temperature of 50° C. to 100° C. for about 1 hour, reacting with a base such as sodium hydroxide, potassium hydroxide or the like in the presence of water, and then reacting with di-tert-butyl dicarbonate in the presence of an appropriate base as necessary.

The reaction time varies depending on conditions such as reaction temperature, base used, alcohol, raw materials, solvent and the like, but is usually 10 minutes to 48 hours.

Specific examples of the base include organic bases such as triethylamine, diisopropylethylamine, pyridine and the like, inorganic bases such as potassium carbonate, sodium carbonate, cesium carbonate, potassium hydrogen carbonate, sodium hydrogen carbonate, potassium dihydrogen phosphate, dipotassium hydrogen phosphate, potassium phosphorus, sodium dihydrogen phosphate, disodium hydrogen phosphate, sodium phosphate, potassium hydroxide, sodium hydroxide, sodium hydride and the like, metal alkoxides such as sodium methoxide, potassium tert-butoxide, and the like.

Specific examples of the inert solvent include halogenated hydrocarbons such as chloroform, dichloromethane and the like, aromatic hydrocarbons such as benzene, toluene and the like, ether solvents such as diethyl ether, tetrahydrofuran (THF), 1,4-dioxane and the like, aprotic polar solvents such as acetonitrile, acetone, methyl ethyl ketone, dimethylformamide, N-methyl-2-pyrrolidinone, dimethyl sulfoxide and the like, and mixed solvents thereof.

The compound (4) is produced by hydrolyzing the compound (3) with a base such as potassium hydroxide, sodium hydroxide, sodium hydride, lithium hydroxide and the like in a suitable solvent. The treatment temperature usually ranges from about −20° C. to the boiling point of the solvent used. The reaction time varies depending on conditions such as reaction temperature, base used, raw materials, solvent and the like, but is usually 10 minutes to 48 hours.

Specific examples of the solvent include lower alcohols such as methanol, ethanol, 2-propanol and the like, water, and mixed solvents thereof.

The compound (3) is produced by reacting the compound (2) with tributyltin hydride in the presence of a catalytic amount of azobisisobutyronitrile in a suitable inert solvent. The reaction temperature usually ranges from 50° C. to the boiling point of the solvent. The reaction time varies depending on conditions such as reaction temperature, raw materials used, solvent and the like, but is usually 10 minutes to 48 hours.

Specific examples of the inert solvent include aromatic hydrocarbons such as benzene, toluene and the like, ether solvents such as diethyl ether, tetrahydrofuran (THF), 1,4-dioxane and the like, and mixed solvents thereof.

Production Method 2

Among the compounds represented by the formula I, the compound represented by the formula (1b) is produced, for example, by a method shown below.

[Chemical Formula 5]

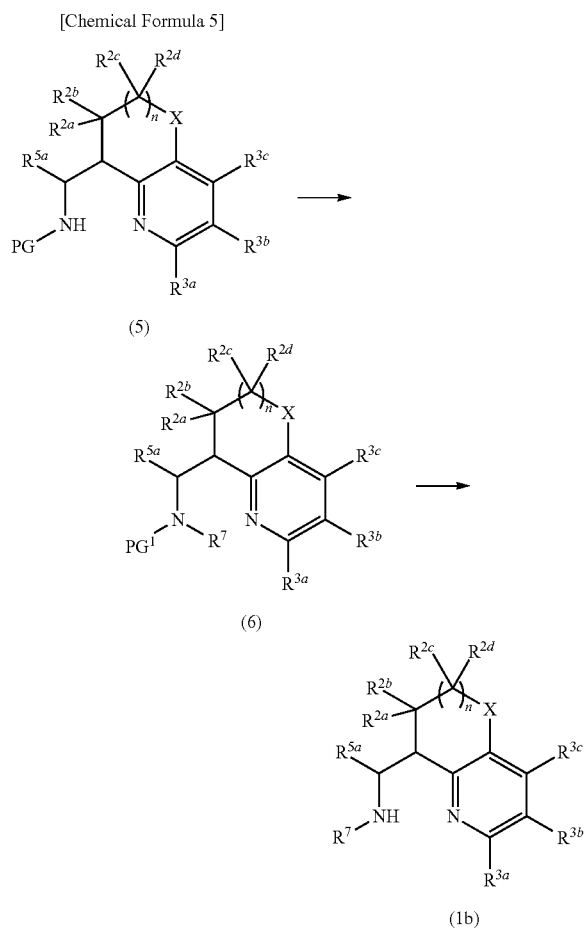

(5)

(6)

(1b)

wherein, n, $R^{2a}$, $R^{2b}$, $R^{2c}$, $R^{2d}$, $R^{3a}$, $R^{3b}$, $R^{3c}$, $R^{5a}$ and X have the same meanings as in item 1, and $PG^1$ represents an alkyl carbamate such as tert-butoxycarbonyl, benzyloxycarbonyl or the like, and $R^7$ represents optionally substituted $C_{1-6}$ alkyl.

The compound (1b) is produced by treating the compound (6) with an appropriate acid when $PG^1$ is tert-butoxycarbonyl. The treatment temperature usually ranges from −20° C. to the boiling point of the solvent used. The reaction time varies depending on conditions such as reaction temperature, acid used, raw materials, solvent and the like, but is usually 10 minutes to 48 hours.

Specific examples of the inert solvent include halogenated hydrocarbons such as chloroform, dichloromethane and the like, aromatic hydrocarbons such as benzene, toluene and the like, ether solvents such as diethyl ether, tetrahydrofuran, 1,4-dioxane, 1,2-dimethoxyethane and the like, lower alcohols such as methanol, ethanol, 2-propanol and the like, aprotic polar solvents such as acetonitrile, dimethylformamide, N-methyl-2-pyrrolidinone, dimethyl sulfoxide and the like, and mixed solvents thereof.

Specific examples of the acid include inorganic acids such as hydrochloric acid, sulfuric acid and the like, and organic acids such as trifluoroacetic acid, and the like.

When $PG^1$ is benzyloxycarbonyl, the compound (1b) is produced by hydrogenolyzing the compound (6) in a suitable inert solvent under normal pressure or pressurized hydrogen atmosphere. Specific examples of the catalyst used in this hydrogenolysis reaction include palladium-based catalysts such as palladium-carbon, palladium hydroxide-carbon and the like. The reaction temperature usually ranges from 0° C. to the boiling point of the solvent used. The reaction time varies depending on conditions such as reaction temperature, catalyst used, raw materials, solvent and the like, but is usually 10 minutes to 48 hours.

Specific examples of the inert solvent include ester solvents such as ethyl acetate and the like, aromatic hydrocarbons such as benzene, toluene and the like, ether solvents such as diethyl ether, tetrahydrofuran (THF), 1,4-dioxane, 1,2-dimethoxyethane and the like, alcohol solvents such as methanol, ethanol, 2-propanol and the like, aprotic polar solvents such as dimethylformamide, N-methyl-2-pyrrolidinone, dimethyl sulfoxide and the like, and mixed solvents thereof.

The compound (6) is produced by reacting the compound (5) with an alkylating agent such as iodomethane or the like in a suitable inert solvent in the presence of a suitable base. The reaction may be carried out in the presence of a phase transfer catalyst, if necessary. The reaction temperature usually ranges from about −20° C. to the boiling point of the solvent used. The reaction time varies depending on conditions such as reaction temperature, base used, raw materials, solvent and the like, but is usually 10 minutes to 48 hours.

Specific examples of the base include organic bases such as triethylamine, diisopropylethylamine, pyridine and the like, inorganic bases such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, sodium hydride and the like, metal alkoxides such as sodium methoxide, potassium tert-butoxide, and the like.

Specific examples of the phase transfer catalyst include tetrabutylammonium hydrogen sulfate, and the like.

Specific examples of the inert solvent include halogenated hydrocarbons such as chloroform, dichloromethane and the like, aromatic hydrocarbons such as benzene, toluene and the like, ether solvents such as diethyl ether, tetrahydrofuran (THF), 1,4-dioxane and the like, lower alcohols such as methanol, ethanol, 2-propanol and the like, aprotic polar solvents such as acetonitrile, acetone, methyl ethyl ketone, dimethyl formamide, N-methyl-2-pyrrolidinone, dimethyl sulfoxide and the like, and mixed solvents thereof.

Production Method 3

The compound represented by the formula (2) is produced, for example, by a method shown below.

[Chemical Formula 6]

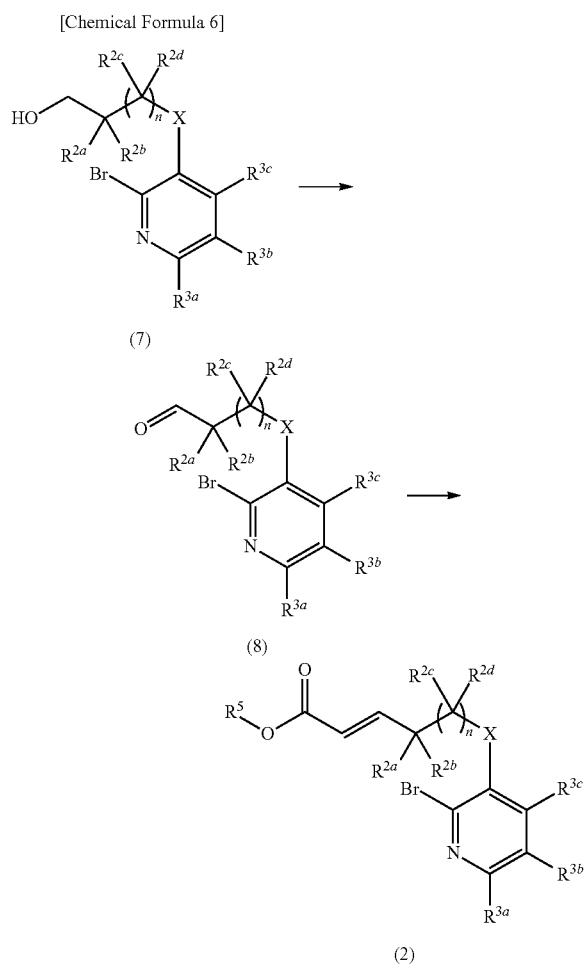

wherein, n, $R^{2a}$, $R^{2b}$, $R^{2c}$, $R^{2d}$, $R^{3a}$, $R^{3b}$, $R^{3c}$, and X have the same meanings as in item 1, and $R^6$ represents optionally substituted $C_{1-6}$ alkyl.

The compound (2) is produced by reacting the compound (8) with a (triphenylphosphoranylidene)acetate such as ethyl (triphenylphosphoranylidene)acetate in a suitable inert solvent. The compound (2) is also produced by reacting the compound (2) with a phosphonium salt such as triphenyl (carboethoxymethyl)phosphonium bromide or a dialkylphosphonoacetate such as ethyl diethylphosphonoacetate in the presence of an appropriate base. The reaction temperature usually ranges from about −20° C. to the boiling point of the solvent used. The reaction time varies depending on conditions such as reaction temperature, base used, raw materials, solvent and the like, but is usually 10 minutes to 48 hours.

Specific examples of the base include organic bases such as triethylamine, diisopropylethylamine, pyridine and the like, inorganic bases such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, sodium hydride and the like, metal alkoxides such as sodium methoxide, potassium tert-butoxide, and the like.

Specific examples of the inert solvent include halogenated hydrocarbons such as chloroform, dichloromethane and the like, aromatic hydrocarbons such as benzene, toluene and the like, ether solvents such as diethyl ether, tetrahydrofuran (THF), 1,4-dioxane and the like, aprotic polar solvents such as acetonitrile, acetone, methyl ethyl ketone, dimethylformamide, N-methyl-2-pyrrolidinone, dimethyl sulfoxide and the like, and mixed solvents thereof.

The compound (8) is produced by reacting the compound (7) with an oxidizing agent such as Dess-Martin periodinane in a suitable inert solvent. The compound (8) is also produced by reacting the compound (7) with a sulfur trioxide pyridine complex in dimethyl sulfoxide in the presence of a tertiary alkylamine such as triethylamine. The reaction temperature usually ranges from about −20° C. to the boiling point of the solvent used. The reaction time varies depending on conditions such as reaction temperature, raw materials used, solvent and the like, but is usually 10 minutes to 48 hours.

Specific examples of the inert solvent include halogenated hydrocarbons such as chloroform, dichloromethane and the like, aromatic hydrocarbons such as benzene, toluene and the like, ether solvents such as diethyl ether, tetrahydrofuran (THF), 1,4-dioxane and the like, aprotic polar solvents such as acetonitrile, acetone, methyl ethyl ketone, dimethylformamide, N-methyl-2-pyrrolidinone, dimethyl sulfoxide and the like, and mixed solvents thereof.

Production Method 4

Among the compounds represented by the formula (2), the compound represented by the formula (2a) is produced, for example, by a method shown below.

[Chemical Formula 7]

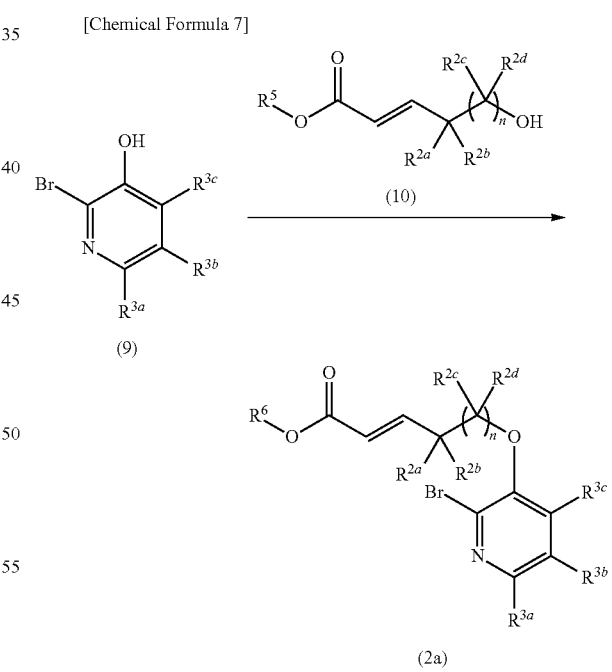

wherein, n, $R^{2a}$, $R^{2b}$, $R^{2c}$, $R^{2d}$, $R^{3a}$, $R^{3b}$, and $R^{3c}$ have the same meanings as in Item 1, and $R^6$ represents optionally substituted $C_{1-6}$ alkyl.

The compound (2a) is produced by reacting the compound (9) with an alcohol represented by the formula (10) in a suitable inert solvent in the presence of triphenylphosphine and an azodicarboxylic acid ester such as diisopropyl azodicarboxylate. The reaction temperature usually ranges from about −20° C. to the boiling point of the solvent used. The reaction time varies depending on conditions such as reaction temperature, raw materials used, solvent and the like, but is usually 10 minutes to 48 hours.

Specific examples of the inert solvent include halogenated hydrocarbons such as chloroform, dichloromethane and the like, aromatic hydrocarbons such as benzene, toluene and the like, ether solvents such as diethyl ether, tetrahydrofuran (THF), 1,4-dioxane and the like, aprotic polar solvents such as acetonitrile, acetone, methyl ethyl ketone, dimethylformamide, N-methyl-2-pyrrolidinone, dimethyl sulfoxide and the like, and mixed solvents thereof.

Production Method 5

Among the compounds represented by the formula (7), the compound represented by the formula (7a) is produced, for example, by a method shown below.

and an azodicarboxylic acid ester such as diisopropyl azodicarboxylate or the like, and then treating with an appropriate acid. The reaction temperature usually ranges from about −20° C. to the boiling point of the solvent used. The reaction time varies depending on conditions such as reaction temperature, raw materials used, solvent and the like, but is usually 10 minutes to 48 hours.

Specific examples of the inert solvent include halogenated hydrocarbons such as chloroform, dichloromethane and the like, aromatic hydrocarbons such as benzene, toluene and the like, ether solvents such as diethyl ether, tetrahydrofuran (THF), 1,4-dioxane and the like, aprotic polar solvents such as acetonitrile, acetone, methyl ethyl ketone, dimethylformamide, N-methyl-2-pyrrolidinone, dimethyl sulfoxide and the like, and mixed solvents thereof.

[Chemical Formula 8]

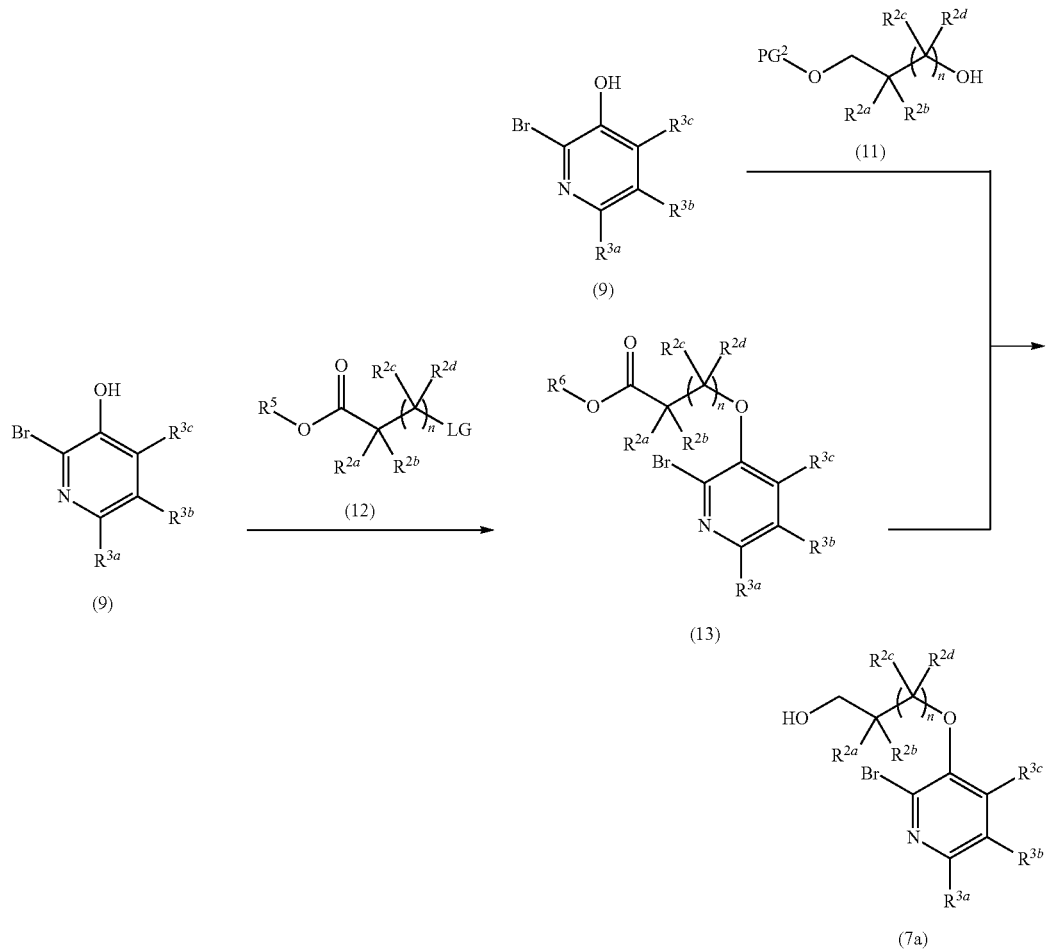

wherein, n, $R^{2a}$, $R^{2b}$, $R^{2c}$, $R^{2d}$, $R^{3a}$, $R^{3b}$, and $R^{3c}$ have the same meanings as in Item 1, $R^8$ represents optionally substituted $C_{1-6}$ alkyl, $PG^2$ represents a trialkylsilyl such as tert-butyldimethylsilyl or the like, and LG represents a leaving group (e.g., iodine, bromine, chlorine, substituted sulfonyl (e.g., methanesulfonyl, p-toluenesulfonyl, etc.)).

The compound (7a) is produced by reacting the compound (9) with an alcohol represented by the formula (11) in a suitable inert solvent in the presence of triphenylphosphine Specific examples of the acid include inorganic acids such as hydrochloric acid, sulfuric acid and the like, and organic acids such as trifluoroacetic acid, and the like.

The compound (7a) is produced by reacting the compound (13) with a suitable reducing agent in a suitable inert solvent. The reaction temperature usually ranges from about −20° C. to the boiling point of the solvent used. The reaction time varies depending on conditions such as reaction temperature, raw materials used, solvent and the like, but is usually 10 minutes to 48 hours.

Specific examples of the reducing agent include complex hydrogen compounds such as lithium aluminum hydride, sodium borohydride, sodium cyanoborohydride, diisobutylaluminum hydride and the like, borane complexes (borane-dimethylsulfide complex, borane-tetrahydrofuran complex, etc.)), and the like.

Specific examples of the inert solvent include halogenated hydrocarbons such as chloroform, dichloromethane and the like, aromatic hydrocarbons such as benzene, toluene and the like, ether solvents such as diethyl ether, tetrahydrofuran (THF), 1,4-dioxane and the like, and mixed solvents thereof.

The compound (13) is produced by reacting the compound (9) with an alkylating agent represented by the formula (12) in a suitable inert solvent in the presence of a suitable base. The reaction may be carried out in the presence of a phase transfer catalyst, if necessary. The reaction temperature usually ranges from about −20° C. to the boiling point of the solvent used. The reaction time varies depending on conditions such as reaction temperature, base used, raw materials, solvent and the like, but is usually 10 minutes to 48 hours.

Specific examples of the base include organic bases such as triethylamine, diisopropylethylamine, pyridine and the like, inorganic bases such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, sodium hydride and the like, metal alkoxides such as sodium methoxide, potassium tert-butoxide, and the like.

Specific examples of the phase transfer catalyst include tetrabutylammonium hydrogen sulfate, and the like.

Specific examples of the inert solvent include halogenated hydrocarbons such as chloroform, dichloromethane and the like, aromatic hydrocarbons such as benzene, toluene and the like, ether solvents such as diethyl ether, tetrahydrofuran (THF), 1,4-dioxane and the like, lower alcohols such as methanol, ethanol, 2-propanol and the like, aprotic polar solvents such as acetonitrile, acetone, methyl ethyl ketone, dimethyl formamide, N-methyl-2-pyrrolidinone, dimethyl sulfoxide and the like, and mixed solvents thereof.

Production Method 6

Among the compounds represented by the formula (7), the compound represented by the formula (7b) is produced, for example, by a method shown below.

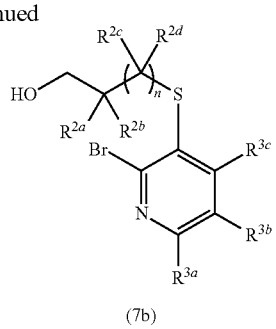

(7b)

wherein, n, $R^{2a}$, $R^{2b}$, $R^{2c}$, $R^{2d}$, $R^{3a}$, $R^{3b}$, and $R^{3c}$ have the same meanings as in item 1.

The compound (7b) is produced by reacting the compound (14) with a thiol represented by the formula (15) in a suitable inert solvent in the presence of a suitable base. The reaction may be carried out in the presence of a phase transfer catalyst, if necessary. The reaction temperature usually ranges from about −20° C. to the boiling point of the solvent used. The reaction time varies depending on conditions such as reaction temperature, base used, raw materials, solvent and the like, but is usually 10 minutes to 48 hours.

Specific examples of the base include organic bases such as triethylamine, diisopropylethylamine, pyridine and the like, inorganic bases such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, sodium hydride and the like, metal alkoxides such as sodium methoxide, potassium tert-butoxide, and the like.

Specific examples of the phase transfer catalyst include tetrabutylammonium hydrogen sulfate, and the like.

Specific examples of the inert solvent include halogenated hydrocarbons such as chloroform, dichloromethane and the like, aromatic hydrocarbons such as benzene, toluene and the like, ether solvents such as diethyl ether, tetrahydrofuran (THF), 1,4-dioxane and the like, lower alcohols such as methanol, ethanol, 2-propanol and the like, aprotic polar solvents such as acetonitrile, acetone, methyl ethyl ketone, dimethyl formamide, N-methyl-2-pyrrolidinone, dimethyl sulfoxide and the like, and mixed solvents thereof.

Production Method 7

Among the compounds represented by the formula I, the compound represented by the formula (1c) is produced, for example, by a method shown below.

[Chemical Formula 9]

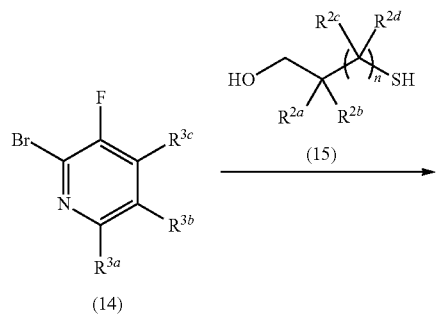

[Chemical Formula 10]

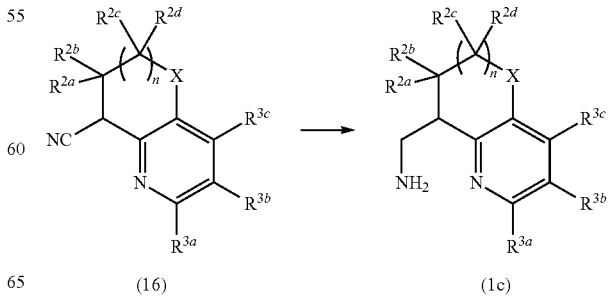

wherein, n, $R^{2a}$, $R^{2b}$, $R^{2c}$, $R^{2d}$, $R^{3a}$, $R^{3b}$, $R^{3c}$ and X have the same meanings as in item 1.

The compound (1c) is produced by reacting the compound (16) with a suitable reducing agent in a suitable inert solvent. The reaction temperature usually ranges from about −20° C. to the boiling point of the solvent used. The reaction time varies depending on conditions such as reaction temperature, raw materials used, solvent and the like, but is usually 10 minutes to 48 hours.

Specific examples of the reducing agent include complex hydrogen compounds such as lithium aluminum hydride, sodium borohydride, sodium cyanoborohydride, diisobutylaluminum hydride and the like, borane complexes (borane-dimethylsulfide complex, borane-tetrahydrofuran complex, etc.)), and the like.

Specific examples of the inert solvent include halogenated hydrocarbons such as chloroform, dichloromethane and the like, aromatic hydrocarbons such as benzene, toluene and the like, ether solvents such as diethyl ether, tetrahydrofuran (THF), 1,4-dioxane and the like; and mixed solvents thereof.

By appropriately combining the above production methods, it is possible to obtain a disclosed compound having a desired substituent at a desired position. Isolation and purification of intermediates and products in the above production method can be carried out by appropriately combining methods used in ordinary organic synthesis, such as filtration, extraction, washing, drying, concentration, crystallization, various chromatography and the like. Moreover, the intermediate can also be subjected to the next reaction without being particularly purified.

Depending on the reaction conditions, some of the raw material compounds or intermediates in the above production method may exist in the form of salts such as hydrochlorides, but they can be used as they are or in free form. If the raw material compound or intermediate is obtained in the form of a salt and it is desired to use or obtain the raw material compound or intermediate in a free form, they can be dissolved or suspended in a suitable solvent and neutralized with a base such as an aqueous sodium bicarbonate solution or the like, to be converted into the free form.

Isomers such as tautomers such as ketoenol, positional isomers, geometric isomers and optical isomers may exist in the compound represented by the formula I or a pharmaceutically acceptable salt thereof, and all possible isomers, including these, and mixtures of such isomers in any ratio are encompassed by the present disclosure.

Further, optical isomers can be separated by performing a known separation process such as a method using an optically active column or a fractional crystallization method in an appropriate step of the above production method. Moreover, an optically active substance can also be used as a starting material.

If it is desired to obtain the salt of the compound represented by the formula I, it may be permissible to simply purify it as it is if the salt of the compound represented by the formula I is obtained, alternatively, when the compound represented by formula I is obtained in free form, the compound represented by formula I may be dissolved or suspended in a suitable solvent and an acid or base may be added to form a salt.

The disclosed compound has agonist activity on the trace amine-associated receptor TAAR1 receptor, and has a mechanism of action that is different from existing therapeutic drugs for psychiatric disorders, thus providing a new option for drug treatment for various psychiatric disorders. That is, the disclosed compounds are effective in treating mental disorders. The disclosed compounds are also effective on central nervous system diseases.

Psychiatric diseases or central nervous system diseases for which efficacy is expected include, for example, International Classification of Diseases, 10th edition (ICD-10), F00-F09: organic mental disorders including symptomatic, F10-F19: mental and behavioral disorders due to psychoactive substance use, F20-F29: Schizophrenia, schizophrenia-type disorders and delusional disorders, F30-F39: Mood [emotional] disorders, F40-F48: Neurotic disorders, stress-related disorders and Somatoform disorders, F51: Nonorganic sleep disorders, F52: Sexual dysfunction, not due to organic disorders or diseases, F84: Pervasive developmental disorders, F90-F98: Behavioral and emotional disorders that usually begin in childhood and adolescence, G20-G26: extrapyramidal disorders and abnormal movements, G30-G32: other degenerative diseases of the nervous system, G47: sleep disorders, and the like.

F00-F09: Specific examples of organic mental disorders, including symptomatic ones, include dementia caused by Alzheimer's disease, vascular dementia, dementia with Lewy bodies, dementia caused by Parkinson's disease, mental illness associated with diseases such as brain damage, other mental disorders due to brain dysfunction and physical illness, and the like.

F10-F19: Specific examples of mental and behavioral disorders caused by the use of psychoactive substances include delirium tremens, psychotic disorders, amnestic syndromes, etc. caused by the use of various substances.

F20-F29: Specific examples of schizophrenia, schizophrenia-type disorder, and delusional disorder include paranoid schizophrenia, simple schizophrenia, delusional disorder, and the like.

F30-F39: Specific examples of mood [emotional] disorders include manic episodes, bipolar affective disorder, depressive episodes, and the like.

F40-F48: Specific examples of neurotic disorders, stress-related disorders, and somatoform disorders include phobic anxiety disorders, obsessive-compulsive disorders, somatoform disorders, and the like.

F51: Specific examples of nonorganic sleep disorders include nonorganic insomnia, somnambulism, nightmares, and the like.

F52: Specific examples of sexual dysfunction, which are not caused by organic disorders or diseases, include lack of sexual desire, loss of sexual desire, unspecified sexual dysfunction, and the like.

F84: Specific examples of pervasive developmental disorders include autism, mental retardation, and hyperactivity disorder associated with stereotypic movements, and the like.

F90-F98: Specific examples of hyperactivity disorders, behavioral and emotional disorders that commonly occur in childhood and adolescence include, for example, hyperactivity disorder, conduct disorder, mixed conduct and emotional disorder, and the like.

G20-G26: Specific examples of extrapyramidal disorders and abnormal movements include Parkinson's disease, secondary parkinsonism, dyskinesia, spinocerebellar degeneration, and the like.

G30-G32: Specific examples of other degenerative diseases of the nervous system include Alzheimer's disease, frontotemporal lobar dementia, frontotemporal lobar degeneration, Lewy body dementia, senile brain degeneration, progressive supranuclear palsy, and the like.

G47: Specific examples of sleep disorders include disorders of sleep induction and maintenance [insomnia], sleep/wake schedule disorders, narcolepsy, cataplexy, and the like.

The disclosed compounds are also useful to treat or prevent recurrence of various symptoms associated with these diseases (psychotic symptoms, restlessness, aggression, easy stimulability and irritability, sleep disorders, depressive symptoms, anxiety symptoms, cognitive dysfunction, etc.).

Preferable examples of the psychiatric diseases or central nervous system diseases for which efficacy is expected include schizophrenia, positive symptoms of schizophrenia, negative symptoms of schizophrenia, bipolar disorder with psychotic features, depressive disorders with psychotic features, psychotic symptoms associated with dementia, psychotic symptoms associated with Alzheimer's disease, psychotic symptoms associated with Lewy body dementia, psychotic symptoms associated with Parkinson's disease dementia, psychotic symptoms associated with Parkinson's disease, or irritation, agitation, or aggression associated with Alzheimer's disease, more preferably schizophrenia, psychotic symptoms associated with dementia, psychotic symptoms associated with Alzheimer's disease, psychotic symptoms associated with Lewy body dementia, or irritation, agitation, or aggression associated with Alzheimer's disease.

The disclosed compound exhibits agonist activity on the trace amine-associated receptor TAAR1 receptor (Test Example 1). In a preferable embodiment of the disclosed compound, the hERG channel inhibitory activity, which is an indicator of arrhythmia caused by QT prolongation, is weak (Test Example 3), so it can be expected that the effect on the cardiovascular system is small. In other words, there is a discrepancy between the concentration at which pharmacological effects occur and the concentration at which side effects occur.

The disclosed compounds can be administered orally or parenterally. When administered orally, it can be administered in commonly used dosage forms. Parenterally, it can be administered in the form of topical preparations, injections, transdermal preparations, nasal preparations and the like. Examples of oral or rectal preparations include capsules, tablets, pills, powders, cachets, suppositories, and liquid preparations. Examples of injections include sterile solutions or suspensions. Examples of topical preparations include creams, ointments, lotions, and transdermal preparations (common patches and matrix preparations).

The above dosage forms are formulated with pharmaceutically acceptable excipients and additives in a conventional manner. Pharmaceutically acceptable excipients and additives include carriers, binders, fragrances, buffers, thickeners, colorants, stabilizers, emulsifiers, dispersants, suspending agents, preservatives and the like.

Examples of the pharmaceutically acceptable carriers include magnesium carbonate, magnesium stearate, talc, sugar, lactose, pectin, dextrin, starch, gelatin, tragacanth, methylcellulose, sodium carboxymethylcellulose, low melting wax, cocoa butter, and the like. Capsules can be formulated by placing a disclosed compound together with a pharmaceutically acceptable carrier. The disclosed compounds can be mixed with pharmaceutically acceptable excipients or placed into capsules without excipients. Cachets can also be produced in a similar manner.

Examples of liquid preparations for injection include solutions, suspensions, emulsions, and the like. Examples thereof include an aqueous solution, a water-propylene glycol solution, and the like. Liquid preparations can also be prepared in the form of solutions of polyethylene glycol or/and propylene glycol which may also contain water. A solution suitable for oral administration can be prepared by adding a disclosed compound to water, and optionally adding colorants, flavors, stabilizers, sweeteners, solubilizers, thickeners and the like. Solutions suitable for oral administration can also be prepared by adding the disclosed compound to water together with a dispersant and making it viscous. Examples of the thickener include pharmaceutically acceptable natural or synthetic gums, resins, methylcellulose, sodium carboxymethylcellulose, or known suspending agents, and the like.

Although the dose varies depending on the individual compound and the patient's disease, age, weight, sex, symptoms, administration route, etc., the disclosed compound is usually administered at a dose of 0.1 to 1000 mg, preferably 1 to 300 mg/day, once a day or divided into 2 or 3 doses, for an adult (body weight 50 kg). It can also be administered once every few days to every few weeks.

The disclosed compounds can be used in combination with other drugs for the purpose of enhancing their effects and/or reducing their side effects. Hereinafter, a drug that can be used in combination with the disclosed compound will be abbreviated as a concomitant drug.

Specific examples of concomitant drugs include antidepressants, anxiolytics, schizophrenia drugs, dopamine replacement drugs, dopamine receptor agonists, Parkinson's disease drugs, antiepileptic drugs, analgesics, hormonal preparations, migraine medications, beta-adrenergic receptor antagonists, dementia drugs, mood disorder drugs, antiemetics, sleep-inducing drugs, anticonvulsants, and the like. Preferably, the concomitant drug includes an anxiolytic drug such as a selective serotonin reuptake inhibitor and the like.

The administration period of the presently disclosed compound and the concomitant drug is not limited, and they may be administered to the subject at the same time or at different times. It may also be a combination of the disclosed compound and a concomitant drug. The dosage of the concomitant drug can be appropriately selected based on the clinically used dosage. Further, the compounding ratio of the disclosed compound and the concomitant drug can be appropriately selected depending on the subject of administration, administration route, target disease, symptoms, combination, etc. For example, when the subject to be administered is a human, 0.01 to 100 parts by weight of the concomitant drug may be used per 1 part by weight of the disclosed compound. In addition, for the purpose of suppressing side effects, it can be used in combination with drugs (concomitant drugs) such as antiemetics, sleep-inducing drugs, anticonvulsants, and the like.

EXAMPLES

The present disclosure is explained in more detail below by referring to Reference Examples, Examples and Experimental Examples, but it is not limited to the following Reference Examples, Examples and Experimental Examples, including those described above. The scope of the present disclosure is therefore not limited to the embodiments specifically described herein nor to Examples, but only by the claims. The compound names given in the following Reference Examples and Examples are not always based on IUPAC nomenclature. The compounds were identified using proton nuclear magnetic resonance absorption spectroscopy ($^1$H-NMR), LC-MS and the like. LC-MS was measured under various conditions shown in the following table. Retention time (R.T.) means the time at which the mass spectral peak appeared in the LC-MS measurement.

TABLE 1

| | |
|---|---|
| Analytical apparatus | Shimadzu LCMS-2020 |
| Column | Phenomenex Kinetex 1.7 μm C18 (50 mm × 2.10 mm) |
| Eluent | solution A: 0.05% TFA/H$_2$O, solution B: MeCN |
| Gradient condition | 0.0-1.70 min (linear gradient from B 10% to 99%); 1.70-1.90 min (B 99%) 1.90-3.00 min (B 10%) |
| Flow rate | 0.5 mL/min |
| Wavelength (UV) | 220 nm |
| Column temperature | 40° C. |

The following abbreviations may be used herein.
Me: methyl
Et: ethyl
DMF: N, N-dimethylformamide
THF: tetrahydrofuran
tert-: tertiary
TBS: tert-butyldimethylsilyl
CDCl$_3$: deuterochloroform
DMSO-D$_6$: deuterodimethyl sulfoxide
CD$_3$OD: deuteromethanol Proton nuclear magnetic resonance spectra were measured with FT-NMR spectrometer (400 MHz, JEOL). Chemical shifts were shown in δ value (ppm). Symbols used in NMR mean the following; s is singlet, d is doublet, dd is double doublet, dt is double triplet, t is triplet, q is quartet, m is multiplet, br is broad, brs is broad singlet, and J is the coupling constant.

Example 1 rac-1-[(3R,4S)-3-methyl-3,4-dihydro-2H-pyrano[3,2-b]pyridin-4-yl]methanamine dihydrochloride

[Chemical Formula 11]

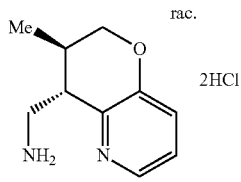

To a mixture of the compound (461 mg) of Reference Example 1-1, methanol (4.4 mL) and water (2.2 mL) was added sodium hydroxide (235 mg) at room temperature. After stirring at 60° C. for 5 hr, 3 mol/L hydrochloric acid was added to the aqueous layer until the layer reached pH5. The reaction solution was concentrated, and the concentrated residue was dissolved in methanol. The insoluble material was filtered off, and the filtrate was concentrated.

To a toluene solution (28 mL) of the obtained concentrated residue (406 mg) were added triethylamine (0.819 mL) and diphenylphosphoryl azide (0.842 mL) at room temperature. After stirring at room temperature for 30 min, the reaction solution was heated to 100° C. After stirring at 100° C. for 1 hr, the reaction solution was concentrated. To a mixture of the concentrated residue and tetrahydrofuran (20 mL) was added 5 mol/L aqueous sodium hydroxide solution (6.66 mL) under ice-cooling. After stirring at room temperature for 3 hr, to the reaction mixture was added di-tert-butyl dicarbonate (1.28 g). After stirring at room temperature for 15 hr, to the reaction mixture was added water (20 mL), the reaction mixture was subjected to extraction with chloroform (20 mL×three times), and the organic layer was dried over anhydrous magnesium sulfate, filtered, and concentrated. The concentrated residue was separated and purified by silica gel column chromatography (hexane/ethyl acetate).

To a mixture of the obtained purified product (31 mg) and ethyl acetate (1.0 mL) was added 4 mol/L hydrogen chloride-ethyl acetate (1.0 mL), and the mixture was stirred at room temperature for 2 hr. Then, the precipitated solid was collected by filtration, washed with diethyl ether (1.0 mL), and dried under reduced pressure to give the title compound (26 mg).

$^1$H-NMR (400 MHz, CD$_3$OD)
δ:8.31 (1H, dd, J=5.5, 1.2 Hz), 7.74 (1H, dd, J=8.6, 1.2 Hz), 7.65 (1H, dd, J=8.6, 5.5 Hz), 4.36 (1H, dd, J=11.0, 3.1 Hz), 4.21 (1H, dd, J=11.0, 6.7 Hz), 3.72-3.66 (1H, m), 3.48-3.36 (2H, m), 2.55-2.45 (1H, m), 1.12 (3H, d, J=7.3 Hz).

Example 2 rac-1-[(3S,4S)-3-methyl-3,4-dihydro-2H-pyrano[3,2-b]pyridin-4-yl]methanamine dihydrochloride

[Chemical Formula 12]

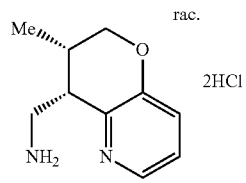

By the same method as in Example 1, the title compound was obtained from the compound of Reference Example 1-2.

$^1$H-NMR (400 MHz, CD$_3$OD)
δ:8.46 (1H, dd, J=5.5, 1.2 Hz), 8.00 (1H, dd, J=7.9, 1.2 Hz), 7.85 (1H, dd, J=7.9, 5.5 Hz), 4.40 (1H, dd, J=11.6, 2.4 Hz), 4.27 (1H, dd, J=11.6, 3.7 Hz), 3.53-3.43 (3H, m), 2.50-2.40 (1H, m), 1.15 (3H, d, J=6.7 Hz).

Example 3 rel-1-[(3R,4R)-3-methyl-3,4-dihydro-2H-pyrano[3,2-b]pyridin-4-yl]methanamine dihydrochloride

[Chemical Formula 13]

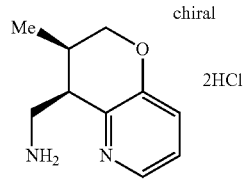

The compound of Reference Example 5 was optically resolved by chiral HPLC to give a compound having the first peak. To an ethyl acetate solution (1.0 mL) of this compound (48.0 mg) was added 4 mol/L hydrogen chloride-ethyl acetate (0.43 mL) at room temperature, and the mixture was stirred at room temperature for 2 hr. Then, the precipitated solid was collected by filtration, and dried under reduced pressure to give the title compound.

[Chiral HPLC Condition]

Column: IC 4.6 cm×25 cm

Solvent: Hexane (90%)—IPA (10%) including diethylamine (0.1%)

Flow rate: 1.0 mL/min

Retention time=3.8 min (first peak)

$[\alpha]_D^{22.4}$ −10.4 (c0.1, MeOH)

$^1$H-NMR (400 MHz, DMSO-D$_6$)

δ:8.21 (3H, brs), 8.21 (1H, dd, J=4.6, 1.5 Hz), 7.40 (1H, brd, J=7.9 Hz), 7.3 (1H, dd, J=7.9, 4.6 Hz), 4.20 (1H, dd, J=11.6, 3.0 Hz), 3.93 (1H, dd, J=11.3, 7.0 Hz), 3.33-3.27 (1H, m), 3.18-3.11 (1H, m), 2.98-2.92 (1H, m), 2.23-2.15 (1H, m), 1.01 (3H, d, J=6.7 Hz).

Example 4 rel-1-[(3S,4S)-3-methyl-3,4-dihydro-2H-pyrano[3,2-b]pyridin-4-yl]methanamine dihydrochloride

[Chemical Formula 14]

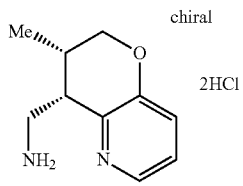

The compound of Reference Example 5 was optically resolved by chiral HPLC to give a compound having the second peak. To an ethyl acetate solution (1.0 mL) of this compound (44.8 mg) was added 4 mol/L hydrogen chloride-ethyl acetate (0.40 mL) at room temperature, and the mixture was stirred at room temperature for 2 hr. Then, the precipitated solid was collected by filtration, and dried under reduced pressure to give the title compound.

[Chiral HPLC Condition]

Column: IC 4.6 cm×25 cm

Solvent: Hexane (90%)—IPA (10%) including diethylamine (0.1%)

Flow rate: 1.0 mL/min

Retention time=4.5 min (second peak)

$[\alpha]_D^{22.7}$ +14.4 (c0.1, MeOH)

$^1$H-NMR (400 MHz, DMSO-D$_6$)

δ:8.21 (3H, brs), 8.21 (1H, dd, J=4.6, 1.5 Hz), 7.40 (1H, brd, J=7.9 Hz), 7.3 (1H, dd, J=7.9, 4.6 Hz), 4.20 (1H, dd, J=11.6, 3.0 Hz), 3.93 (1H, dd, J=11.3, 7.0 Hz), 3.33-3.27 (1H, m), 3.18-3.11 (1H, m), 2.98-2.92 (1H, m), 2.23-2.15 (1H, m), 1.01 (3H, d, J=6.7 Hz).

Example 5

N-methyl-1-[(2R,4S)-2-methyl-3,4-dihydro-2H-pyrano[3,2-b]pyridin-4-yl]methanamine dihydrochloride

[Chemical Formula 15]

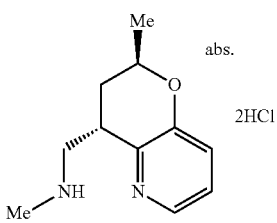 [SMILES: CNC[C@@H]1C[C@@H](C)Oc2cccnc21]

To a mixture of the compound (203 mg, 0.728 mmol) of Reference Example 6-1 and tetrahydrofuran (10.0 mL) was added 55% sodium hydride (95.0 mg) under ice-cooling. After stirring under ice-cooling for 30 min, iodomethane (0.453 mL, 7.28 mmol) was added thereto. After stirring at room temperature for 3 hr, saturated aqueous ammonium chloride solution (10 mL) was added thereto, the mixture was subjected to extraction with ethyl acetate (10 mL×twice), and the organic layer was dried over anhydrous magnesium sulfate, filtered, and concentrated. The concentrated residue was separated and purified by silica gel column chromatography (hexane/ethyl acetate), followed by concentration.

To a mixture of the obtained product (192 mg) and ethyl acetate (3.0 mL) was added 4 mol/L hydrogen chloride-ethyl acetate (3.0 mL) under ice-cooling, and the mixture was stirred at room temperature for 2 hr. Then, the precipitated solid was collected by filtration, and dried under reduced pressure to give the title compound (142 mg).

$^1$H-NMR (400 MHz, DMSO-D$_6$)

δ:9.56 (1H, brs), 9.13 (1H, brs), 8.29 (1H, d, J=4.9 Hz), 7.62 (1H, d, J=7.9H z), 7.52 (1H, dd, J=7.9, 4.9 Hz), 4.41-4.35 (1H, m), 3.56-3.54 (1H, m), 3.40-3.29 (2H, m), 2.61 (3H, t, J=4.9 Hz), 2.45-2.35 (1H, m), 1.88-1.80 (1H, m), 1.38 (3H, d, J=6.1 Hz).

Examples 6 to 7

According to the method described in Example 5, the compounds of Examples 6 to 7 were obtained from the corresponding compounds of Reference Examples, respectively.

TABLE 2

| Ex. No. | Chemical Structure | Instrumental analysis data |
|---|---|---|
| 6 | Me (structure) 2HCl | $^1$H-NMR (400 MHz, DMSO-D$_6$) δ: 9.14 (1H, brs), 9.02 (1H, brs), 8.12 (1H, t, J = 3.0 Hz), 7.28 (2H, d, J = 2.4 Hz), 4.36-4.28 (1H, m), 3.52-3.39 (2H, m), 3.18-3.09 (1H, m), 2.63 (3H, t, J = 5.2 Hz), 2.24 (1H, dd, J = 12.8, 4.9 Hz), 1.62-1, 52 (1H, m) 1.37 (3H, d, J = 6.1 Hz). |

TABLE 2-continued

| Ex. No. | Chemical Structure | Instrumental analysis data |
|---|---|---|
| 7 | Me, rac. (chromanopyridine with CH2NHMe), 2HCl | $^1$H-NMR (400 MHz, DMSO-D$_6$) δ: 9.18 (2H, brs), 8.27-8.11 (1H, m), 7.51-7.22 (2H, m), 4.42-4.27 (1H, m), 3.73-3.17 (3H, m), 2.67-2.59 (3H, m), 2.36-2.15 (1H, m), 1.94-1.83 (1H, m), 1.40-1.33 (3H, m). |

Example 8

1-[(2R,3S)-6-fluoro-2-methyl-2,3-dihydrofuro[3,2-b]pyridin-3-yl]methanamine dihydrochloride

[Chemical Formula 16]

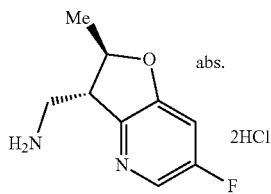 [SMILES: Cc1cnc2c(c1)O[C@H](C)[C@H]2CN]

To a mixture of the compound (98 mg, 3.47 mmol) of Reference Example 13 and 2-propanol (3.5 mL) was added 4 mol/L hydrogen chloride-cyclopentyl methyl ether (2 mL), and the mixture was stirred at room temperature for 2 hr. The reaction solution was concentrated, and the obtained solid was recrystallized from 2-propanol to give the title compound (39.7 mg).

[α]$_D^{25.8}$ +46.8 (c0.005, MeOH)

$^1$H-NMR (400 MHz, DMSO-D$_6$) δ:8.12-8.02 (4H, m), 7.30-7.25 (1H, m), 5.01-4.95 (1H, m), 3.41-3.31 (1H, m), 3.22-3.08 (2H, m), 1.46 (3H, d, J=6.7 Hz).

Examples 9 to 25

According to the method described in Example 8, the compounds of Examples 9 to 25 were obtained from the corresponding compounds of Reference Examples, respectively.

TABLE 3

| Ex. No. | Chemical Structure | Instrumental analysis data |
|---|---|---|
| 9 | rac. (thiochromanopyridine with CH2NH2), 2HCl | $^1$H-NMR (400 MHz, DMSO-D$_6$) δ: 8.32-8.31 (1H, m), 8.23 (3H, s), 7.74-7.72 (1H, m), 7.30-7.29 (1H, m), 3.31-3.28 (2H, m), 3.18-3.08 (3H, m), 2.34-2.25 (1H, m), 2.12-2.11 (1H, m). |
| 10 | rac. (dihydrothienopyridine with CH2NH2) | $^1$H-NMR (400 MHz, CDCl$_3$) δ: 8.13 (1H, dd, J = 4.9, 1.5 Hz), 7.40 (1H, dd, J = 7.6, 1.5 Hz), 6.95 (1H, dd, J = 7.6, 4.9 Hz), 3.49-3.40 (2H, m), 3.25-3.18 (1H, m), 3.13-3.02 (2H, m), |
| 11 | rac. (dihydrothienopyridine-Me with CH2NH2), 2HCl | $^1$H-NMR (400 MHz, DMSO-D$_6$) δ: 8.42 (3H, s), 7.82 (1H, d, J = 7.9 Hz), 7.25 (1H, d, J = 7.9 Hz), 3.96-3.88 (1H, m), 3.64 (1H, dd, J = 11.0, 8.2 Hz), 3.45 (1N, dd, J = 11.0, 7.9 Hz), 3.41-3.31 (1H, m), 3.18-3.08(1H, m), 2.51 (3H, s). |
| 12 | rac. (thiochromanopyridine-Me with CH2NH2), 2HCl | $^1$H-NMR (400 MHz, DMSO-D$_6$) δ: 8.20 (3H, s), 7.69 (1H, brs), 7.25 (1H, brs), 3.43-3.20 (2H, m), 3.17-3.02 (3H, m), 2.51 (3H, s), 2.21-2.12 (2H, m), |
| 13 | Me rac. (thiochromanopyridine-Me with CH2NH2) | $^1$H-NMR (400 MHz, CDCl$_3$) δ: 8.18 (1H, brs), 7.30 (1H, dd, J = 7.9, 1.2 Hz), 6.91 (1H, dd, J = 7.9, 4.9 Hz), 3, 49-3.40 (1H, m), 3.25-3.10 (2H, brs), 2.94-2.85 (1H, m), 2.27 (1H, ddd, J = 13, 4, 4.3, 3.1 Hz), 1.75 (1H, ddd, J = 13.4, 11.9, 11.9 Hz), 1.31 (3H, d, J = 6.7 Hz). |
| 14 | Me rac. (thiochromanopyridine-Me with CH2NH2), 2HCl | $^1$H-NMR (400 MHz, DMSO-D$_6$) δ: 8.30 (1H, d, J = 4.9 Hz), 8.15 (3H, s), 7.66 (1H, d, J = 7.9 Hz), 7.26 (1H, dd, J = 7.9, 4.9 Hz), 3.57-3.49 (1H, m), 3.37-3.29 (1H, m), 3.25-3.19 (1H, m), 3.16-3.09 (1H, m), 2.25 (1H, ddd, J = 14.0, 5.5, 3, 7 Hz), 1.93 (1H, ddd, J = 14.0.9.8, 4.9 Hz), 1.35 (3H d, J = 6.7 Hz). |
| 15 | Me, rac. (dihydrothienopyridine-Me with CH2NH2), 2HCl | $^1$H-NMR (400 MHz, CD$_3$OD) δ: 8.34 (1H, d, J = 4.9 Hz), 7.94 (1H, d, J = 7, 9 Hz), 7.47-7.45 (1H, m), 3.96-3.89 (1H, m), 3.63-3.61 (1H, m), 3.41-3.35 (2H, m), 1.56 (3H, d, J = 6.7 Hz). |
| 16 | Me, rac. (dihydrothienopyridine-Me with CH2NH2), 2HCl | $^1$H-NMR (400 MHz, CD$_3$OD) δ: 8.16-8.15 (1H, m), 7.60-7.58 (1H, m), 7.14-7.12 (1H, m), 4.07-4.00 (1H, m), 3.44-3.42 (1H, m), 3.27-3.25 (1H, m), 3.03-2.99 (1H, m), 1.31 (3H, d, J = 7.3 Hz). |

TABLE 3-continued

| Ex. No. | Chemical Structure | Instrumental analysis data |
|---|---|---|
| 17 | Me, abs. ...NH2...N...Me · 2HCl | 1H-NMR (400 MHz, DMSO-D6) δ: 8.23 (3H, brs), 7.26 (1H, brs), 7.18 (1H, d, J = 7.9 Hz), 4.25 (1H, ddd, J = 11.0, 6.1, 1.8 Hz), 3.44-3.32 (2H, m), 3.13-3.04 (1H, m), 2.46 (3H, s), 2.21 (1H, ddd, J = 13.4, 4.3, 1.8 Hz), 1.64-1.53 (1H, m), 1.35 (3H d, J = 6.1 Hz) |
| 18 | Me, abs. ...NH2...N...Me · 2HCl | 1H-NMR (400 MHz, DMSO-D6) δ: 8.27 (3H, brs), 7.53 (1H, brs), 7.37 (1H, brs). 4.37-4.26 (1H, m), 3.45-3.30 (2H, m), 3.18-3.05 (1H, m), 2.53 (3H, s), 2.21 (1H, brd, J = 14.6 Hz), 1.85-1.75 (1H, m), 1.36 (3H, d, J = 6, 1 Hz). |
| 19 | Me, abs. H2N...N · 2HCl | 1H-NMR (400 MHz, DMSO-D6) δ: 8.28 (3H, s), 8.09-8.08 (1H, m), 7.27 (2H, m), 4.95-4.94 (1H, m), 3.50-3.48 (1H, m), 3.24-3.19 (2H, m), 1.48 (3H, d, J = 6.7 Hz). |
| 20 | Me, abs. H2N...N · 2HCl | 1H-NMR (400 MHz, DMSO-D6) δ: 8.13-7.99 (3H, brs), 8.04 (1H, dd, J = 3.7, 2, 4 Hz), 7.23-7.20 (2H, m), 5.15 (1H, dq, J = 9.2, 6.1 Hz), 3.77 (1H, dd, J = 7.9, 7, 9 Hz), 3.24-3.17 (2H, m), 1.34 (3H, d, J = 6.1 Hz). |
| 21 | Me, Me, rac. H2N...N · 2HCl | 1H-NMR (400 MHz, DMSO-D6) δ: 8.35 (3H, brs), 8.09-8.08 (1H, m), 7.33-7.29 (2H, m), 4.71-4.70 (1H, m), 3.70-3.68 (1H, m), 3.23-3.16 (2H, m), 2.00-1.97 (1H, m), 0.99-0.92 (6H, m). |
| 22 | Me, rac. H2N...N · 2HCl | 1H-NMR (400 MHz, DMSO-D6) δ: 8.36-8.05 (4H, m), 7.35-7.25 (2H, m), 4.85-4.77 (1H, s), 3.59-3.55 (1H, m), 3.30-3.15 (2H, m), 1.85-1.70 (2H, m), 0.97 (3H, t, J = 6.7 Hz). |
| 23 | Me, Me, rac. H2N...N · 2HCl | 1H-NMR (400 MHz, CD3OD) δ: 8.14 (1H, dd, J = 5.2, 1.5 Hz), 7.43-7.35 (2H, m), 3.65 (1H, dd, J = 9.8, 5.5 Hz), 3.49-3.35 (2H, m), 1.63 (3H.s), 1.45 (3H, s), |
| 24 | rac. NH2...N · 2HCl (with phenyl) | 1H-NMR (400 MHz, DMSO-D6) δ: 8.37-8.16 (4H, m), 7.48-7.34 (7H, m), 5.30 (1H, d, J = 11.0 Hz), 3.65-3.43 (2H, m), 3.128-3.06 (1H, m), 2.06-1.96 (2H, m), |
| 25 | rac. NH2...N · 2HCl (with phenyl) | 1H-NMR (400 MHz, DMSO-D6) δ: 8.35-8.20 (4H, m), 7.57-7.48 (3H, m), 7.44-7.34 (4H, m), 5.40-5.34 (1H, m), 3.43-3.23 (3H, m), 2.43-2.27 (2H, m). |
| 26 | OH, rac. H2N...N · 2HCl | 1H-NMR (400 MHz, DMSO-D6) δ: 8.10-7.95 (4H, m), 7.21-7.18 (2H, m), 4.79-4.73 (1H, m), 3.76-3.61 (3H, m), 3.30-3.12 (2H, m). |

Example 27

1-[(2R,3S)-2-methyl-2,3-dihydrofuro[3,2-b]pyridin-3-yl]methanamine dihydrochloride

[Chemical Formula 17]

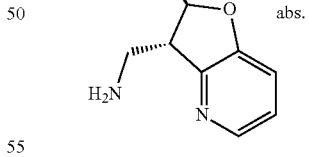

To a mixture of the compound (23.6 g, 79.0 mmol) of Reference Example 37 and methanol (158 mL) was added 10% palladium-carbon (8.00 g) under nitrogen atmosphere. After stirring under hydrogen atmosphere at room temperature for 5 hr, the mixture was filtered through Celite, and the filtrate was concentrated.

To a mixture of the concentrated residue and 2-propanol (158 mL) was added 4 mol/L hydrogen chloride-cyclopentyl methyl ether (43.5 mL, 174 mmol), and the mixture was stirred at room temperature for 15 min. The reaction solution was concentrated, and the obtained crude crystals were recrystallized from 2-propanol and methanol to give the title compound (9.57 g). $[\alpha]_D^{25.3}$ +37.4 (c0.01, MeOH)

$^1$H-NMR (400 MHz, DMSO-D$_6$) δ:8.54-8.33 (3H, s), 8.11 (1H, dd, J=4.6, 1.5 Hz), 7.37 (1H, dd, J=7.9, 1.5 Hz) 7.33 (1H, dd, J=7.9, 4.6 Hz), 5.03 (1H, dq, J=6.7, 6.1 Hz) 3.60-3.57 (1H, m) 3.32-3.29 (1H, m), 3.21-3.16 (1H, m), 1.47 (3H, d, J=6.1 Hz).

Examples 28 to 32

According to the method described in Example 27, the compounds of Examples 28 to 32 were obtained from the corresponding compounds of Reference Examples, respectively.

TABLE 4

| Ex. No. | Chemical Structure | Instrumental analysis data |
|---|---|---|
| 28 | 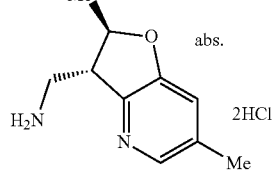 | $^1$H-NMR (400 MHz, DMSO-D$_6$) δ: 8.18 (3H, brs), 7.93 (1H, s), 7.12 (1H, s), 4.94-4.86 (1H, m), 3.44-3.36 (1H, m), 3.26-3.16 (1H, m), 3.16-3.07 (1H, m), 2, 26 (3H, s), 1.44 (3H, d, J = 6.1 Hz), |
| 29 | 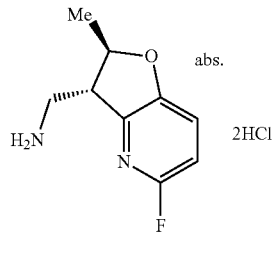 [SMILES: C[C@H]1Oc2ccc(F)nc2[C@@H]1CN] | $^1$H-NMR (400 MHz, DMSO-D$_6$) δ: 8.21 (3H, s), 7.39 (1H, dd, J = 8.8, 6.4 Hz), 6.97 (1H, brd, J = 8.8 Hz), 4, 97 (1H, dq, J = 6.4, 6.1 Hz), 3.45-3.39 (1H, m), 3.17 (1H, dd, J = 12.8, 5.5 Hz), 3.11 (1H, dd, J = 12.8, 7.2 Hz), 1.45 (3H, d, J = 6.1 Hz). |
| 30 | 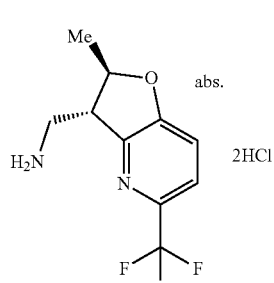 | $^1$H-NMR (400 MHz, DMSO-D$_6$) δ: 8.13 (3H, s), 7.71 (1H, d, J = 7.9 Hz), 7.39 (1H, d, J = 7.9 Hz), 5.07 (1H, dq, J = 6.7, 6.7 Hz), 3.54-3.48 (1H, m), 3.26 (1H, dd, J = 13.1, 4.9 Hz), 3.19 (1H, dd, J = 13.1, 8.8 Hz), 1.50 (3H, d, J = 6.7 Hz). |
| 31 | 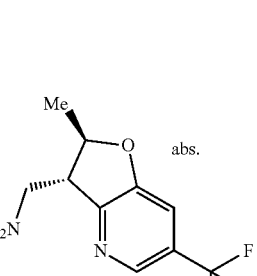 | $^1$H-NMR (400 MHz, DMSO-D$_6$) δ: 8.42 (1H, brs), 8.24 (3H, s), 7.62 (1H, d, J = 1.8 Hz), 5.04 (1H, dq, J = 6.1, 6.4 Hz), 3.57-3.50 (1H, m), 3.30-3.16 (2H, m), 1.50 (3H, d, J = 6.1 Hz). |
| 32 | 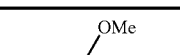 | $^1$H-NHR (400 MHz, CD$_3$OD) δ: 8.26 (1H, dd, J = 5.5, 1.2 Hz), 7.69-7.60 (2H, m) 5.06, (1H, dd, J = 11.0, 4.9 Hz), 4.11-4.03 (1H, m), 3.81-3.70 (2H, m), 3.58 (1H, dd, J = 13.4, 5.5 Hz), 3.47-3.39 (4H, m). |

Example 33 rac-1-[(5aS,9aR,10S)-6,7,8,9,9a,10-hexahydro-5aH-[1]benzpyrano[3,2-b]pyridine-10-yl]methanamine dihydrochloride

[Chemical Formula 18]

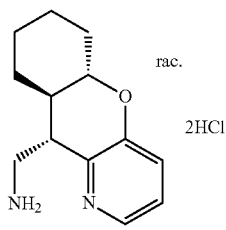

To a toluene solution (7.1 mL) of the compound (123 mg, 0.497 mmol) of Reference Example 50 were added triethylamine (0.208 mL, 1.49 mmol) and diphenylphosphoryl azide (0.214 mL, 0.995 mmol), and the mixture was stirred at room temperature for 30 min. After stirring at 90° C. for 1 hr, to the reaction mixture was added dropwise 5 mol/L aqueous sodium hydroxide solution (1.69 mL) under ice-cooling, and the mixture was stirred at room temperature for 2 hr. To the reaction mixture was added 6 mol/L hydrochloric acid until the mixture reached pH2, and the mixture was concentrated. To the concentrated residue was added methanol, the insoluble material was removed by filtration, and the filtrate was concentrated. To a chloroform solution (10 mL) of the residue were added triethylamine (0.208 mL, 1.49 mmol) and di-tert-butyl dicarbonate (0.346 mL, 1.49 mmol). After stirring at room temperature for 1 hr, to the reaction mixture was added water (30 mL), the mixture was subjected to extraction with chloroform (30 mL×twice), and the organic layer was dried over anhydrous sodium sulfate, filtered, and concentrated. The concentrated residue was separated and purified by silica gel column chromatography (hexane/ethyl acetate). To an ethyl acetate solution (1.0 mL) of the obtained product was added 4 mol/L hydrogen chloride-ethyl acetate (1.0 mL), and the mixture was stirred at room temperature for 2 hr. The reaction mixture was concentrated, and the residue was separated and purified by amino silica gel column chromatography (chloroform/methanol) to give the title compound (13 mg).

$^1$H-NMR (400 MHz, CDCl$_3$)

δ:8.06 (1H, dd, J=4.6, 1.5 Hz), 7.03 (1H, dd, J=8.6, 1.5 Hz), 6.99 (1H, dd, J=8.6, 4.6 Hz), 3.62 (1H, dt, J=10.5, 4.5 Hz), 3.50 (1H, dd, J=12.5, 3.1 Hz), 2.90 (1H, dd, J=12.5, 6.4 Hz), 2.86 (2H, brs), 2.68 (1H, ddd, J=11.0, 6.1, 3.1H z), 2.17-2.08 (2H, m), 1.84-1.79 (1H, m), 1.74-1.68 (1H, m), 1.59 (1H, ddd, J=10.4, 10.4, 3.1 Hz), 1.47-1.18 (4H, m), 1.02 (1H, ddd, J=12.5, 12.5, 3.7 Hz).

Example 34

1-[(2R,3S)-2,7-dimethyl-2,3-dihydrofuro[3,2-b]pyridin-3-yl]methanamine dihydrochloride

[Chemical Formula 19]

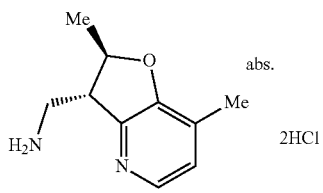

By the same method as in Example 33, the title compound was obtained from the compound of Reference Example 51.

$^1$H-NMR (400 MHz, DMSO-D$_6$)

δ:8.45 (3H, brs), 8.10 (1H, d, J=5.5 Hz), 7.37 (1H, d, J=5.5 Hz), 5.10 (1H, dq, J=6.7, 6.7 Hz), 3.74-3.67 (1H, m), 3.43-3.37 (1H, m), 3.27-3.18 (1H, m), 2.25 (3H, s), 1.49 (3H, d, J=6.7 Hz).

Example 35

1-[(2R,3S)-2,5-dimethyl-2,3-dihydrofuro[3,2-b]pyridin-3-yl]methanamine

[Chemical Formula 20]

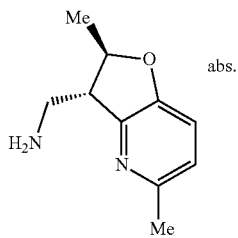

To an ethyl acetate solution (1.0 mL) of the compound (24.4 mg, 0.0878 mmol) of Reference Example 52 was added 4 mol/L hydrogen chloride-ethyl acetate (1.0 mL). After stirring at room temperature for 2 hr, the precipitated solid was collected by filtration, and dried. To a chloroform suspension (1.0 mL) of the obtained solid (20 mg) were added triethylamine (0.039 mL, 0.279 mmol) and trifluoroacetic anhydride (0.013 mL, 0.096 mmol), and the mixture was stirred at room temperature for 2 hr. To the reaction mixture was added water (30 mL), the mixture was subjected to extraction with chloroform (30 mL×twice), and the organic layer was dried over anhydrous sodium sulfate, filtered, and concentrated. The residue was separated and purified by silica gel column chromatography (hexane/ethyl acetate). To a mixture of the obtained product, methanol (0.9 mL) and water (0.1 mL) was added potassium carbonate (55.0 mg, 0.398 mmol), and the mixture was stirred at 50° C. for 2 hr. To the reaction mixture was added water (30 mL), the mixture was subjected to extraction with chloroform (30 mL×twice), and the organic layer was dried over anhydrous sodium sulfate, filtered, and concentrated. The residue was separated and purified by amino silica gel column chromatography (chloroform/methanol) to give the title compound (8.2 mg).

$^1$H-NMR (400 MHz, CDCl$_3$)

δ:6.85 (1H, d, J=8.6 Hz), 6.81 (1H, d, J=8.6 Hz), 4.65-4.58 (1H, dq, J=6.1, 6.1 Hz), 3.03-2.99 (3H, m), 2.40 (3H, s), 2.10 (2H, s), 1.43 (3H, d, J=6.1 Hz).

Example 36 rac-1-[(2R,3R)-2-methyl-2,3-dihydrofuro[3,2-b]pyridin-3-yl]methanamine dihydrochloride

[Chemical Formula 21]

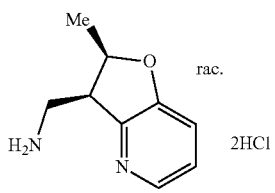

To a toluene solution (57.3 mL) of the diastereomeric mixture (10:1, 1.66 g, 8.59 mmol) of Reference Example 38 were added triethylamine (3.59 mL, 25.8 mmol) and diphenylphosphoryl azide (3.69 mL, 17.2 mmol) at room temperature, and the mixture was stirred at room temperature for 30 min. After stirring at 90° C. for 1 hr, to the reaction mixture was added dropwise 5 mol/L aqueous sodium hydroxide solution (29.2 mL) under ice-cooling. The reaction mixture was warmed to room temperature over 2 hr, and 6 mol/L hydrochloric acid was added to the aqueous layer until the layer reached pH5. The reaction mixture was concentrated, and the concentrated residue was dissolved in methanol. The insoluble material was filtered off, and the filtrate was concentrated. Then, to a mixture of the concentrated residue and chloroform (100 mL) were added triethylamine (3.59 mL, 25.8 mmol) and di-tert-butyl dicarbonate (5.63 g, 25.8 mmol). After stirring at room temperature for 1 hr, to the reaction mixture was added water (100 mL), the mixture was subjected to extraction with chloroform (50 mL×twice), and the organic layer was dried over anhydrous magnesium sulfate, filtered, and concentrated. The concentrated residue was separated and purified by silica gel column chromatography (hexane/ethyl acetate). A part (100 mg) of the obtained product was further separated and purified by reverse-phase silica gel column chromatography (water/acetonitrile/trifluoroacetic acid) to give a product.

To a mixture of the obtained product (10 mg) and ethyl acetate (1.0 mL) was added 4 mol/L hydrogen chloride-ethyl acetate (0.1 mL), and the mixture was stirred at room temperature for 1 hr. Then, the precipitated solid was collected by filtration, and dried under reduced pressure to give the title compound (7.0 mg).

$^1$H-NMR (400 MHz, DMSO-D$_6$) δ:8.13-7.99 (3H, brs), 8.04 (1H, dd, J=3.7, 2.4 Hz), 7.23-7.20 (2H, m), 5.15 (1H, dq, J=9.2, 6.1 Hz), 3.77 (1H, dd, J=7.9, 7.9 Hz), 3.24-3.17 (2H, m), 1.34 (3H, d, J=6.1 Hz).

Example 37

1-[(2R,3S)-6-chloro-2-methyl-2,3-dihydrofuro[3,2-b]pyridin-3-yl]methanamine dihydrochloride

[Chemical Formula 22]

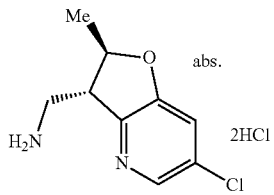

To a toluene solution (2.2 mL) of the compound (342 mg, 1.50 mmol) of Reference Example 53 were added triethylamine (0.314 mL, 2.25 mmol) and diphenylphosphoryl azide (0.388 mL, 1.80 mmol) at room temperature, and the mixture was stirred at room temperature for 30 min. After stirring at 90° C. for 1 hr, to the reaction mixture was added dropwise 5 mol/L aqueous sodium hydroxide solution (5.11 mL) under ice-cooling. The reaction mixture was warmed to room temperature over 2 hr, and 6 mol/L hydrochloric acid was added to the aqueous layer until the layer reached pH5. The reaction mixture was concentrated, and the concentrated residue was dissolved in methanol. The insoluble material was filtered off, and the filtrate was concentrated. Then, to a mixture of the concentrated residue and chloroform (2.2 mL) were added triethylamine (0.628 mL, 4.51 mmol) and di-tert-butyl dicarbonate (984 mg, 4.51 mmol). After stirring at room temperature for 1 hr, to the reaction mixture was added water (4.0 mL), the mixture was subjected to extraction with chloroform (4 mL×twice), and the organic layer was dried over anhydrous magnesium sulfate, filtered, and concentrated. The concentrated residue was separated and purified by silica gel column chromatography (hexane/ethyl acetate).

To a mixture of the obtained compound (219 mg) and 2-propanol (1.5 mL) was added 4 mol/L hydrogen chloride-cyclopentyl methyl ether (1.83 mL), and the mixture was stirred at room temperature for 1 hr. The reaction solution was concentrated, and the obtained crude crystals were recrystallized from 2-propanol and methanol to give the title compound (66 mg).

$^1$H-NMR (400 MHz, DMSO-D$_6$)
δ:8.14 (3H, brs), 8.08 (1H, d, J=1.8 Hz), 7.44 (1H, d, J=1.8 Hz), 4.97 (1H, dq, J=6.1, 6.1 Hz), 3.43-3.38 (1H, m), 3.23-3.11 (2H, m), 1.47 (3H, d, J=6.1 Hz).

Example 38

1-[(2R,3S)-5-chloro-2-methyl-2,3-dihydrofuro[3,2-b]pyridin-3-yl]methanamine dihydrochloride

[Chemical Formula 23]

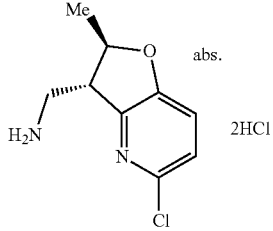

By the same method as in Example 37, the title compound was obtained from the compound of Reference Example 54.

$^1$H-NMR (400 MHz, DMSO-D$_6$) δ:8.11 (3H, brs), 7.29 (2H, s), 5.01-4.92 (1H, m), 3.47-3.39 (1H, m), 3.20 (1H, dd, J=13.1, 5.2 Hz), 3.14 (1H, dd, J=13.1, 8.2 Hz), 1. (3H, d, J=6.7 Hz).

Example 39 rel-1-[(4R)-3,4-dihydro-2H-thiopyrano[3,2-b]pyridin-4-yl]methanamine dihydrochloride

[Chemical Formula 24]

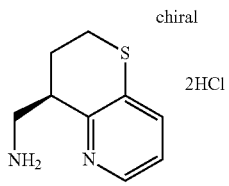

The compound of Reference Example 15 was optically resolved by chiral HPLC to give a compound having the first peak. To an ethyl acetate solution (1.0 mL) of this compound (20.0 mg, 0.0713 mmol) was added 4 mol/L hydrogen chloride-ethyl acetate (0.178 mL), and the mixture was stirred at room temperature for 2 hr. Then, the precipitated solid was collected by filtration, and dried under reduced pressure to give the title compound (12 mg).

[Chiral HPLC Condition]

Column: IC

Solvent: Hexane (90%)—IPA (10%) including diethylamine (0.1%)

Flow rate: 1.0 mL/min

Retention time=7.7 min (first peak)

[α]$_D^{24.0}$ −34.5 (c0.1, MeOH)

$^1$H-NMR (400 MHz, DMSO-D$_6$)
δ:8.27 (1H, dd, J=4.6, 1.5 Hz), 8.13 (3H, brs), 7.65 (1H, dd, J=7.9, 1.5 Hz), 7.24 (1H, dd, J=7.9, 4.6 Hz), 3.32-3.19 (2H, m), 3.16-3.07 (3H, m), 2.32-2.22 (1H, m), 2.09-2.00 (1H, m).

Example 40 rel-1-[(4S)-3,4-dihydro-2H-thiopyrano[3,2-b]pyridin-4-yl]methanamine dihydrochloride

[Chemical Formula 25]

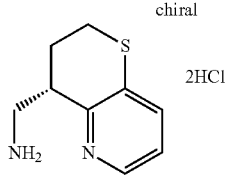

The compound of Reference Example 15 was optically resolved by chiral HPLC to give a compound having the second peak. Then, by the same method as in Example 39, the title compound was obtained.
[Chiral HPLC Condition]
Column: IC
Solvent: Hexane (90%)—IPA (10%) including diethylamine (0.1%)
Flow rate: 1.0 mL/min
Retention time=9.2 min (second peak)
$[\alpha]_D^{243}$+22.6 (c0.1, MeOH)
$^1$H-NMR (400 MHz, DMSO-D$_6$)
δ:8.27 (1H, dd, J=4.6, 1.5 Hz), 8.13 (3H, brs), 7.65 (1H, dd, J=7.9, 1.5 Hz), 7.24 (1H, dd, J=7.9, 4.6 Hz), 3.32-3.19 (2H, m), 3.16-3.07 (3H, m), 2.32-2.22 (1H, m), 2.09-2.00 (1H, m).

Example 41 rel-1-[(3R)-2,3-dihydrothieno[3,2-b]pyridin-3-yl]methanamine dihydrochloride

[Chemical Formula 26]

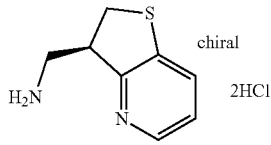

The compound of Reference Example 18 was optically resolved by chiral HPLC to give a compound having the first peak. Then, by the same method as in Example 39, the title compound was obtained.
[Chiral HPLC Condition]
Column: IC
Solvent: Hexane (90%)—IPA (10%)
Flow rate: 1.0 mL/min
Retention time=7.67 min (first peak)
$^1$H-NMR (400 MHz, DMSO-D$_6$) δ:8.32 (3H, brs), 8.24-8.24 (1H, m), 7.80-7.78 (1H, m), 7.26-7.24 (1H, m), 3.84-3.81 (1H, m), 3.64-3.57 (1H, m), 3.40-3.34 (2H, m), 3.17-3.10 (1H, m).

Example 42 rel-1-[(3S)-2,3-dihydrothieno[3,2-b]pyridin-3-yl]methanamine dihydrochloride

[Chemical Formula 27]

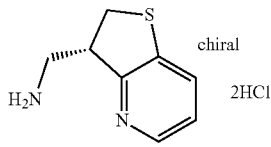

The compound of Reference Example 18 was optically resolved by chiral HPLC to give a compound having the second peak. Then, by the same method as in Example 39, the title compound was obtained.
[Chiral HPLC Condition]
Column: IC
Solvent: Hexane (90%)—IPA (10%)
Flow rate: 1.0 mL/min
Retention time=9.19 min (second peak)
$^1$H-NMR (400 MHz, DMSO-D$_6$) δ:8.24-8.23 (1H, m), 8.21 (3H, brs), 7.76 (1H, d, J=7.3 Hz), 7.24-7.22 (1H, m), 3.80-3.78 (1H, m), 3.62-3.59 (1H, m), 3.38-3.35 (2H, m), 3.17-3.11 (1H, m).

Example 43 rel-1-[(2R,3S)-2-ethyl-2,3-dihydrofuro[3,2-b]pyridin-3-yl]methanamine dihydrochloride

[Chemical Formula 28]

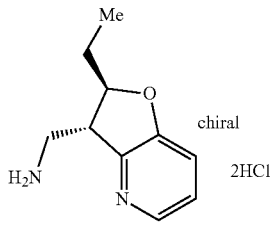

The compound of Reference Example 33 was optically resolved by chiral HPLC to give a compound having the first peak. Then, by the same method as in Example 39, the title compound was obtained.
[Chiral HPLC Condition]
Column: IC
Solvent: Hexane (95%) including diethylamine (0.1%)—IPA (5%) including diethylamine (0.1%)
Flow rate: 1.0 mL/min
Retention time=9.72 min (first peak)
$^1$H-NMR (400 MHz, DMSO-D$_6$) δ:8.11-8.03 (4H, m), 7.25-7.15 (2H, m), 4.76-4.66 (1H, m), 3.53-3.44 (1H, s), 3.25-3.10 (2H, m), 1.85-1.67 (2H, m), 0.99 (3H, t, J=7.3 Hz).

Example 44 rel-1-[(2S,3R)-2-ethyl-2,3-dihydrofuro[3,2-b]pyridin-3-yl]methanamine dihydrochloride

[Chemical Formula 29]

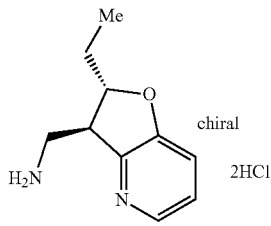

The compound of Reference Example 33 was optically resolved by chiral HPLC to give a compound having the second peak. Then, by the same method as in Example 39, the title compound was obtained.
[Chiral HPLC Condition]
Column: IC
Solvent: Hexane (95%) including diethylamine (0.1%)—IPA (5%) including diethylamine (0.1%)
Flow rate: 1.0 mL/min
Retention time=12.64 min (second peak)
$^1$H-NMR (400 MHz, DMSO-D$_6$) δ:8.30-8.02 (4H, m), 7.24-7.19 (2H, m), 4.75-4.65 (1H, s), 3.53-3.48 (1H, m), 3.23-3.13 (2H, m), 1.81-1.70 (2H, m), 0.97 (3H, t, J=6.7 Hz).

Example 45 rac-1-(3,4-dihydro-2H-thiopyrano[3,2-b]pyridin-4-yl)-N-methylmethanamine dihydrochloride

[Chemical Formula 30]

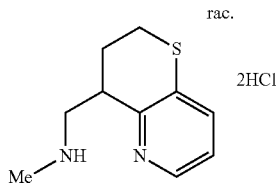

To a mixture of the compound (244 mg, 0.870 mmol) of Reference Example 15 and N,N-dimethylformamide (2.2 mL) was added 55% sodium hydride (144 mg) under ice-cooling. After stirring under ice-cooling for 10 min, iodomethane (0.544 mL, 8.70 mmol) was added thereto. After stirring at room temperature for 2 hr, saturated aqueous ammonium chloride solution (5 mL) was added thereto, the mixture was subjected to extraction with 2:1-hexane/ethyl acetate (5 mL×three times), and the organic layer was dried over anhydrous magnesium sulfate, filtered, and concentrated. The concentrated residue was separated and purified by silica gel column chromatography (hexane/ethyl acetate).

To a mixture of the obtained compound (150 mg) and ethyl acetate (1.1 mL) was added 4 mol/L hydrogen chloride-ethyl acetate (1.1 mL), and the mixture was stirred at room temperature for 2 hr. Then, the precipitated solid was collected by filtration, washed with diethyl ether (4.0 mL), and dried under reduced pressure to give the title compound (101 mg).

$^1$H-NMR (400 MHz, DMSO-D$_6$)

δ:8.87 (2H, brs), 8.26 (1H, dd, J=4.6, 1.2 Hz), 7.64 (1H, dd, J=7.9, 1.2 Hz), 7.24 (1H, dd, J=7.9, 4.6 Hz), 3.36-3.32 (2H, m), 3.23-3.10 (3H, m), 2.62 (3H, t, J=5.5 Hz), 2.29-2.25 (1H, m), 2.04-2.02 (1H, m).

Example 46

N-methyl-1-[(2R,3S)-2-methyl-2,3-dihydrofuro[3,2-b]pyridin-3-yl]methanamine dihydrochloride

[Chemical Formula 31]

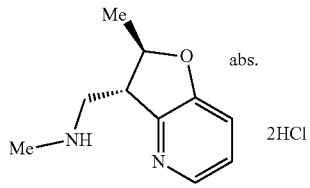

To a mixture of the compound (10 mg, 0.042 mmol) of Example 27 and chloroform (0.10 mL) were added triethylamine (0.024 mL, 0.169 mmol) and di-tert-butyl dicarbonate (18 mg, 0.084 mmol). After stirring at room temperature for 1 hr, the reaction mixture was concentrated. The concentrated residue was separated and purified by silica gel column chromatography (hexane/ethyl acetate).

To a mixture of the obtained compound (101 mg, 0.382 mmol) and N,N-dimethylformamide (0.764 mL) was added 55% sodium hydride (50.0 mg) under ice-cooling. After stirring under ice-cooling for 10 min, iodomethane (0.239 mL, 3.82 mmol) was added thereto. After stirring at room temperature for 1 hr, water (2 mL) was added thereto, the mixture was subjected to extraction with chloroform (2 mL×three times), and the organic layer was dried over anhydrous magnesium sulfate, filtered, and concentrated. The concentrated residue was separated and purified by silica gel column chromatography (hexane/ethyl acetate).

To a mixture of the obtained compound (50 mg) and ethyl acetate (1.0 mL) was added 4 mol/L hydrogen chloride-ethyl acetate (0.955 mL), and the mixture was stirred at room temperature for 2 hr. Then, the precipitated solid was collected by filtration, and dried under reduced pressure to give the title compound (45 mg).

$^1$H-NMR (400 MHz, DMSO-D$_6$)

δ:9.42 (2H, brs), 8.12 (1H, dd, J=4.6, 1.5 Hz), 7.38 (1H, dd, J=8.5, 1.5 Hz), 7.34 (1H, dd, J=8.5, 4.6 Hz), 5.11 (1H, dq, J=6.7, 6.1 Hz), 3.72-3.67 (1H, m), 3.42-3.25 (2H, m), 2.59 (3H, t, J=5.2 Hz), 1.48 (3H, d, J=6.7 Hz).

Examples 47 to 48

According to the method described in Example 46, the compounds of Examples 47 to 48 were obtained from the corresponding compounds of Examples, respectively.

TABLE 5

| Ex. No. | Chemical Structure | Instrumental analysis data |
|---|---|---|
| 47 | (structure: Me, abs., 2HCl, Me-NH, Me, O, N, Me) | $^1$H-NMR (400 MHz, DMSO-$D_6$) δ: 8.99 (2H, brs), 7.49 (1H, brs), 7.33 (1H, brs), 4.37-4.27 (1H, m), 3.49-3.34 (2H, m), 3.34-3.22 (1H, m), 2.65 (3H, t, J = 6.5 Hz), 2.51 (3H, s), 2.33-2.22 (1H, m), 1.86-1.76 (1H, m), 1.36 (3H, d, J = 6.1 Hz). |
| 48 | (structure: Me, abs., 2HCl, Me-NH, O, N, Me) | $^1$H-NMR (400 MHz, CDCl$_3$) δ: 6.88 (1H, d, J = 8.6 Hz), 6.84 (1H, d, J = 8.6 Hz), 4.68 (1H, dq, J = 6.4, 6.1 Hz), 3.15 (1H, dt, J = 6.7, 6.4 Hz), 2.96 (1H, dd, J = 11.6, 6.7 Hz), 2.87 (1H, dd, J = 11.6, 6.7 Hz), 2.47 (3H, s), 2.44 (3H, s), 1.47 (3H, d, J = 6.1 Hz). |

Example 49

1-[(2R,3S)-6-fluoro-2-methyl-2,3-dihydrofuro[3,2-b]pyridin-3-yl]-N-methylmethanamine dihydrobromide

[Chemical Formula 32]

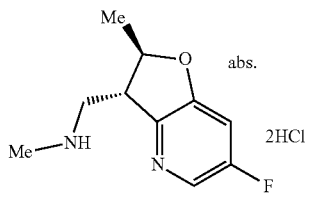 [SMILES: CNC[C@H]1c2ncc(Cl)cc2O[C@@H]1C]

A mixture of the compound (39.5 g, 120 mmol) of Reference Example 55 and 30% hydrobromic acid/acetic acid (117 mL) was stirred at room temperature for 3 hr. Then, the mixture was concentrated. To the concentrated residue was added ethyl acetate, and after stirring, the solid was collected by filtration. A mixture of the obtained solid and ethanol (211 mL) was stirred under heating at 75° C. After confirming complete dissolution of the solid, the solution was cooled to 60° C. After confirming precipitation of solid, hexane (633 mL) was added dropwise thereto. Then, the mixture was cooled gradually to 0° C., and the solid was collected by filtration, washed with hexane/ethanol=9/1 (60 mL) cooled at 0° C., and dried to give the title compound (34.2 g).

$[α]_D^{23.7}$ +33.4 (c0.01, MeOH)
$^1$H-NMR (400 MHz, DMSO-$D_6$)
δ:8.62 (3H, brs), 8.04 (1H, dd, J=2.4, 1.2 Hz), 7.30 (1H, dd, J=9.8, 2.4 Hz), 5.04-4.96 (1H, m), 3.51-3.43 (1H, m), 3.35-3.22 (2H, m), 2.64 (3H, t, J=5.5 Hz), 1.48 (3H, d, J=6.1 Hz).

Examples 50 to 51

According to the method described in Example 46, the compounds of Examples 50 to 51 were obtained from the corresponding compounds of Examples, respectively.

TABLE 6

| Ex. No. | Chemical Structure | Instrumental analysis data |
|---|---|---|
| 50 | (structure: Me, abs., 2HCl, Me-NH, O, N, Cl) | $^1$H-NMR (400 MHz, DMSO-$D_6$) δ: 8.85 (3H, brs), 8.10-8.08 (1H, m), 7.47-7.44 (1H, m), 5.09-4.92 (1H, m), 3.33-3.21 (2H, m), 2.67-2.58 (4H, m), 1.47 (3H, d, J = 6.7 Hz). |
| 51 | (structure: Me, abs., 2HCl, Me-NH, O, N, Me) | $^1$H-NHR (400 MHz, CD$_3$OD) δ: 8.27 (1H, d, J = 6.1 Hz), 7.74 (1H, d, J = 5.5 Hz), 5.32-5.25 (1H, m), 4.12-4.05 (1H, m), 3.65-3.52 (2H, m), 2.83 (3H, s), 2.48 (3H, s), 1.62 (3H, d, J = 6.1 Hz). |

Examples 52 to 61

According to the method described in Example 27, the compounds of Examples 52 to 61 were obtained from the corresponding compounds of Reference Examples, respectively.

TABLE 7-1

| Ex. No. | Chemical Structure | Instrumental analysis data |
|---|---|---|
| 52 | (structure: Me, abs., 2HCl, NH$_2$, O, N, F) | $^1$H-NMR (400 MHz, CDCl$_3$) δ: 8.06 (1H, d, J = 2.4 Hz), 7.08 (1H, dd, J = 9.6, 2.4 Hz), 4.43-4.34 (1H, m), 3.40-3.22 (3H, m), 2.28-2.19 (1H, m), 1.67-1.58 (1H, m), 1.46 (3H, d, J = 7.0 Hz). |

TABLE 7-1-continued

| Ex. No. | Chemical Structure | Instrumental analysis data |
|---|---|---|
| 53 | (rac.) 2HCl | ¹H-NHR (400 MHz, CD₃OD) δ: 8.29-8.18 (1H, m), 7.51-7.43 (2H, m), 4.01-3.92 (2H, m), 3.51-3.40 (1H, m), 3.21-3.12 (2H, m), 1.12 (3 H, s), 1.03 (3H, s). |
| 54 | (abs.) 2HCl | ¹H-NMR (400 MHz, CD₃OD) δ: 8.36 (1H, dd, J = 5.5, 1.2 Hz), 7.82 (1H, dd, J = 8.5, 1.2 Hz), 7.77 (1H, dd, J = 8.5, 5.5 Hz), 5.36 (1H, dq, J = 6.1, 3.0 Hz), 3.78 (1H, d, J = 3.0 Hz), 1.52 (3H, d, J = 6.1 Hz), 1.47 (3H, s), 1.43 (3H, s). |
| 55 | (chiral) 2HCl | ¹H-NMR (400 MHz, DMSO-D₆) δ: 8.25 (3H, br s), 8.09 (1H, dd, J = 3.7, 2.4 Hz), 7.28-7.24 (2H, m), 5.01 (1H, dq, J = 6.1, 6.1 Hz), 3.60 (1H, dq, J = 6.7, 5.8 Hz), 3.41 (1H, dd, J = 6.1, 5.8 Hz), 1.41 (3H, d, J = 6.1 Hz), 1.23 (3H, d, J = 6.7 Hz). |
| 56 | (chiral) 2HCl | ¹H-NMR (400 MHz, DMSO-D₆) δ: 8.30 (3H, br s), 8.07 (1H, dd, J = 3.0, 3.0 Hz), 7.28-7.22 (2H, m), 5.06-4.96 (1H, m), 3.65-3.56 (1H, m), 3.44-3.36 (1H, m), 1.43 (3H, d, J = 6.7 Hz), 1.10 (3H, d, J = 6.7 Hz). |
| 57 | (rac.) 2HCl | 1H-NMR (400 MHz, DMSO-D₆) δ: 8.29 (3H, s), 8.08-8.07 (1H, m), 7.30-7.24 (2H, m), 3.50-3.48 (1H, m), 3.27-3.24 (1H, m), 3.17-3.14 (1H, m), 1.47 (3H, s). |
| 58 | (rac.) 2HCl | ¹H-NMR (400 MHz, CD₃OD) δ: 8.28 (1H, dd, J = 3.4, 3.4 Hz), 7.54 (2H, d, J = 3.7 Hz), 3.95-3.93 (1H, m), 3.43-3.40 (1H, m), 3.35-3.28 (1H, m), 1.33-1.26 (2H, m), 1.23-1.17 (1H, m), 0.94-0.89 (1H, m). |
| 59 | (abs.) | ¹H-NMR (400 MHz, CDCl₃) δ: 7.99 (1H, dd, J = 6.4, 6.4 Hz), 6.88 (1H, dd, J = 10.4, 6.4 Hz), 4.83 (1H, dq, J = 6.1, 6.1 Hz), 3.18-3.05 (3H, m), 1.57 (3H, d, J = 6.1 Hz). |

TABLE 7-1-continued

| Ex. No. | Chemical Structure | Instrumental analysis data |
|---|---|---|
| 60 | 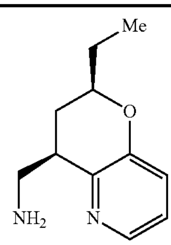 | ¹H-NHR (400 MHz, CD₃OD) δ: 8.10-8.09 (1H, m), 7.23-7.23 (2H, m), 4.13-4.10 (1H, m), 3.23-3.20 (3H, m), 2.23-2.18 (1H, m), 1.84-1.74 (2H, m), 1.61-1.58 (1H, m), 1.10-1.08 (3H, m). |
| 61 | 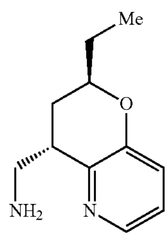 | ¹H-NHR (400 MHz, CD₃OD) δ: 8.13-8.10 (1H, m), 7.27-7.23 (2H, m), 4.12-4.09 (1H, m), 3.29-3.13 (3H, m), 2.04-2.02 (2H, m), 1.78-1.69 (2H, m), 1.09-1.07 (3H, m). |

Example 62 rac-1-[(2R,3R,4R)-2,3-dimethyl-3,4-dihydro-2H-pyrano[3,2-b]pyridin-4-yl]methanamine dihydrochloride

[Chemical Formula 33]

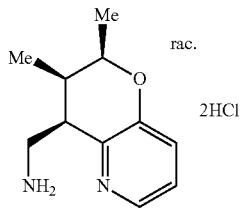

To a methanol solution (1.2 mL) of the compound (120 mg, 0.368 mmol) of Reference Example 88-1 was added 10% palladium-carbon (60 mg). After stirring under hydrogen atmosphere at room temperature for 4 hr, the mixture was filtered through Celite, and the filtrate was concentrated. To the concentrated residue was added 4 mol/L hydrochloric acid-ethyl acetate (0.5 mL), and the mixture was triturated with diethyl ether to give a hydrochloride of the title compound as a mixture with impurities. To a tetrahydrofuran suspension (3.68 mL) of the mixture were added triethylamine (0.154 mL) and di-tert-butyl dicarbonate (96 mg). After stirring at room temperature for 2 hr, water was added thereto, the mixture was subjected to extraction with ethyl acetate, and the organic layer was dried over anhydrous sodium sulfate, filtered, and concentrated. The concentrated residue was separated and purified by silica gel column chromatography (hexane/ethyl acetate) to give a purified product (38.7 mg). To an ethyl acetate solution (0.4 mL) of this purified product (38.7 mg) was added 4 mol/L hydrochloric acid-ethyl acetate (0.331 mL). After stirring at room temperature for 2 hr, the precipitated solid was collected by filtration, and dried under reduced pressure to give a hydrochloride of the title compound (24.2 mg) as a white solid.

¹H-NMR (400 MHz, CD₃OD) δ:8.31-8.26 (1H, m), 7.75-7.60 (2H, m), 4.57-4.54 (1H, m), 3.80-3.76 (2H, m), 3.36-3.33 (1H, m), 2.33 (9H, m), 1.48-1.47 (3H, m), 0.92-0.189 (3H, m)

Examples 63 to 66

According to the method described in Example 62, the compounds of Examples 63 to 66 were obtained from the corresponding compounds of Reference Examples, respectively.

TABLE 8

| Ex. No. | Chemical Structure | Instrumental analysis data |
|---|---|---|
| 63 | 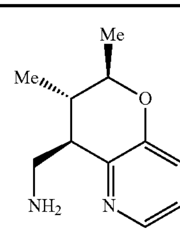 | ¹H-NMR (400 MHz, CD₃OD) δ: 8.24-8.22 (1H, m), 7.49-7.47 (1H, m), 7.44-7.42 (1H, m), 3.98-3.95 (1H, m), 3.64-3.60 (1H, m), 3.26-3.22 (1H, m), 3.06-3.00 (1H, m), 1.76-1.73 (1H, m), 1.48 (3H, d, J = 6.1 Hz), 1.17 (3H, d, J = 6.1 Hz). |

TABLE 8-continued

| Ex. No. | Chemical Structure | Instrumental analysis data |
|---|---|---|
| 64 | 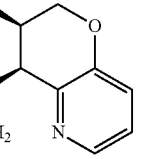 rac. 2HCl | ¹H-NMR (400 MHz, DMSO-D$_6$) δ: 8.22-8.20 (4 H, m), 7.41-7.38 (2H, m), 4.31-4.30 (1H, m), 3.43-3.40 (1H, m), 3.29-3.26 (1H, m), 3.15-3.13 (1H, m), 2.16-2.14 (1H, m), 1.28 (3H, d, J = 6.1 Hz), 0.93 (3H, d, J = 7.3 Hz). |
| 65 | rac. 2HCl | ¹H-NMR (400 MHz, CD$_3$OD) δ: 8.43-8.42 (1H, m), 7.92 (1H, d, J = 8.5 Hz), 7.79-7.77 (1H, m), 4.50-4.48 (1H, m), 3.48-3.45 (1H, m), 3.42-3.40 (1H, m), 3.36-3.35 (1H, m), 2.29-2.27 (1H, m), 1.48 (3H, d, J = 6.7 Hz), 1.02 (3H, d, J = 6.7 Hz). |
| 66 | chiral 2HCl | ¹H-NMR (400 MHz, CD$_3$OD) δ: 8.13 (1H, d, J = 2.4 Hz), 7.19 (1H, dd, J = 9.8, 2.4 Hz), 4.43-4.39 (1H, m), 3.30-3.25 (3H, m), 2.09-1.97 (2H, m), 1.43 (3H, d, J = 7.0 Hz). |

Examples 67 to 79

According to the method described in Example 8, the compounds of Examples 67 to 79 were obtained from the corresponding compounds of Reference Examples, respectively.

TABLE 9-1

| Ex. No. | Chemical Structure | Instrumental analysis data |
|---|---|---|
| 67 | rac. 2HCl | ¹H-NMR (400 MHz, CDCl$_3$) δ: 9.15-8.85 (2H, m), 7.53-7.47 (1H, m), 7.33-7.26 (1H, m), 4.52-4.42 (1H, m), 4.30-4.19 (1H, m), 3.82-3.52 (2H, m), 3.40-3.23 (1H, m), 2.59-2.26 (1 H, m), 2.05-1.85 (1H, m). |
| 68 | rac. 2HCl | ¹H-NMR (400 MHz, DMSO-D$_6$) δ: 8.34 (3H, br s), 7.88 (1H, d, J = 3.7 Hz), 7.48-7.46 (2H, m), 3.70-3.50 (2H, brs), 3.28-3.19 (3H, m), 3.16-3.06 (1H, m), 2.09-1.99 (1H, m), 1.87-1.77 (1H, m). |
| 69 | rac. 2HCl | ¹H-NHR (400 MHz, DMSO-D$_6$) δ: 7.81 (3H, br s), 7.78 (1H, dd, J = 4.9, 2.4 Hz), 7.12 (1H, d d, J = 8.5, 2.4 Hz), 7.02 (1H, dd, J = 8.5, 4.9 Hz), 4.01 (1H, d, J = 11.6 Hz), 3.08 (1H, dd, J = 11.6, 1.2 Hz), 2.83-2.77 (2H, m), 2.31 (1H, t, J = 7.3 Hz), 0.61-0.56 (1H, m), 0.30-0.25 (1H, m), 0.16-0.11 (1H, m), 0.04-0.02 (1H, m). |

TABLE 9-1-continued

| Ex. No. | Chemical Structure | Instrumental analysis data |
|---|---|---|
| 70 | (rac., 2HCl) | $^1$H-NMR (400 MHz, CD$_3$OD) δ: 8.27 (1H, d, J = 5.5 Hz), 7.71 (1H, d, J = 5.5 Hz), 4.58-4.51 (1H, m), 4.46-4.38 (1H, m), 3.72-3.64 (1H, m), 3.57-3.50 (1H, m), 3.40-3.37 (1H, m), 2.44 (3H, s), 2.36-2.18 (2H, m). |
| 71 | (abs., 2HCl) | $^1$H-NMR (400 MHz, CD$_3$OD) δ: 8.20-8.19 (1H, m), 7.49-7.48 (2H, m), 6.05-5.95 (1H, m), 5.63-5.54 (2H, m), 4.98-4.93 (1H, m), 3.79 (2H, d, J = 6.1 Hz), 3.73-3.71 (1H, m), 3.48-3.46 (2H, m), 1.58 (3H, d, J = 6.7 Hz). |
| 72 | (abs., 2HCl) | $^1$H-NMR (400 MHz, DMSO-D$_6$) δ: 8.79 (2H, s), 7.98-7.97 (1H, m), 7.15-7.12 (2H, m), 4.87-4.86 (1H, m), 3.46-3.44 (1H, m), 3.22-3.16 (2H, m), 2.89-2.83 (2H, m), 1.61-1.57 (2H, m), 1.39 (3H, d, J = 6.1 Hz), 0.84 (3H, t, J = 7.6 Hz). |
| 73 | (abs., 2HCl) | $^1$H-NMR (400 MHz, DMSO-D$_6$) δ: 9.12 (2H, s), 8.06-8.05 (1H, m), 7.26-7.21 (2H, m), 5.02-4.95 (1H, m), 3.70-3.64 (2H, m), 3.62-3.56 (1H, m), 3.34-3.20 (7H, m), 1.46 (3H, d, J = 6.1 Hz). |

TABLE 9-2

| Ex. No. | Chemical Structure | Instrumental analysis data |
|---|---|---|
| 74 | (abs., 2HCl) | $^1$H-NMR (400 MHz, DMSO-D$_6$) δ: 8.99 (2H, s), 8.07-8.06 (1H, m), 7.25-7.23 (2H, m), 5.00-4.99 (1H, m), 3.56-3.53 (1H, m), 3.30-3.23 (2H, m), 3.05-2.99 (2H, m), 1.47 (3H, d, J = 6.1 Hz), 1.25-1.23 (3H, m). |
| 75 | (rac., 2HCl) | $^1$H-NMR (400 MHz, DMSO-D$_6$) δ: 8.34 (1H, d, J = 5.5 Hz), 8.02 (3H, s), 7.39 (1H, d, J = 5.5 Hz), 3.52-3.50 (1H, m), 3.30-3.24 (1H, m), 3.05-2.88 (3H, m), 2.38-2.35 (1H, m), 1.90-1.87 (1H, m). |
| 76 | (rac., 2HCl) | $^1$H-NMR (400 MHz, CD$_3$OD) δ: 8.55 (1H, d, J = 6.7 Hz), 7.46 (1H, d, J = 7.3 Hz), 4.47-4.45 (2H, m), 3.93 (1H, brs), 3.61-3.53 (1H, m), 3.26-3.19 (1H, m), 3.12-3.03 (2H, m), 2.61-2.58 (1H, m), 2.20-2.19 (1H, m), 1.52-1.50 (3H, m). |

TABLE 9-2-continued

| 77 | [structure: methyl-tetrahydroquinoline with CH2NH2, rac., 2HCl] | ¹H-NMR (400 MHz, DMSO-D₆) δ: 8.56-8.51 (1 H, m), 8.28 (3H, brs), 8.09 (1H, brs), 7.58 (1 H, brs), 3.41-3.30 (2H, m), 3.17-2.97 (2H, m), 2.08-1.44 (4H, m), 1.30-1.26 (3H, m). |
| --- | --- | --- |
| 78 | [structure: methyl-cyclopenta-pyridine with CH2NHMe, rac., 2HCl] | ¹H-NMR (400 MHz, DMSO-D₆) δ: 9.10 (2H, br s), 8.46 (1H, d, J = 4.9 Hz), 7.93 (1H, d, J = 7.3 Hz), 7.49-7.46 (1H, m), 3.68-3.59 (2H, m), 3.28-3.13 (2H, m), 2.68-2.62 (4H, m), 1.48 (1H, dd, J = 22.3, 10.1 Hz), 1.33 (3H, d, J = 6.7 Hz). |
| 79 | [structure: dimethyl-furopyridine with CH2NHMe, Me on pyridine, rac., 2HCl] | ¹H-NMR (400 MHz, CD₃OD) δ: 7.56-7.52 (2H, m), 3.88 (1H, m), 3.56-3.53 (2H, m), 3.34 (3 H, s), 2.86 (3H, s), 2.65 (3H, d, J = 10.0 Hz), 1.63 (3H, s). |

Examples 80 to 87

According to the method described in Example 49, the compounds of Examples 80 to 87 were obtained from the corresponding compounds of Reference Examples, respectively.

TABLE 10-1

| Ex. No. | Chemical Structure | Instrumental analysis data |
| --- | --- | --- |
| 80 | [structure: methyl-furopyridine with F, CH2-NH-CD3, abs., 2HBr] | $[\alpha]_D^{25.7}$ +36.0 (c0.01, MeOH)<br>¹H-NMR (400 MHz, DMSO-D₆) δ: 8.57 (2H, br s), 8.04 (1H, d, J = 2.4 Hz), 7.31-7.29 (1H, m), 5.03-4.96 (1H, m), 3.47-3.45 (1H, m), 3.31-3.22 (2H, m), 1.48 (3H, d, J = 6.1 Hz). |
| 81 | [structure: spirocyclopropyl-furopyridine with Cl, CH2NH2, rac., 2HBr] | ¹H-NMR (400 MHz, DMSO-D₆) δ: 7.87 (3H, s), 7.36 (2H, s), 3.69 (1H, s), 3.20-3.17 (1H, m), 3.10-3.07 (1H, m), 1.21-1.06 (3H, m), 0.84 (1H, dd, J = 10.7, 5.8 Hz). |
| 82 | [structure: spirocyclopropyl-furopyridine with F, CH2NH2, rac., 2HBr] | ¹H-NMR (400 MHz, DMSO-D₆) δ: 7.89 (3H, s), 7.47-7.45 (1H, m), 7.04 (1H, d, J = 8.5 Hz), 3.68-3.64 (1H, m), 3.20-3.14 (1H, m), 3.08-3.05 (1H, m), 1.20-1.17 (1H, m), 1.10-1.05 (2 H, m), 0.84-0.81 (1H, m). |

TABLE 10-1-continued

| Ex. No. | Chemical Structure | Instrumental analysis data |
|---|---|---|
| 83 | (structure: rac. dimethyl furo-pyridine with CH2NH2, 2HBr, Me on pyridine) | ¹H-NMR (400 MHz, DMSO-D₆) δ: 7.98 (3H, br s), 7.11 (1H, d, J = 8.5 Hz), 7.06 (1H, d, J = 8.5 Hz), 3.43-3.41 (1H, m), 3.30-3.20 (2H, m), 2.41 (3H, s), 1.52 (3H, s), 1.32 (3H, s). |
| 84 | (structure: abs. methyl furo-pyridine with CH2NH2, 2HBr, two Me on pyridine) | ¹H-NMR (400 MHz, DMSO-D₆) δ: 8.15 (3H, br s), 7.35 (1H, brs), 5.09-5.07 (1H, m), 3.76-3.73 (1H, m), 3.40-3.38 (1H, m), 3.29-3.27 (1H, m), 2.52 (3H, s), 2.25 (3H, s), 1.47 (3H, d, J = 6.1 Hz). |
| 85 | (structure: rac. methyl furo-pyridine with CH2NH2, 2HBr, Cl on pyridine) | ¹H-NMR (400 MHz, CD₃OD) δ: 8.35 (1H, s), 7.72 (1H, s), 3.42-3.33 (1H, m), 3.25-3.11 (2H, m), 3.02-3.00 (1H, m), 2.72-2.60 (1H, m), 2.43-2.25 (1H, m), 1.34-1.27 (3H, m). |
| 86 | (structure: rac. ethyl chromeno-pyridine with CH2NH2, 2HCl) | ¹H-NMR (400 MHz, CD₃OD) δ: 8.37 (1H, dd, J = 5.5, 1.2 Hz), 7.91 (1H, d, J = 7.9 Hz), 7.78 (1H, dd, J = 8.5, 5.5 Hz), 4.44 (1H, dd, J = 11.6, 3.0 Hz), 4.28 (1H, dd, J = 11.9, 9.4 Hz), 3.86-3.79 (1H, m), 3.47-3.34 (2H, m), 2.35-2.24 (1H, m), 1.64-1.52 (1H, m), 1.51-1.38 (1H, m), 1.11 (3H, t, J = 7.6 Hz). |
| 87 | (structure: rac. ethyl chromeno-pyridine with CH2NH2, 2HCl) | ¹H-NMR (400 MHz, CD₃OD) δ: 8.41 (1H, d, J = 4.3 Hz), 7.90 (1H, d, J = 7.9 Hz), 7.76 (1H, dd, J= 8.5, 5.5 Hz), 4.42-4.31 (2H, m), 3.50-3.34 (3H, m), 2.16-2.07 (1H, m), 1.54-1.40 (2H, m), 1.08 (3H, t, J = 7.3 Hz). |

Example 88 rac-1-(2-methoxy-5,6,7,8-tetrahydroquinolin-8-yl)methanamine dihydrochloride

[Chemical Formula 34]

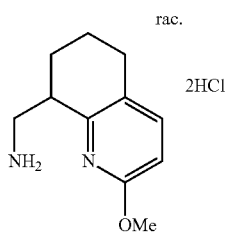

To a methanol solution (0.28 mL) of the compound (9 mg, 0.028 mmol) of Reference Example 91 was added hydrazine monohydrate (0.007 mL, 0.140 mmol) at room temperature. After stirring at 50° C. for 2 hr, the reaction mixture was concentrated. To the concentrated residue was added 1 mol/L hydrochloric acid, the precipitated solid was filtered off, and washed with water, and the filtrate was concentrated. The concentrated residue was washed with diethyl ether, and dried under reduced pressure to give the title compound (7 mg).

¹H-NMR (400 MHz, CD₃OD) δ:7.82 (1H, d, J=8.5 Hz), 7.03 (1H, d, J=8.5 Hz), 4.04 (3H, s), 3.35-3.24 (3H, m), 2.81-2.79 (2H, m), 2.05-2.02 (1H, m), 1.95-1.91 (1H, m), 1.84-1.83 (2H, m).

Example 89 rac-1-[4-(4-methylphenyl)-5,6,7,8-tetrahydroquinolin-8-yl]methanamine dihydrochloride

[Chemical Formula 35]

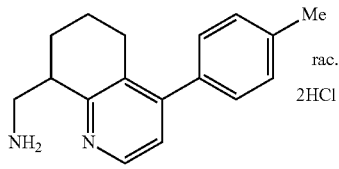

By the same method as in Example 88, the title compound was obtained from the compound of Reference Example 101.

$^1$H-NMR (400 MHz, CD$_3$OD) δ:8.62 (1H, d, J=5.5 Hz), 7.67 (1H, d, J=6.1 Hz), 7.39-7.33 (4H, m), 3.67-3.64 (1H, m), 3.53-3.48 (1H, m), 3.37-3.34 (1H, m), 2.86-2.84 (2H, m), 2.43 (3H, s), 2.19-2.11 (1H, m), 2.01-1.82 (3H, m).

Example 90 rac-1-(5'-methyl-3'H-spiro[cyclopropane-1,2'-furo[3,2-b]pyridine]-3'-yl)methanamine dihydrochloride

[Chemical Formula 36]

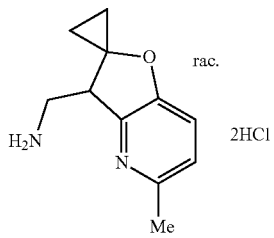

To a mixture of the compound (300 mg, 0.870 mmol) of Reference Example 95, cesium carbonate (850 mg, 2.61 mmol), trimethylboroxin (0.365 mL), toluene (2.9 mL) and water (1.45 mL) was added (2-dicyclohexylphosphino-2',4',6'-triisopropyl-1,1'-biphenyl) [2-(2'-amino-1,1'-biphenyl)]palladium(II) methanesulfonate (73.6 mg, 0.087 mmol). After stirring at 90° C. for 5 hr, saturated aqueous ammonium chloride solution (30 mL) was added thereto. The mixture was subjected to extraction with ethyl acetate (30 mL×twice), and the organic layer was dried over anhydrous sodium sulfate, filtered, and concentrated. The concentrated residue was separated and purified by silica gel column chromatography (hexane/ethyl acetate) to give a purified product (128 mg). To this purified product (128 mg) was added 5.1 mol/L hydrobromic acid-acetic acid (0.387 mL) under ice-cooling. After stirring at room temperature for 2 hr, the reaction mixture was concentrated. The concentrated residue was separated and purified by amino silica gel column chromatography (chloroform/methanol). To a 2-propanol solution (1.0 mL) of the obtained purified product was added 4 mol/L hydrochloric acid-ethyl acetate (3.0 mL), and the precipitated solid was collected by filtration to give the title compound (44.4 mg).

$^1$H-NMR (400 MHz, CD$_3$OD) δ:7.03-7.02 (2H, m), 3.39-3.27 (1H, m), 3.04-3.00 (1H, m), 2.88-2.85 (1H, m), 2.47 (3H, s), 1.13-1.08 (3H, m), 0.91-0.89 (1H, m).

Example 91 rac-1-[4-(cyclobutyloxy)-6,7-dihydro-5H-cyclopenta[b]pyridin-7-yl]methanamine dihydrochloride

[Chemical Formula 37]

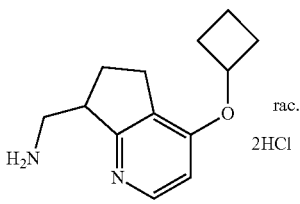

To a toluene solution (1.9 mL) of the compound (50.0 mg, 0.189 mmol) of Reference Example 100 and cyclobutanol (0.045 mL, 0.567 mmol) was added cyanomethylenetributylphosphorane (0.149 mL, 0.567 mmol). After stirring at 100° C. for 3 hr, to the reaction mixture was added water (30 mL), the mixture was subjected to extraction with ethyl acetate (30 mL×twice), and the organic layer was dried over anhydrous sodium sulfate, filtered, and concentrated. The concentrated residue was separated and purified by silica gel column chromatography (hexane/ethyl acetate). To the obtained purified product was added 4 mol/L hydrobromic acid-acetic acid (0.500 mL). After stirring at room temperature for 2 hr, the reaction mixture was concentrated. The concentrated residue was separated and purified by reverse-phase silica gel column chromatography (water/acetonitrile). To a 2-propanol solution (1.0 mL) of the obtained purified product was added 4 mol/L hydrochloric acid-ethyl acetate (1.0 mL), and the mixture was concentrated to give the title compound (8.2 mg).

$^1$H-NMR (400 MHz, CD$_3$OD) δ:8.51 (1H, d, J=6.7 Hz), 7.29 (1H, d, J=6.7 Hz), 5.14-5.07 (1H, m), 3.94-3.90 (1H, m), 3.59-3.56 (1H, m), 3.24-3.21 (1H, m), 3.16-2.98 (2H, m), 2.64-2.55 (3H, m), 2.27-2.21 (3H, m), 1.99-1.94 (1H, m), 1.86-1.78 (1H, m).

Example 92 rac-1-(4-methyl-5,6,7,8-tetrahydroquinolin-8-yl)methanamine

[Chemical Formula 38]

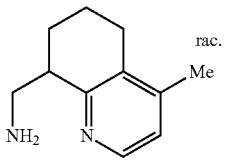

To a tetrahydrofuran solution (1.2 mL) of the compound (40.2 mg, 0.233 mmol) of Reference Example 104 was added 0.91 mol/L borane-tetrahydrofuran complex tetrahydrofuran solution (0.769 mL, 0.700 mmol) under ice-cooling. After stirring at room temperature for 2 hr, to the reaction mixture was added methanol (1.0 mL), and then, conc. hydrochloric acid (1.0 mL) was added thereto. After stirring at 50° C. for 1 hr, to the reaction mixture was added 1 mol/L aqueous sodium hydroxide solution, the mixture was subjected to extraction with chloroform/methanol=4/1 (30 mL×twice), and the organic layer was dried over anhydrous sodium sulfate, filtered, and concentrated. The concentrated residue was separated and purified by amino silica gel column chromatography (chloroform/methanol) to give the title compound (33.5 mg).

$^1$H-NMR (400 MHz, CDCl$_3$) δ:8.26 (1H, d, J=4.9 Hz), 6.90 (1H, d, J=4.9 Hz), 3.13 (1H, dd, J=12.8, 5.5 Hz), 3.01 (1H, dd, J=12.8, 6.7 Hz), 2.90-2.84 (1H, m), 2.63 (2H, t, J=6.1 Hz), 2.20 (3H, s), 1.98-1.74 (4H, m).

Example 93-1, Example 93-2

Example 93-1 rac-1-[(5R,7S)-5-methyl-6,7-dihydro-5H-cyclopenta[b]pyridin-7-yl]methanamine

Example 93-2 rac-1-[(5R,7R)-5-methyl-6,7-dihydro-5H-cyclopenta[b]pyridin-7-yl]methanamine

[Chemical Formula 39]

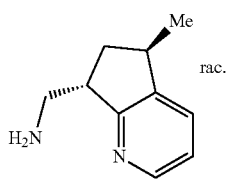

Example 93-1

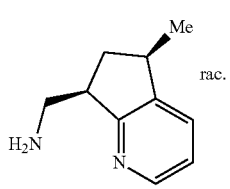

Example 93-2

By the same method as in Example 92, the title compounds were obtained as a diastereomeric mixture (1:1) of Example 93-1 and Example 93-2 from the compound of Reference Example 108.

$^1$H-NMR (400 MHz, CDCl$_3$) δ:8.37-8.36 (1H, m), 7.47-7.44 (1H, m), 7.10-7.06 (1H, m), 3.31-1.85 (6H, m), 1.40-1.26 (3H, m).

Example 94 rel-1-[(2S,3R)-2-methyl(2-$^2$H)-2,3-dihydrofuro[3,2-b]pyridin-3-yl]methanamine dihydrochloride

[Chemical Formula 40]

To a tetrahydrofuran solution (2.4 mL) of the compound of Example 57 (112 mg, 0.470 mmol) and triethylamine (0.328 mL, 2.35 mmol) was added di-tert-butyl dicarbonate (113 mg, 0.517 mmol). After stirring at room temperature for 15 hr, to the reaction mixture was added water (30 mL), the mixture was subjected to extraction with ethyl acetate (30 mL×twice), and the organic layer was dried over anhydrous sodium sulfate, filtered, and concentrated. The concentrated residue was separated and purified by silica gel column chromatography (hexane/ethyl acetate) to give a purified product (120 mg). The obtained purified product was optically resolved by chiral HPLC to give the compound (48.7 mg) having the first peak. Then, by the same method as in Example 39, the title compound (42.9 mg) was obtained.

[Chiral HPLC Condition]
Column: IC
Solvent: Hexane (90%) including diethylamine (0.1%)—IPA (10%) including diethylamine (0.1%)
Flow rate: 1.0 mL/min
Retention time=6.80 min (first peak)

$^1$H-NMR (400 MHz, DMSO-D$_6$) δ:8.23 (3H, s), 8.07-8.06 (1H, m), 7.27-7.22 (2H, m), 3.47-3.45 (1H, m), 3.28-3.12 (2H, m), 1.47 (3H, s).

Example 95 rel-1-[(2R,3S)-2-methyl(2-$^2$H)-2,3-dihydrofuro[3,2-b]pyridin-3-yl]methanamine dihydrochloride

[Chemical Formula 41]

The corresponding Boc-form was obtained from the compound of Example 57 by the same method as in Example 94, and optically resolved by chiral HPLC to give a compound having the second peak. Then, by the same method as in Example 39, the title compound was obtained.

[Chiral HPLC Condition]
Column: IC
Solvent: Hexane (90%) including diethylamine (0.1%)—IPA (10%) including diethylamine (0.1%)

Flow rate: 1.0 mL/min
Retention time=8.43 min (second peak)
¹H-NMR (400 MHz, DMSO-D₆) δ:8.27 (3H, s), 8.08-8.07 (1H, m), 7.28-7.25 (2H, m), 3.49-3.47 (1H, m), 3.29-3.12 (2H, m), 1.46 (3H, s).

Example 96 rel-1-[(3'R)-3'H-spiro[cyclopropane-1,2'-furo[3,2-b]pyridine]-3'-yl]methanamine dihydrochloride

[Chemical Formula 42]

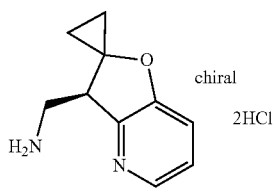

The corresponding Boc-form was obtained from the compound of Example 58 by the same method as in Example 94, and optically resolved by chiral HPLC to give a compound having the first peak. Then, by the same method as in Example 39, the title compound was obtained.
[Chiral HPLC Condition]
Column: IC
Solvent: Hexane (90%)—IPA (10%) including diethylamine (0.1%)
Flow rate: 1.0 mL/min
Retention time=7.41 min (first peak)
¹H-NMR (400 MHz, CD₃OD) δ:8.34-8.34 (1H, m), 7.67-7.65 (2H, m), 4.06-4.04 (1H, m), 3.48-3.45 (1H, m), 3.37-3.33 (1H, m), 1.37-1.21 (3H, m), 0.95-0.93 (1H, m).

Example 97 rel-1-[(3'S)-3'H-spiro[cyclopropane-1,2'-furo[3,2-b]pyridine]-3'-yl]methanamine dihydrochloride

[Chemical Formula 43]

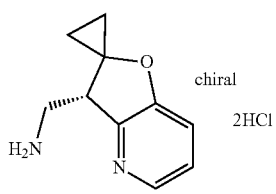

The corresponding Boc-form was obtained from the compound of Example 58 by the same method as in Example 94, and optically resolved by chiral HPLC to give a compound having the second peak. Then, by the same method as in Example 39, the title compound was obtained.
[Chiral HPLC Condition]
Column: IC
Solvent: Hexane (90%)—IPA (10%) including diethylamine (0.1%)
Flow rate: 1.0 mL/min
Retention time=8.21 min (second peak)
¹H-NMR (400 MHz, CD₃OD) δ:8.34-8.34 (1H, m), 7.67-7.64 (2H, m), 4.05-4.04 (1H, m), 3.49-3.45 (1H, m), 3.38-3.33 (1H, m), 1.37-1.22 (3H, m), 0.95-0.93 (1H, m).

Example 98 rel-1-[(3'R)-6'-chloro-3'H-spiro[cyclopropane-1,2'-furo[3,2-b]pyridine]-3'-yl]methanamine dihydrochloride

[Chemical Formula 44]

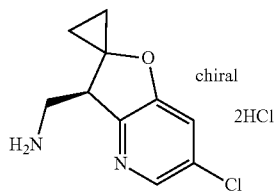

The compound of Reference Example 89 was optically resolved by chiral HPLC to give a compound having the first peak. Then, by the same method as in Example 39, the title compound was obtained.
[Chiral HPLC Condition]
Column: AY-H
Solvent: Hexane (90%)—IPA (10%)
Flow rate: 1.0 mL/min
Retention time=5.04 min (first peak)
¹H-NMR (400 MHz, CD₃OD) δ:8.12-8.12 (1H, m), 7.29-7.29 (1H, m), 3.70-3.69 (1H, m), 3.30-3.29 (1H, m), 3.20-3.18 (1H, m), 1.26-1.24 (1H, m), 1.20-1.08 (2H, m), 0.87-0.86 (1H, m).

Example 99 rel-1-[(3'S)-6'-chloro-3'H-spiro[cyclopropane-1,2'-furo[3,2-b]pyridine]-3'-yl]methanamine dihydrochloride

[Chemical Formula 45]

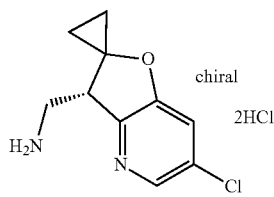

The compound of Reference Example 89 was optically resolved by chiral HPLC to give a compound having the second peak. Then, by the same method as in Example 39, the title compound was obtained.
[Chiral HPLC Condition]
Column: AY-H
Solvent: Hexane (90%)—IPA (10%)
Flow rate: 1.0 mL/min
Retention time=7.34 min (second peak)
¹H-NMR (400 MHz, CD₃OD)
δ:8.13 (1H, d, J=1.8 Hz), 7.30 (1H, d, J=1.8 Hz), 3.72-3.70 (1H, m), 3.34-3.27 (1H, m), 3.21-3.18 (1H, m), 1.29-1.24 (1H, m), 1.17-1.13 (2H, m), 0.90-0.86 (1H, m).

Example 100 rel-1-[(3'R)-5'-methyl-3'H-spiro[cyclopropane-1,2'-furo[3,2-b]pyridine]-3'-yl]methanamine dihydrochloride

[Chemical Formula 46]

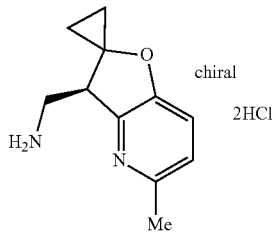

The corresponding Boc-form was obtained from the compound of Example 90 by the same method as in Example 94, and optically resolved by chiral HPLC to give a compound having the first peak. Then, by the same method as in Example 39, the title compound was obtained.

[Chiral HPLC Condition]
Column: AY-H
Solvent: Hexane (95%)—IPA (5%)
Flow rate: 1.0 mL/min
Retention time=5.09 min (first peak)
$^1$H-NMR (400 MHz, CD$_3$OD)
δ:7.60 (1H, d, J=8.5 Hz), 7.51 (1H, d, J=8.5 Hz), 3.98-3.97 (1H, m), 3.47-3.45 (1H, m), 3.35-3.33 (1H, m), 2.67 (3H, s), 1.38-1.34 (1H, m), 1.27-1.24 (2H, m), 0.92-0.90 (1H, m).

Example 101 rel-1-[(3'S)-5'-methyl-3'H-spiro[cyclopropane-1,2'-furo[3,2-b]pyridine]-3'-yl]methanamine dihydrochloride

[Chemical Formula 47]

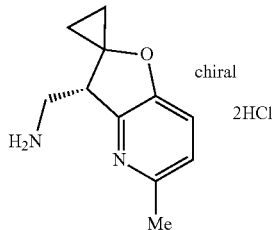

The corresponding Boc-form was obtained from the compound of Example 90 by the same method as in Example 94, and optically resolved by chiral HPLC to give a compound having the second peak. Then, by the same method as in Example 39, the title compound was obtained.

[Chiral HPLC Condition]
Column: AY-H
Solvent: Hexane (95%)—IPA (5%)
Flow rate: 1.0 mL/min
Retention time=6.03 min (second peak)
$^1$H-NMR (400 MHz, CD$_3$OD)
δ:7.49 (1H, d, J=8.5 Hz), 7.42 (1H, d, J=9.2 Hz), 3.91-3.88 (1H, m), 3.45-3.41 (2H, m), 2.64 (3H, s), 1.29-1.21 (3H, m), 0.92-0.89 (1H, m).

Example 102 rel-1-[(3'R)-5'-fluoro-3'H-spiro[cyclopropane-1,2'-furo[3,2-b]pyridine]-3'-yl]methanamine dihydrobromide

[Chemical Formula 48]

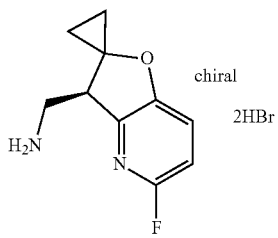

The compound of Reference Example 96 was optically resolved by chiral HPLC to give a compound having the first peak. Then, by the same method as in Example 49, the title compound was obtained.

[Chiral HPLC Condition]
Column: IG
Solvent: Hexane (50%)-EtOH (50%)
Flow rate: 1.0 mL/min
Retention time=5.36 min (first peak)
$^1$H-NMR (400 MHz, DMSO-D$_6$)
δ:7.85 (3H, s), 7.46 (1H, dd, J=8.8, 6.4 Hz), 7.05 (1H, dd, J=8.8, 1.5 Hz), 3.64 (1H, dd, J=8.2, 5.2 Hz), 3.17-3.15 (1H, m), 3.07-3.05 (1H, m), 1.19-1.05 (3H, m), 0.83-0.80 (1H, m).

Example 103 rel-1-[(3'S)-5'-fluoro-3'H-spiro[cyclopropane-1,2'-furo[3,2-b]pyridine]-3'-yl]methanamine dihydrobromide

[Chemical Formula 49]

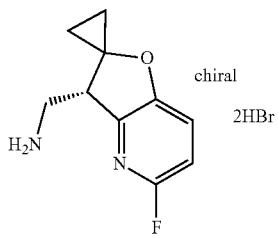

The compound of Reference Example 96 was optically resolved by chiral HPLC to give a compound having the second peak. Then, by the same method as in Example 49, the title compound was obtained.

[Chiral HPLC Condition]
Column: IG
Solvent: Hexane (50%)-EtOH (50%)
Flow rate: 1.0 mL/min
Retention time=7.14 min (first peak)

$^1$H-NMR (400 MHz, DMSO-D$_6$)
δ:7.86 (3H, s), 7.46 (1H, dd, J=8.5, 6.1 Hz), 7.04 (1H, dd, J=8.5, 1.8 Hz), 3.64 (1H, dd, J=7.9, 5.5 Hz), 3.17-3.14 (1H, m), 3.07-3.04 (1H, m), 1.20-1.05 (3H, m), 0.83-0.81 (1H, m).

Example 104 rel-1-[(3R)-2,2,5-trimethyl-2,3-dihydrofuro[3,2-b]pyridin-3-yl]methanamine dihydrochloride

[Chemical Formula 50]

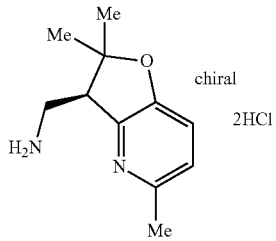

The corresponding Boc-form was obtained from the compound of Example 83 by the same method as in Example 94, and optically resolved by chiral HPLC to give a compound having the first peak. Then, by the same method as in Example 39, the title compound was obtained.
[Chiral HPLC Condition]
 Column: IC
 Solvent: Hexane (95%)—IPA (5%)
 Flow rate: 1.0 mL/min
 Retention time=5.575 min (first peak)
$^1$H-NMR (400 MHz, DMSO-D$_6$) δ:8.11 (3H, brs), 7.08-7.06 (2H, m), 3.44-3.42 (1H, m), 3.25-3.24 (2H, m), 2.41 (3H, s), 1.53 (3H, s), 1.32 (3H, s).

Example 105 rel-1-[(3S)-2,2,5-trimethyl-2,3-dihydrofuro[3,2-b]pyridin-3-yl]methanamine dihydrochloride

[Chemical Formula 51]

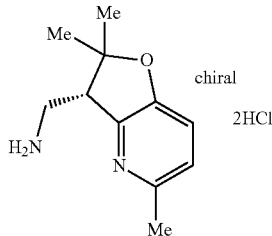

The corresponding Boc-form was obtained from the compound of Example 83 by the same method as in Example 94, and optically resolved by chiral HPLC to give a compound having the second peak. Then, by the same method as in Example 39, the title compound was obtained.
[Chiral HPLC Condition]
 Column: IC
 Solvent: Hexane (95%)—IPA (5%)
 Flow rate: 1.0 mL/min
 Retention time=6.539 min (second peak)
$^1$H-NMR (400 MHz, DMSO-D$_6$) δ:8.03 (3H, brs), 7.08-7.04 (2H, m), 3.42-3.40 (1H, m), 3.24-3.20 (2H, m), 2.40 (3H, s), 1.52 (3H, s), 1.32 (3H, s).

Example 106 rac-1-(5-fluoro-2,2-dimethyl-2,3-dihydrofuro[3,2-b]pyridin-3-yl)methanamine dihydrobromide

[Chemical Formula 52]

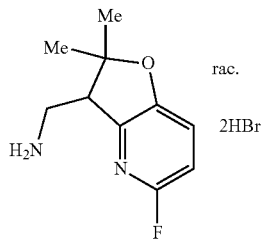

By the same method as in Example 49, the title compound was obtained from the compound of Reference Example 118.
$^1$H-NMR (400 MHz, DMSO-D$_6$) δ:7.95 (3H, brs), 7.39-7.37 (1H, m), 6.99-6.97 (1H, m), 3.45-3.43 (1H, m), 3.21-3.18 (2H, m), 1.52 (3H, s), 1.36 (3H, s).

Reference Example 1-1, Reference Example 1-2

Reference Example 1-1 rac-ethyl [(3R,4R)-3-methyl-3,4-dihydro-2H-pyrano[3,2-b]pyridin-4-yl]acetate

Reference Example 1-2 rac-ethyl [(3S,4R)-3-methyl-3,4-dihydro-2H-pyrano[3,2-b]pyridin-4-yl]acetate

[Chemical Formula 53]

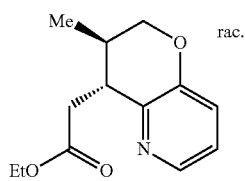

Ref. Example 1-1

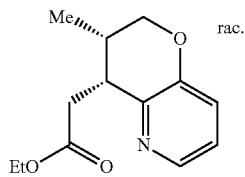

Ref. Example 1-2

To a toluene solution (26.0 mL) of the compound (1.64 g, 5.22 mmol) of Reference Example 2 were added tributyltin hydride (2.58 mL, 8.87 mmol) and azobisisobutyronitrile (0.086 g, 0.522 mmol) at room temperature. After stirring at 90° C. for 1 hr, the reaction mixture was concentrated. The residue was separated and purified by silica gel column chromatography (hexane/ethyl acetate) to give the title compounds of Reference Example 1-1 (0.461 g) and Reference Example 1-2 (0.624 g), respectively.

Reference Example 1-1

$^1$H-NMR (400 MHz, CDCl$_3$) δ:8.09 (1H, dd, J=3.7, 2.4 Hz), 7.04-7.02 (2H, m), 4.24-4.15 (3H, m), 4.03 (1H, dd, J=10.7, 4.6 Hz), 3.65 (1H, dt, J=10.2, 4.3 Hz), 3.13 (1H, dd, J=15.8, 6.1 Hz), 2.41 (1H, dd, J=15.8, 8.8 Hz), 2.39-2.32 (1H, m), 1.27 (3H, t, J=7.3 Hz), 0.97 (3H, d, J=7.3 Hz).

Reference Example 1-2

$^1$H-NMR (400 MHz, CDCl$_3$)

δ:8.12 (1H, dd, J=4.6, 1.5 Hz), 7.07 (1H, dd, J=8.2, 1.5 Hz), 7.02 (1H, dd, J=8.2, 4.6 Hz), 4.19-4.08 (3H, m), 3.85 (1H, dd, J=11.0, 6.7 Hz), 3.10 (1H, dt, J=8.5, 5.5 Hz), 2.93 (1H, dd, J=16.1, 5.2 Hz), 2.67 (1H, dd, J=16.1, 8.2 Hz), 2.11 (1H, dq, J=13.4, 3.3 Hz), 1.23 (3H, t, J=7.0 Hz), 1.08 (3H, d, J=6.7 Hz).

Reference Example 2 rac-ethyl (2E)-5-[(2-bromopyridin-3-yl)oxy]-4-methylpent-2-enoate

[Chemical Formula 54]

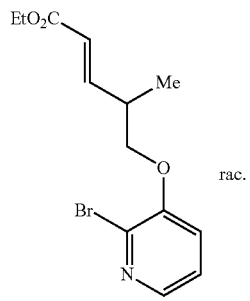

To a mixture of the compound (1.72 g, 7.05 mmol) of Reference Example 3 and toluene (23.5 mL) was added ethyl (triphenylphosphoranylidene)acetate (2.58 g, 7.40 mmol) at room temperature. After stirring at 90° C. for 2 hr, the reaction solution was concentrated. The residue was separated and purified by silica gel column chromatography (hexane/ethyl acetate) to give the title compound (1.64 g).

$^1$H-NMR (400 MHz, CDCl$_3$)

δ:7.98 (1H, dd, J=4.6, 1.2 Hz), 7.18 (1H, dd, J=8.2, 4.6 Hz), 7.08 (1H, dd, J=8.2, 1.2 Hz), 6.99 (1H, dd, J=15.8, 7.3 Hz), 5.95 (1H, dd, J=15.8, 1.2 Hz), 4.19 (2H, q, J=7.1 Hz), 3.97 (1H, dd, J=8.8, 6.4 Hz), 3.91 (1H, dd, J=8.8, 6.4 Hz), 2.97-2.86 (1H, m), 1.28 (3H, t, J=7.1 Hz), 1.26 (3H, d, J=7.3 Hz).

Reference Example 3 rac-3-[(2-bromopyridin-3-yl)oxy]-2-methylpropanal

[Chemical Formula 55]

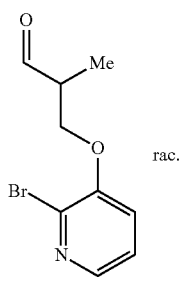

To a mixture of the compound (3.65 g, 14.8 mmol) of Reference Example 4 and chloroform (49.4 mL) was added Dess-Martin periodinane (3.59 g, 8.45 mmol) at room temperature. After stirring at room temperature for 1 hr, to the reaction mixture were added saturated aqueous sodium hydrogencarbonate solution (30 mL) and saturated aqueous sodium thiosulfate solution (30 mL) under ice-cooling, the mixture was subjected to extraction with chloroform (50 mL×twice), and the organic layer was dried over anhydrous magnesium sulfate, filtered, and concentrated. The concentrated residue was separated and purified by silica gel column chromatography (hexane/ethyl acetate) to give the title compound (1.72 g).

$^1$H-NMR (400 MHz, CDCl$_3$)

δ:9.83 (1H, t, J=2.4 Hz), 8.00 (1H, dd, J=4.9, 1.8 Hz), 7.21 (1H, dd, J=7.9, 4.9 Hz), 7.16 (1H, dd, J=7.9, 1.8 Hz), 4.25 (1H, dd, J=9.1, 5.5 Hz), 4.16 (1H, d d, J=9.1, 5.5 Hz), 2.94 (1H, dq, J=7.3, 5.5 Hz), 1.35 (3H, d, J=7.3 Hz).

Reference Example 4 rac-3-[(2-bromopyridin-3-yl)oxy]-2-methylpropan-1-ol

[Chemical Formula 56]

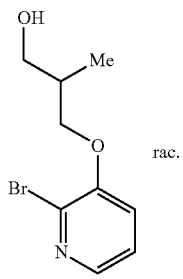

To a mixture of 2-methyl-1,3-propanediol (1.13 g, 12.6 mmol), 2-bromo-3-hydroxypyridine (2.19 g, 12.6 mmol), triphenylphosphine (3.30 g, 12.6 mmol) and N,N-dimethylformamide (9.75 mL) was added diisopropyl azodicarboxylate (2.45 mL, 12.6 mmol) under ice-cooling. After stirring at room temperature 5 hr, methanol was added thereto, and the mixture was concentrated. The residue was separated and purified by silica gel column chromatography (hexane/ethyl acetate) to give the title compound (3.65 g).

¹H-NMR (400 MHz, CDCl₃)

δ:7.96 (1H, dd, J=4.6, 1.5 Hz), 7.19 (1H, dd, J=7.9, 4.6 Hz), 7.13 (1H, dd, J=7.9, 1.5 Hz), 4.05 (1H, dd, J=8.8, 5.2 Hz), 3.98 (1H, dd, J=8.8, 6.7 Hz), 3.78-3.69 (2H, m), 2.32-2.21 (1H, m), 1.30-1.20 (1H, m), 1.07 (3H, d, J=6.7 Hz).

Reference Example 5 rac-tert-butyl {[(3S,4S)-3-methyl-3,4-dihydro-2H-pyrano[3,2-b]pyridin-4-yl]methyl}carbamate

[Chemical Formula 57]

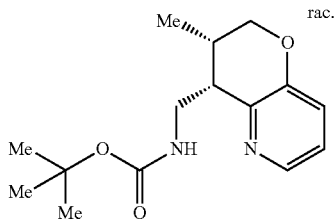

To a chloroform solution (1.0 mL) of the compound (22.0 mg) of Example 2 were added triethylamine (0.049 mL) and di-tert-butyl dicarbonate (0.041 mL). After stirring at room temperature for 2 hr, the mixture was separated and purified by silica gel column chromatography (hexane/ethyl acetate) to give the title compound (20.4 mg).

¹H-NMR (400 MHz, CDCl₃) δ:8.17 (1H, dd, J=4.6, 1.5 Hz), 7.30-7.15 (2H, m), 5.71 (1H, brs), 4.30-4.20 (1H, m), 3.96-3.86 (1H, m), 3.82-3.73 (1H, m), 3.49-3.40 (1H, m), 2.90-2.79 (1H, m), 2.15-2.08 (1H, m), 1.42 (9H, s), 1.12 (3H, d, J=6.7 Hz).

Reference Example 6-1, Reference Example 6-2

Reference Example 6-1 tert-butyl {[(2R,4S)-2-methyl-3,4-dihydro-2H-pyrano[3,2-b]pyridin-4-yl]methyl}carbamate Reference Example 6-2 tert-butyl {[(2R,4R)-2-methyl-3,4-dihydro-2H-pyrano[3,2-b]pyridin-4-yl]methyl}carbamate

[Chemical Formula 58]

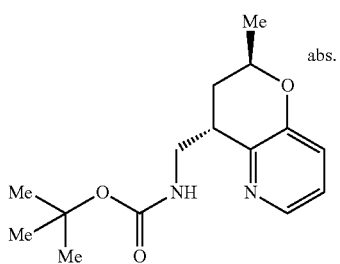

Ref. Example 6-1

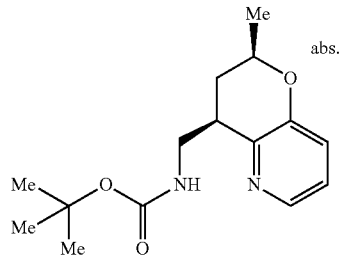

Ref. Example 6-2

To a mixture of the compound (5.37 g, 24.3 mmol) of Reference Example 7, methanol (53.9 mL) and water (27.0 mL) was added sodium hydroxide (1.94 g, 48.5 mmol) at room temperature. After stirring at 60° C. for 2 hr, to the reaction mixture was added 3 mol/L hydrochloric acid until the aqueous layer reached pH5. The reaction solution was concentrated, and the concentrated residue was dissolved in methanol. The insoluble material was filtered off, and the filtrate was concentrated.

To a toluene solution (400 mL) of the obtained residue (5.79 g) were added triethylamine (11.7 mL, 84.0 mmol) and diphenylphosphoryl azide (12.0 mL, 55.9 mmol) at room temperature. After stirring at room temperature for 30 min, the reaction mixture was stirred at 90° C. for 1 hr. To the reaction mixture was added dropwise 5 mol/L aqueous sodium hydroxide solution (84.0 mL) under ice-cooling. The reaction mixture was over 2 hr warmed to room temperature, adjusted to pH7 with 6 mol/L hydrochloric acid, and concentrated. The concentrated residue was dissolved in methanol. The insoluble material was filtered off, and the filtrate was concentrated. To a mixture of the concentrated residue and chloroform (100 mL) were added triethylamine (11.7 mL, 84.0 mmol) and di-tert-butyl dicarbonate (18.3 g, 84.0 mmol). After stirring at room temperature for 1 hr, to the reaction mixture was added water (100 mL), the mixture was subjected to extraction with chloroform (100 mL×twice), and the organic layer was dried over anhydrous magnesium sulfate, filtered, and concentrated. The concentrated residue was separated and purified by silica gel column chromatography (hexane/ethyl acetate) to give the title compounds of Reference Example 6-1 (1.32 g) and Reference Example 6-2 (3.34 g), respectively.

Reference Example 6-1

¹H-NMR (400 MHz, CDCl₃)

δ:8.06 (1H, dd, J=4.3, 1.2 Hz), 7.04 (1H, dd, J=8.3, 1.2 Hz), 6.98 (1H, dd, J=8.3, 4.3 Hz), 5.35 (1H, brs), 4.27-4.20 (1H, m), 3.56-3.50 (1H, m), 3.36-3.30 (1H, m), 2.94-2.88 (1H, m), 1.94 (1H, ddd, J=14.8, 6.0, 2.4 Hz), 1.79 (1H, ddd, J=14.8, 7.2, 6.4 Hz), 1.38 (9H, s), 1.32 (3H, d, J=6.1 Hz).

Reference Example 6-2

¹H-NMR (400 MHz, CDCl₃) δ:8.11 (1H, dd, J=3.7, 2.4 Hz), 7.07-7.06 (2H, m), 5.95 (1H, brs), 4.23 (1H, ddd, J=11.6, 6.7, 1.6 Hz), 3.79-3.73 (1H, m), 3.37-3.31 (1H, m), 3.16-3.08 (1H, m), 2.10 (1H, ddd, J=13.4, 5.5, 1.8 Hz), 1.69-1.60 (1H, m), 1.45 (9H, s), 1.41 (3H, d, J=6.7 Hz).

Reference Example 7 methyl [(2R)-2-methyl-3,4-dihydro-2H-pyrano[3,2-b]pyridin-4-yl]acetate

[Chemical Formula 59]

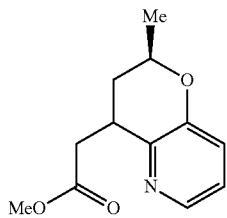

To a toluene solution (132 mL) of the compound (7.90 g, 26.3 mmol) of Reference Example 8 were added tributyltin hydride (11.7 mL, 44.7 mmol) and azobisisobutyronitrile (0.432 g, 2.63 mmol) at room temperature. After stirring at 90° C. for 1 hr, the reaction mixture was concentrated. The residue was separated and purified by silica gel column chromatography (hexane/ethyl acetate) to give the title compound (5.37 g) as a diastereomeric mixture (3:1).
Major Diastereomer
$^1$H-NMR (400 MHz, CDCl$_3$) δ:8.09 (1H, dd, J=4.3, 1.8 Hz), 7.09-7.03 (2H, m), 4.27-4.18 (1H, m), 3.70 (3H, s), 3.53-3.45 (1H, m), 3.36 (1H, dd, J=16.2, 4.6 Hz), 2.26 (1H, ddd, J=13.4, 6.1, 1.8H z), 2.00-1.96 (1H, m), 1.64-1.53 (1H, m), 1.40 (3H, d, J=6.1 Hz).

Reference Example 8 ethyl (2E,5R)-5-[(2-bromopyridin-3-yl)oxy]hex-2-enoate

[Chemical Formula 60]

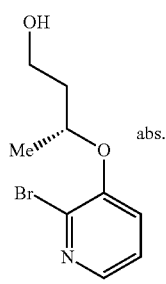

To a mixture of the compound (8.91 g, 36.2 mmol) of Reference Example 9 and chloroform (120 mL) was added Dess-Martin periodinane (21.5 g, 50.7 mmol) under ice-cooling. After stirring at room temperature for 1 hr, to the reaction mixture were added saturated aqueous sodium hydrogencarbonate solution (75 mL) and saturated aqueous sodium thiosulfate solution (75 mL) under ice-cooling, the mixture was subjected to extraction with chloroform (75 mL×twice), and the organic layer was dried over anhydrous magnesium sulfate, filtered, and concentrated. To a mixture of the concentrated residue and toluene (100 mL) was added ethyl (triphenylphosphoranylidene)acetate (12.7 g, 38.0 mmol) at room temperature. After stirring at 80° C. for 2 hr, the reaction mixture was concentrated. The residue was separated and purified by silica gel column chromatography (hexane/ethyl acetate) to give the title compound (7.90 g).
$^1$H-NMR (400 MHz, CDCl$_3$)
δ:7.98 (1H, dd, J=4.6, 1.8 Hz), 7.18 (1H, dd, J=7.9, 4.6 Hz), 7.11 (1H, dd, J=7.9, 1.8 Hz), 7.02-6.94 (1H, m), 5.95-5.91 (1H, m), 4.52-4.48 (1H, m), 4.17 (2H, q, J=7.1 Hz), 2.71-2.64 (1H, m), 2.60-2.53 (1H, m), 1.37 (3H, d, J=6.1 Hz), 1.27 (3H, t, J=7.3 Hz).

Reference Example 9

(3R)-3-[(2-bromopyridin-3-yl)oxy]butan-1-ol

[Chemical Formula 61]

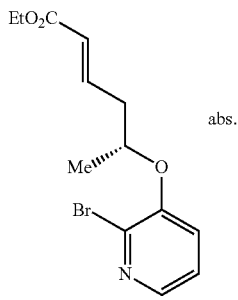

To a mixture of the compound (13.5 g, 37.5 mmol) of Reference Example 10 and methanol (135 mL) was added 6 mol/L hydrochloric acid (18.7 mL) under ice-cooling. After stirring at room temperature for 2 hr, to the reaction mixture was added saturated aqueous sodium hydrogencarbonate solution (250 mL) under ice-cooling, the mixture was subjected to extraction with chloroform (150 mL×three times), and the organic layer was dried over anhydrous magnesium sulfate, filtered, and concentrated. The residue was separated and purified by silica gel column chromatography (hexane/ethyl acetate) to give the title compound (8.91 g).
$^1$H-NMR (400 MHz, CDCl$_3$) δ:7.90 (1H, dd, J=4.0, 2.1 Hz), 7.17-7.11 (2H, m), 4.60-4.58 (1H, m), 3.84-3.71 (2H, m), 2.01-1.83 (2H, m), 1.30 (3H, d, J=6.1 Hz).

Reference Example 10

2-bromo-3-{[(2R)-4-{[tert-butyl(dimethyl)silyl]oxy}butan-2-yl] oxy}pyridine

[Chemical Formula 62]

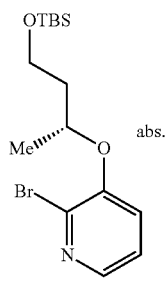

To a mixture of (S)-4-((tert-butyldimethylsilyl)oxy)-2-butanol (8.22 g, 40.2 mmol), 2-bromo-3-hydroxypyridine (7.00 g, 40.2 mmol), triphenylphosphine (11.6 g, 44.3 mmol) and tetrahydrofuran (134 mL) was added diisopropyl azodicarboxylate (8.60 mL, 44.3 mmol) under ice-cooling. After stirring at room temperature for 15 hr, to the reaction mixture was added methanol, and the mixture was concentrated. The concentrated residue was separated and purified by silica gel column chromatography (hexane/ethyl acetate), followed by concentration to give the title compound (13.5 g).

$^1$H-NMR (400 MHz, CDCl$_3$)
δ:7.93 (1H, dd, J=4.6, 1.8 Hz), 7.21 (1H, dd, J=8.2, 1.8 Hz), 7.15 (1H, dd, J=8.2, 4.6 Hz), 4.65-4.57 (1H, m), 3.83-3.69 (2H, m), 2.05-1.95 (1H, m), 1.85-1.77 (1H, m), 1.37 (3H, d, J=6.1 Hz), 0.84 (9H, s), 0.00 (3H, s), −0.04 (3H, s).

Reference Example 11 tert-butyl {[(2S,4S)-2-methyl-3,4-dihydro-2H-pyrano[3,2-b]pyridin-4-yl]methyl}carbamate

[Chemical Formula 63]

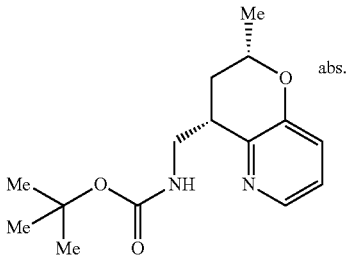

By the same methods as in Reference Example 6-2 to Reference Example 10, the title compound was obtained from (R)-4-((tert-butyldimethylsilyl)oxy)-2-butanol.

$^1$H-NMR (400 MHz, CDCl$_3$) δ:8.13-8.09 (1H, m), 7.10-7.04 (2H, m), 5.92 (1H, brs), 4.26-4.16 (1H, m), 3.80-3.71 (1H, m), 3.40-3.30 (1H, m), 3.16-3.07 (1H, m), 2.13-2.06 (1H, m), 1.70-1.57 (1H, m), 1.43 (9H, s), 1.40 (3H, d, J=6.1 Hz).

Reference Example 12 rac-tert-butyl {[(2R,4S)-2-methyl-3,4-dihydro-2H-pyrano[3,2-b]pyridin-4-yl]methyl}carbamate

[Chemical Formula 64]

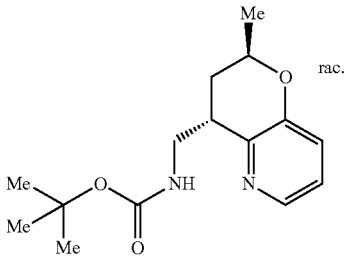

By the same methods as in Reference Example 6-1 to Reference Example 10, the title compound was obtained from 4-((tert-butyldimethylsilyl)oxy)-2-butanol.

$^1$H-NMR (400 MHz, CDCl$_3$) δ:8.12 (1H, dd, J=4.6, 1.5 Hz), 7.22-7.09 (2H, m), 5.54 (1H, brs), 4.39-4.28 (1H, m), 3.64-3.54 (1H, m), 3.46-3.36 (1H, m), 3.14-3.03 (1H, m), 2.04-1.97 (1H, m), 1.88-1.79 (1H, m), 1.42 (9H, s), 1.40 (3H, d, J=6.1 Hz).

Reference Example 13 tert-butyl {[(2R,3S)-6-fluoro-2-methyl-2,3-dihydrofuro[3,2-b]pyridin-3-yl]methyl}carbamate

[Chemical Formula 65]

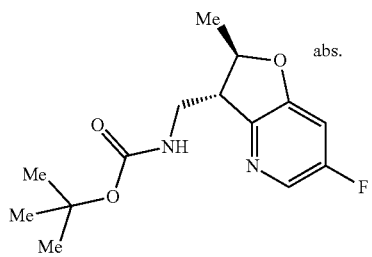

To a toluene solution (13 mL) of the compound (282 mg, 1.33 mmol) of Reference Example 14 were added triethylamine (0.56 mL, 4.00 mmol) and diphenylphosphoryl azide (0.57 mL, 2.67 mmol) at room temperature, and the mixture was stirred at room temperature for 30 min. After stirring at 90° C. for 1 hr, to the reaction mixture was added 5 mol/L aqueous sodium hydroxide solution (4.0 mL, 20.0 mmol) under ice-cooling. After stirring at room temperature for 2 hr, the mixture was neutralized with 12 mol/L hydrochloric acid (1.7 mL). 2-Propanol (10 mL) was added thereto, and the mixture was concentrated. The concentrated residue was dissolved in methanol. The insoluble material was filtered off, and the filtrate was concentrated. To a mixture of the concentrated residue and chloroform (5.0 mL) were added triethylamine (0.56 mL, 4.0 mmol) and di-tert-butyl dicarbonate (873 mg, 4.0 mmol). After stirring at room temperature for 4 hr, the reaction mixture was concentrated. The concentrated residue was separated and purified by silica gel column chromatography (hexane/ethyl acetate) to give the title compound (98 mg).

$^1$H-NMR (400 MHz, CDCl$_3$) δ:7.91 (1H, s), 6.80-6.75 (1H, m), 5.33-5.23 (1H, m), 4.79-4.72 (1H, m), 3.69-3.59 (1H, m), 3.405-3.35 (1H, m), 3.19-3.12 (1H, m), 1.54 (3H, d, J=6.7).

Reference Example 14

[(2R,3S)-6-fluoro-2-methyl-2,3-dihydrofuro[3,2-b]pyridin-3-yl]acetic acid

[Chemical Formula 66]

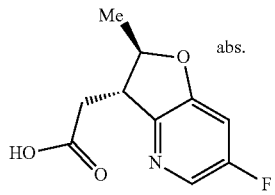

To a mixture of the compound (375 mg, 2.6 mmol) of Reference Example 40, 2-bromo-5-fluoropyridin-3-ol (500 mg, 2.60 mmol), triphenylphosphine (751 mg, 2.86 mmol) and tetrahydrofuran (8.7 mL) was added bis(2-methoxyethyl) azodicarboxylate (671 mg, 2.86 mmol) under ice-cooling. After stirring at room temperature for 2 hr, to the reaction mixture was added methanol, and the mixture was concentrated. To the concentrated residue was added toluene (500 mL), the mixture was washed with water (200 mL×three times), and the organic layer was dried over anhydrous magnesium sulfate, filtered, and concentrated. To a toluene solution (9.0 mL) of the concentrated residue were added tributyltin hydride (1.16 mL, 4.42 mmol) and azobisisobutyronitrile (42.7 mg, 0.26 mmol) at room temperature. After stirring at 90° C. for 1 hr, the reaction mixture was concentrated. To a mixture of the concentrated residue and tetrahydrofuran (10 mL) was added 4 mol/L aqueous sodium hydroxide solution (2.08 mL, 10.4 mmol) at room temperature. After stirring at 60° C. for 4 hr, to the reaction mixture was added water (10 mL), and the aqueous layer was washed with diethyl ether (10 mL×twice). Then, 4 mol/L hydrochloric acid (10.4 mL) was added to the aqueous layer until the layer reached pH5, and the mixture was subjected to extraction with chloroform (200 mL×five times). The combined organic layers were dried over anhydrous magnesium sulfate, filtered, and concentrated to give the title compound (281 mg).

$^1$H-NMR (400 MHz, CDCl$_3$) δ:7.91 (1H, s), 6.88-6.84 (1H, m), 4.75-4.67 (1H, m), 3.50-3.42 (1H, m), 2.94 (1H, dd, J=16.0, 8.0 Hz), 2.68 (1H, dd, J=16.0, 6.4 Hz), 1.37 (3H, d, J=6.7 Hz).

Reference Example 15 rac-tert-butyl [(3,4-dihydro-2H-thiopyrano[3,2-b]pyridin-4-yl)methyl]carbamate

[Chemical Formula 67]

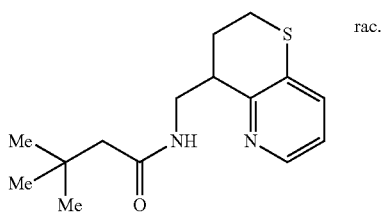

To a mixture of the compound (980 mg, 4.39 mmol) of Reference Example 16, methanol (9.8 mL) and water (4.9 mL) was added sodium hydroxide (351 mg, 8.78 mmol) at room temperature. After stirring at 60° C. for 2 hr, 3 mol/L hydrochloric acid was added to the aqueous layer under ice-cooling until the layer reached pH5. The reaction mixture was concentrated, and the concentrated residue was dissolved in methanol. The insoluble material was filtered off, and the filtrate was concentrated.

To a toluene solution (35.0 mL) of the obtained compound (1.10 g) were added triethylamine (2.20 mL, 15.8 mmol) and diphenylphosphoryl azide (2.26 mL, 10.5 mmol) at room temperature, and the mixture was stirred at room temperature for 30 min. After stirring at 90° C. for 1 hr, to the reaction mixture was added dropwise 5 mol/L aqueous sodium hydroxide solution (17.9 mL) under ice-cooling. The reaction mixture was warmed to room temperature over 2 hr, neutralized with 6 mol/L hydrochloric acid, and concentrated. The concentrated residue was dissolved in methanol. The insoluble material was filtered off, and the filtrate was concentrated. To a mixture of the concentrated residue and chloroform (30 mL) were added triethylamine (2.20 mL, 15.8 mmol) and ditert-butyl dicarbonate (3.66 g, 15.8 mmol). After stirring at room temperature for 1 hr, to the reaction mixture was added water (50 mL), the mixture was subjected to extraction with chloroform (50 mL×twice), and the organic layer was dried over anhydrous magnesium sulfate, filtered, and concentrated. The concentrated residue was separated and purified by silica gel column chromatography (hexane/ethyl acetate) to give the title compound (560 mg).

$^1$H-NMR (400 MHz, CDCl$_3$)

δ:8.17 (1H, dd, J=4.9, 1.8 Hz), 7.34 (1H, dd, J=7.9, 1.8 Hz), 6.94 (1H, dd, J=7.9, 4.9 Hz), 5.46 (1H, brs), 3.65-3.61 (1H, m), 3.37-3.34 (1H, m), 3.06-2.88 (3H, m), 2.24-2.19 (1H, m), 2.04-2.00 (1H, m), 1.37 (9H, s).

Reference Example 16 rac-methyl (3,4-dihydro-2H-thiopyrano[3,2-b]pyridin-4-yl)acetate

[Chemical Formula 68]

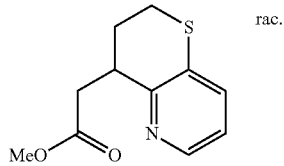

To a mixture of the compound (1.66 g, 6.69 mmol) of Reference Example 17 and chloroform (22.3 mL) was added Dess-Martin periodinane (2.98 g, 7.02 mmol) under ice-cooling. After stirring under ice-cooling for 1 hr, to the reaction mixture was added methyl (triphenylphosphoranylidene)acetate (2.46 g, 7.36 mmol). After stirring at room temperature for 1 hr, to the reaction mixture were added saturated aqueous sodium hydrogencarbonate solution (15 mL) and saturated aqueous sodium thiosulfate solution (15 mL) under ice-cooling, the mixture was subjected to extraction with chloroform (20 mL×twice), and the organic layer was dried over anhydrous magnesium sulfate, filtered, and concentrated. The concentrated residue was separated and purified by silica gel column chromatography (hexane/ethyl acetate), followed by concentration.

To a toluene solution (26.8 mL) of the obtained compound (1.62 g, 5.36 mmol) were added tributyltin hydride (2.39 mL, 9.11 mmol) and azobisisobutyronitrile (0.088 g, 0.536 mmol) at room temperature. After stirring at 90° C. for 1 hr, the reaction mixture was concentrated. The residue was separated and purified by silica gel column chromatography (hexane/ethyl acetate) to give the title compound (0.980 g).

$^1$H-NMR (400 MHz, CDCl$_3$) δ:8.21 (1H, dd, J=4.6, 1.5 Hz), 7.43-7.37 (1H, m), 7.02-6.96 (1H, m), 3.69 (3H, s), 3.09 (1H, dd, J=15.8, 5.5 Hz), 3.06-3.01 (3H, m), 2.60-2.57 (1H, m), 2.32-2.30 (1H, m), 2.15-2.12 (1H, m).

Reference Example 17

3-[(2-bromopyridin-3-yl)sulfanyl]propan-1-ol

[Chemical Formula 69]

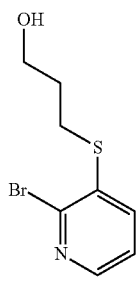

To a mixture of 2-bromo-3-fluoropyridine (3.00 g, 17.1 mmol), 3-mercapto-1-propanol (1.43 g, 15.5 mmol) and N,N-dimethylformamide (15.5 mL) was added potassium carbonate (8.00 g). After stirring at room temperature for 24 hr, the mixture was filtered through Celite, and the filtrate was concentrated. The concentrated residue was separated and purified by silica gel column chromatography (hexane/ethyl acetate) to give the title compound (1.66 g).

$^1$H-NMR (400 MHz, CDCl$_3$)

δ:8.13 (1H, dd, J=4.6, 1.5 Hz), 7.51 (1H, dd, J=7.9, 4.6 Hz), 7.22 (1H, dd, J=7.9, 1.5 Hz), 3.81 (2H, t, J=6.1 Hz), 3.06 (2H, t, J=7.3 Hz), 1.98-1.92 (2H, m).

Reference Examples 18 to 22

According to the methods described in Reference Examples 15 to 17, the compounds of Reference Examples 18 to 22 were obtained from the corresponding compounds, respectively.

TABLE 11

| Ref. No. | Chemical Structure | Instrumental analysis data |
|---|---|---|
| 18 | (structure) rac. | $^1$H-NMR (400 MHz, CDCl$_3$) δ: 8.17 (1H, dd, J = 4.9, 1.2 Hz), 7.45 (1H, dd, J = 7.9, 1.8 Hz), 7.01 (1H, dd, J = 7.9, 4.9 Hz), 5.47 (1H, brs), 3.76-3.66 (1H, m), 3.61-3.46 (2H, m), 3.43 (1H, dd, J = 11.0, 8.5 Hz), 3.19 (1H, dd, J = 11.3, 8.8 Hz), 1.43 (9 H, s). |
| 19 | (structure) rac. | $^1$H-NMR (400 MHz, CDCl$_3$) δ: 7.36 (1H, d, J = 7.9 Hz), 6.90 (1H, d, J = 7.9 Hz), 5.46 (1H, brs), 3.76-3.65 (1H, m), 3.59-3.43 (3H, m), 3.20 (1H, dd, J = 11.0, 7.9 Hz), 2.49 (3H, s), 1.47 (9H, s). |
| 20 | (structure) rac. | $^1$H-NMR (400 MHz, CDCl$_3$) δ: 7.23 (1H, d, J = 7.9 Hz), 6.81 (1H, d, J = 7.9 Hz), 5.51 (1H, brs), 3.64-3.55 (1H, m), 3.37-3.28 (1H, m), 3.05-2.83 (3H, m), 2.39 (3H, s), 2.23-2.13 (1H, m), 2.07-1.99 (1H, m), 1.38 (9H, s). |
| 21 | (structure) rac. | LC-MS: R.T. = 1.612 min ObsMS = 281 [M − 13] |

TABLE 11-continued

| Ref. No. | Chemical Structure | Instrumental analysis data |
|---|---|---|
| 22 | ![structure] rac. | LC-MS: R.T. = 1.32 min ObsMS = 295 [M + 1] |
| 23 | ![structure] rac. | LC-MS: R.T. = 1.61 min ObsMS = 281 [M + 1] |
| 24 | ![structure] rac. | LC-MS: R.T. = 1.62 min ObsMS = 281 [M + 1] |

Reference Example 25-1, Reference Example 25-2

Reference Example 25-1 tert-butyl {[(2R,4R)-2,6-dimethyl-3,4-dihydro-2H-pyrano[3,2-b]pyridin-4-yl]methyl}carbamate Reference Example 25-2 tert-butyl {[(2R,4S)-2,6-dimethyl-3,4-dihydro-2H-pyrano[3,2-b]pyridin-4-yl]methyl}carbamate

[Chemical Formula 70]

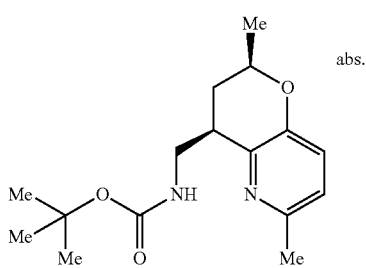

Ref. Example 25-1

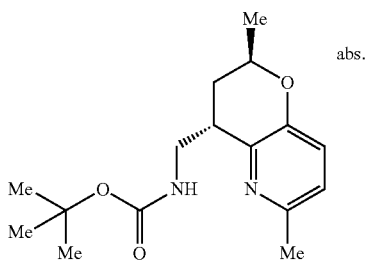

Ref. Example 25-2

By the same methods as in Reference Examples 6-1 and 6-2 to Reference Example 10, the title compounds of Reference Example 25-1 and Reference Example 25-2 were obtained from 2-bromo-3-hydroxy-6-methylpyridine, respectively.

Reference Example 25-1

LC-MS: R.T.=0.745 min ObsMS=293.0 [M+1]

Reference Example 25-2

LC-MS: R.T.=0.650 min ObsMS=294.3 [M+2]

Reference Example 26-1, Reference Example 26-2

Reference Example 26-1 tert-butyl {[(2S,3R)-2-methyl-2,3-dihydrofuro[3,2-b]pyridin-3-yl]methyl}carbamate Reference Example 26-2 tert-butyl {[(2S,3S)-2-methyl-2,3-dihydrofuro[3,2-b]pyridin-3-yl]methyl}carbamate

[Chemical Formula 71]

Ref. Example 26-1

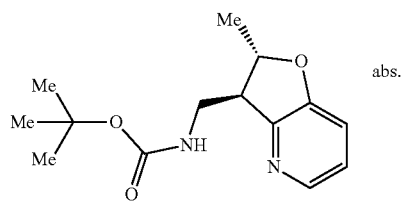

Ref. Example 26-2

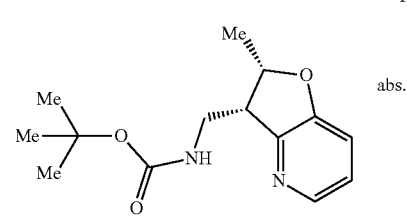

By the same methods as in Reference Example 6-1 and Reference Example 6-2 to Reference Example 7, the title compounds of Reference Example 26-1 and Reference Example 26-2 were obtained from the compound of Reference Example 27, respectively.

Reference Example 26-1

$^1$H-NMR (400 MHz, CDCl$_3$) δ:8.06-8.04 (1H, m), 7.11-7.08 (2H, m), 5.48-5.46 (1H, m), 4.75-4.72 (1H, m), 3.72-3.48 (2H, m), 3.26-3.23 (1H, m), 1.55 (3H, d, J=6.1 Hz), 1.44 (9H, s).

Reference Example 26-2

LC-MS: R.T.=1.42 min ObsMS=265 [M+1]

Reference Example 27 methyl (2E,4S)-4-[(2-bromopyridin-3-yl)oxy]pent-2-enoate

[Chemical Formula 72]

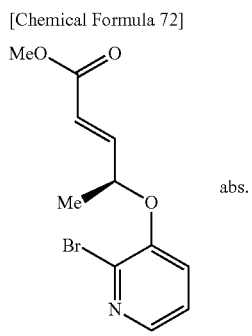

To a mixture of the compound (1.56 g, 6.00 mmol) of Reference Example 28 and dichloromethane (12.0 mL) was added 1.03 mol/L diisobutylaluminium hydride toluene solution (17.47 mL, 17.99 mmol) at −78° C. After stirring at −78° C. for 2 hr, saturated aqueous ammonium chloride (50 mL) was added thereto, and the insoluble material was removed by filtration through Celite. The mixture was subjected to extraction with ethyl acetate, and the organic layer was dried over anhydrous magnesium sulfate, filtered, and concentrated. To a mixture of the concentrated residue and toluene was added ethyl (triphenylphosphoranylidene) acetate (2.005 g, 6.00 mmol) at room temperature. After stirring at room temperature for 1 hr, the reaction mixture was concentrated. The residue was separated and purified by silica gel column chromatography (hexane/ethyl acetate) to give the title compound (0.54 g).

$^1$H-NMR (400 MHz, CDCl$_3$) δ:7.97-7.96 (1H, m), 7.17-7.14 (2H, m), 6.29-6.26 (1H, m), 6.07-6.06 (1H, m), 5.90 (1H, d, J=11.6 Hz), 3.78 (3H, s), 1.57 (5H, d, J=6.1 Hz).

Reference Example 28 methyl (2S)-2-[(2-bromopyridin-3-yl)oxy]propanoate

[Chemical Formula 73]

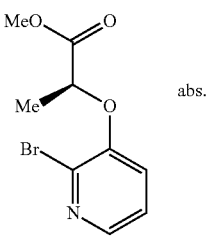

To a mixture of (R)-(+)-methyl lactate (1.20 g, 11.5 mmol), 2-bromo-3-hydroxypyridine (2.00 g, 11.5 mmol), triphenylphosphine (3.32 g, 12.6 mmol) and tetrahydrofuran (38 mL) was added diisopropyl azodicarboxylate (1.83 mL, 12.6 mmol) under ice-cooling. After stirring at room temperature for 15 hr, to the reaction mixture was added methanol, and the mixture was concentrated. The concentrated residue was separated and purified by silica gel column chromatography (hexane/ethyl acetate), followed by concentration to give the title compound (13.5 g).

¹H-NMR (400 MHz, CDCl₃) δ:8.05-8.03 (1H, m), 7.18-7.17 (1H, m), 7.09-7.08 (1H, m), 4.78-4.76 (1H, m), 3.77 (3H, s), 1.72 (3H, d, J=7.3 Hz).

Reference Example 29 rac-tert-butyl {[(2R,3S)-2-(propan-2-yl)-2,3-dihydrofuro[3,2-b]pyridin-3-yl]methyl}carbamate

[Chemical Formula 74]

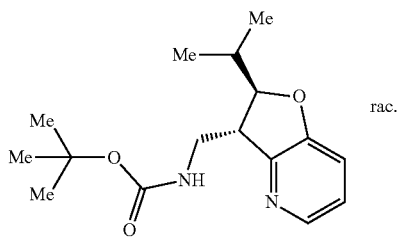

By the same methods as in Reference Example 6-1, Reference Example 6-2 and Reference Example 7, the title compound was obtained from the compound of Reference Example 30.

¹H-NMR (400 MHz, CDCl₃) δ:8.06-8.04 (1H, m), 7.11-7.08 (2H, m), 5.48-5.46 (1H, m), 4.75-4.72 (1H, m), 3.72-3.48 (2H, m), 3.26-3.23 (1H, m), 1.55 (3H, d, J=6.1 Hz), 1.44 (9H, s).

Reference Example 30 rac-methyl (2E)-4-[(2-bromopyridin-3-yl)oxy]-5-methylhex-2-enoate

[Chemical Formula 75]

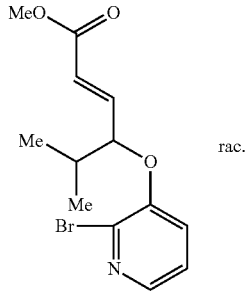

To a mixture of the compound (1.18 g, 4.54 mmol) of Reference Example 31 and dimethyl sulfoxide (15.0 mL) were added triethylamine (1.90 mL, 13.6 mmol) and sulfur trioxide pyridine complex (2.17 g, 13.6 mmol) at room temperature. After stirring at room temperature for 3 hr, to the reaction mixture was added water (200 mL), and the mixture was subjected to extraction with ethyl acetate (200 mL×twice). The organic layer was dried over anhydrous magnesium sulfate, filtered, and concentrated. To a mixture of the concentrated residue and toluene (15 mL) was added ethyl (triphenylphosphoranylidene)acetate (1.72 g, 5.16 mmol) at room temperature. After stirring at room temperature for 12 hr, the reaction solution was concentrated. The residue was separated and purified by silica gel column chromatography (hexane/ethyl acetate) to give the title compound (0.77 g).

¹H-NMR (400 MHz, CDCl₃) δ:7.92-7.91 (1H, m), 7.16-7.14 (1H, m), 7.11-7.09 (1H, m), 6.17-6.14 (1H, m), 6.00-5.97 (1H, m), 5.76-5.75 (1H, m), 3.77 (3H, s), 2.14-2.10 (1H, m), 1.10 (3H, d, J=7.3 Hz), 1.05 (3H, d, J=7.3 Hz).

Reference Example 31 rac-2-[(2-bromopyridin-3-yl)oxy]-3-methylbutan-1-ol

[Chemical Formula 76]

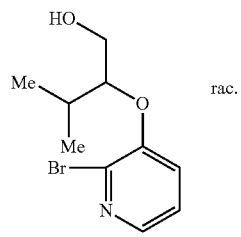

To a mixture of the compound (1.34 g, 4.43 mmol) of Reference Example 32 and tetrahydrofuran (15.0 mL) was added 1.0 mol/L diisobutylaluminium hydride toluene solution (4.88 mL, 4.88 mmol) at −78° C. After stirring at room temperature for 3 hr, 1.0 mol/L diisobutylaluminium hydride toluene solution (4.88 mL, 4.88 mmol) was added thereto under ice-cooling. After stirring under ice-cooling for 2 hr, to the reaction mixture were added water (30 mL) and 10% aqueous potassium hydrogen sulfate solution (30 mL), and the mixture was subjected to extraction with ethyl acetate (50 mL×twice). The organic layer was dried over anhydrous magnesium sulfate, filtered, and concentrated. The concentrated residue was separated and purified by silica gel column chromatography (hexane/ethyl acetate) to give the title compound (1.19 g).

¹H-NMR (400 MHz, CDCl₃) δ:7.97-7.96 (1H, m), 7.30-7.28 (1H, m), 7.18-7.16 (1H, m), 4.17-4.16 (1H, m), 3.87-3.81 (2H, m), 2.14-2.06 (1H, m), 1.05 (3H, d, J=7.3 Hz), 1.00 (3H, d, J=6.7 Hz).

Reference Example 32 rac-methyl 2-[(2-bromopyridin-3-yl)oxy]-3-methylbutanoate

[Chemical Formula 77]

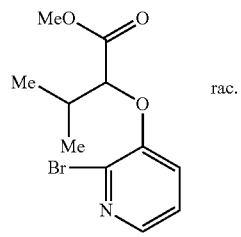

To a mixture of 2-bromo-3-hydroxypyridine (2.00 g, 11.5 mmol) and N,N-dimethylformamide (30 mL) were added potassium carbonate (1.91 g, 13.8 mmol) and ethyl 2-bromo-3-methylbutyrate (2.25 mL, 13.8 mmol). After stirring at 50° C. for 4 hr, to the reaction mixture was added water (200 mL), the mixture was subjected to extraction with ethyl acetate (200 mL×twice), and the organic layer was dried over anhydrous magnesium sulfate, filtered, and concentrated. The concentrated residue was separated and purified by silica gel column chromatography (hexane/ethyl acetate), followed by concentration to give the title compound (1.36 g).

$^1$H-NMR (400 MHz, CDCl$_3$) δ:7.99-7.97 (1H, m), 7.15-7.13 (1H, m), 6.96-6.94 (1H, m), 4.39 (1H, d, J=4.9 Hz), 4.22-4.19 (2H, m), 2.39-2.37 (1H, m), 1.23-1.22 (3H, m), 1.13-1.11 (6H, m).

Reference Examples 33 to 34

According to the methods described in Reference Examples 29 to 32, the compounds of Reference Examples 33 to 34 were obtained from the corresponding compounds, respectively.

Reference Example 35-1, Reference Example 35-2

Reference Example 35-1 rac-tert-butyl {[(2S,4R)-2-phenyl-3,4-dihydro-2H-pyrano[3,2-b]pyridin-4-yl]methyl}carbamate Reference Example 35-2 rac-tert-butyl {[(2S,4S)-2-phenyl-3,4-dihydro-2H-pyrano[3,2-b]pyridin-4-yl]methyl}carbamate

[Chemical Formula 78]

Ref. Example 35-1

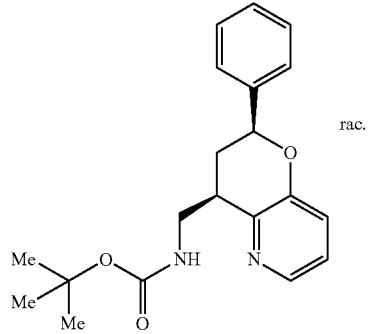

rac.

TABLE 12

| Ref. No. | Chemical Structure | | Instrumental analysis data |
|---|---|---|---|
| 33 | 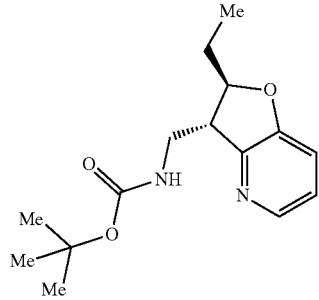 | rac. | $^1$H-NMR (400 MHz, DMSO-D$_6$) δ: 8.36-8.05 (4H, m), 7.35-7.25 (2H, m), 4.85-4.77 (1H, s), 3.59-3.55 (1H, m), 3.30-3.15 (2H, m), 1.85-1.70 (2H, m), 0.97 (3H, t, J = 6.7 Hz). |
| 34 | 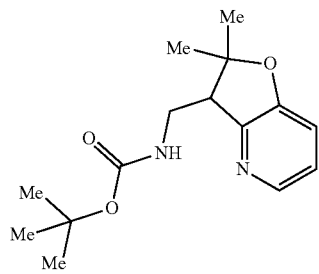 | rac. | $^1$H-NMR (400 MHz, CDCl$_3$) δ: 8.02 (1H, dd, J = 4.9, 1.2 Hz), 7.16-7.02 (2H, m), 6.12 (1H, brs), 3.80-3.67 (1H, m) 3.34-3.19 (2H, m), 1.53 (3H, s), 1.44 (9H, s), 1.39 (3H, s). |

Ref. Example 35-2

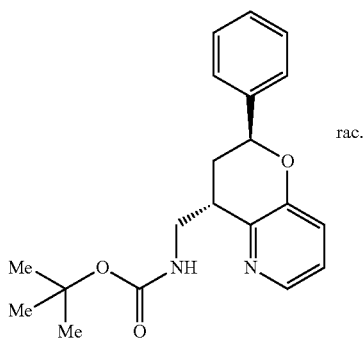

By the same methods as in Reference Example 6-1 and Reference Example 6-2 to Reference Example 10, the title compounds of Reference Example 35-1 and Reference Example 35-2 were obtained from 3-((tert-butyldimethylsilyl)oxy)-1-phenyl-1-propanol, respectively.

Reference Example 35-1

$^1$H-NMR (400 MHz, CDCl$_3$) δ:8.22-8.18 (1H, m), 7.46-7.31 (5H, m), 7.26-7.12 (2H, m), 6.01 (1H, brs), 5.14 (1H, dd, J=11.6, 1.8 Hz), 3.87-3.76 (1H, m), 3.51-3.40 (1H, m), 3.40-3.31 (1H, m), 2.40-2.32 (1H, m), 2.07-1.96 (1H, m), 1.44 (9H, s).

Reference Example 35-2

$^1$H-NMR (400 MHz, CDCl$_3$) δ:8.23-8.18 (1H, m), 7.53-7.30 (7H, m), 5.68-5.47 (1H, m), 5.44-5.30 (1H, m), 3.81-3.71 (1H, m), 3.69-3.51 (1H, m), 3.44-3.09 (1H, m), 2.34-2.25 (1H, m), 2.22-2.11 (1H, m), 1.45-1.41 (9H, m).

Reference Example 36 rac-tert-butyl {[(2S,3S)-2-(hydroxymethyl)-2,3-dihydrofuro[3,2-b]pyridin-3-yl]methyl}carbamate

[Chemical Formula 79]

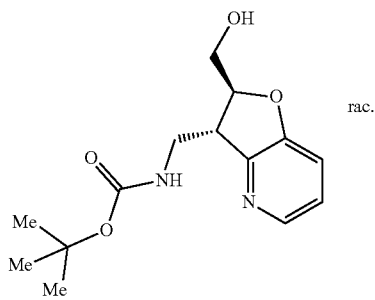

To a dichloromethane suspension (2.0 mL) of the compound (42.0 mg, 0.157 mmol) of Example 32 were added triethylamine (0.044 mL, 0.314 mmol) and 1.0 mol/L boron tribromide dichloromethane solution (0.330 mL, 0.330 mmol) under ice-cooling. After stirring at room temperature for 4 hr, to the reaction mixture was added methanol (2.0 mL) under ice-cooling. After stirring under ice-cooling for 10 min, the reaction mixture was concentrated. To a mixture of the concentrated residue, tetrahydrofuran (1.0 mL) and water (1.0 mL) were added potassium carbonate (217 mg, 1.57 mmol) and di-tert-butyl dicarbonate (51.5 mg, 0.236 mmol). After stirring at room temperature for 3 hr, to the reaction mixture was added water (30 mL), the mixture was subjected to extraction with ethyl acetate (30 mL×twice), and the organic layer was dried over anhydrous magnesium sulfate, filtered, and concentrated. The residue was separated and purified by silica gel column chromatography (hexane/ethyl acetate) to give the title compound (22.9 mg).

$^1$H-NMR (400 MHz, CDCl$_3$) δ:8.06 (1H, dd, J=4.3, 2.4 Hz), 7.19-7.13 (2H, m), 5.44 (1H, brs), 4.79 (1H, m), 3.98 (1H, dd, J=12.5, 3.4 Hz), 3.86 (1H, dd, J=12.2, 4.9 Hz), 3.79-3.69 (1H, m), 3.67-3.53 (2H, m), 1.41 (9H, s).

Reference Example 37 benzyl {[(2R,3S)-2-methyl-2,3-dihydrofuro[3,2-b]pyridin-3-yl]methyl}carbamate

[Chemical Formula 80]

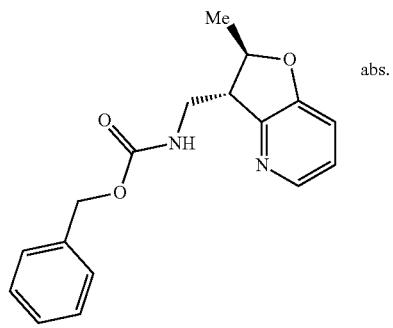

To a toluene solution (208 mL) of the compound (28.1 g, 145 mmol) of Reference Example 38 were added triethylamine (30.4 mL, 218 mmol) and diphenylphosphoryl azide (37.5 mL, 175 mmol) at room temperature, and the mixture was stirred at room temperature for 30 min. After stirring at 90° C. for 1 hr, to the reaction mixture was added benzyl alcohol (22.5 mL, 218 mmol). After stirring at 90° C. for 3 hr, to the reaction mixture was added saturated aqueous sodium hydrogencarbonate solution (250 mL) under ice-cooling, the mixture was subjected to extraction with ethyl acetate (150 mL×twice), and the organic layer was dried over anhydrous magnesium sulfate, filtered, and concentrated. The concentrated residue was separated and purified by silica gel column chromatography (hexane/ethyl acetate), followed by concentration to give the title compound (23.6 g) as a diastereomeric mixture (10:1).

Major Diastereomer $^1$H-NMR (400 MHz, CDCl$_3$) δ:8.00 (1H, dd, J=4.6, 1.5 Hz), 7.40-7.29 (5H, m), 7.17-7.05 (2H, m), 5.84 (1H, brs), 5.09 (2H, s), 4.76-4.68 (1H, m), 3.84-3.76 (1H, m), 3.54-3.46 (1H, m), 3.31-3.25 (1H, m), 1.52 (3H, d, J=6.1 Hz).

Reference Example 38 tert-butyl {[(2S,4S)-2-phenyl-3,4-dihydro-2H-pyrano[3,2-b]pyridin-4-yl]methyl}carbamate

[Chemical Formula 81]

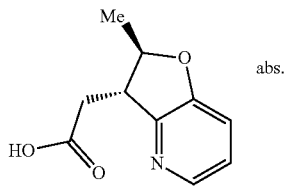

To a toluene solution (499 mL) of the compound (45.0 g, 150 mmol) of Reference Example 39 were added tributyltin hydride (66.8 mL, 255 mmol) and azobisisobutyronitrile (2.46 g, 15.0 mmol) at room temperature. After stirring at 90° C. for 1 hr, the reaction mixture was concentrated. To a mixture of the concentrated residue, tetrahydrofuran (333 mL) and water (167 mL) was added sodium hydroxide (24.0 g, 599 mmol) at room temperature. After stirring at 60° C. 3 hr, to the reaction mixture was added water (333 mL), and the aqueous layer was washed with diethyl ether (167 mL×twice). Then, 5 mol/L hydrochloric acid (120 mL) was added to the aqueous layer until the layer reached pH5, and the mixture was subjected to extraction with chloroform (200 mL×five times). The combined organic layers were dried over anhydrous magnesium sulfate, filtered, and concentrated to give the title compound (28.1 g) as a diastereomeric mixture (10:1).

Major Diastereomer $^1$H-NMR (400 MHz, CDCl$_3$) δ:8.02 (1H, dd, J=4.9, 1.2 Hz), 7.18-7.11 (2H, m), 4.61-4.53 (1H, m), 3.51 (1H, dt, J=9.4, 4.9 Hz), 2.89 (1H, dd, J=15.8, 9.4 Hz), 2.71 (1H, dd, J=15.8, 4.9 Hz), 1.61 (3H, d, J=6.7 Hz).

Reference Example 39 ethyl (2E,4R)-4-[(2-bromopyridin-3-yl)oxy]pent-2-enoate

[Chemical Formula 82]

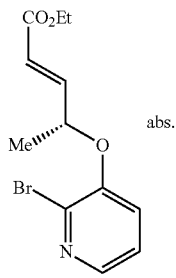

To a mixture of the compound (26.0 g, 180 mmol) of Reference Example 40, 2-bromo-3-hydroxypyridine (31.4 g, 180 mmol), triphenylphosphine (52.0 g, 198 mmol) and tetrahydrofuran (515 mL) was added bis(2-methoxyethyl)azodicarboxylate (46.5 g, 198 mmol) under ice-cooling. After stirring at room temperature for 2 hr, to the reaction mixture was added methanol, and the mixture was concentrated. To the concentrated residue was added toluene (500 mL), the mixture was washed with water (200 mL×three times), and the organic layer was dried over anhydrous magnesium sulfate, filtered, and concentrated. To the concentrated residue were added hexane/diethyl ether (4/1, 250 mL), the precipitated solid was filtered off, and the filtrate was concentrated. The concentrated residue was separated and purified by silica gel column chromatography (hexane/ethyl acetate), followed by concentration to give the title compound (45.0 g).

$^1$H-NMR (400 MHz, CDCl$_3$)

δ:7.99 (1H, dd, J=4.9, 1.8 Hz), 7.16 (1H, dd, J=8.2, 4.9 Hz), 7.06 (1H, dd, J=8.2, 1.8 Hz), 6.96 (1H, dd, J=15.2, 4.9 Hz), 6.06 (1H, dd, J=15.2, 1.8 Hz), 4.96-4.92 (1H, m), 4.18 (2H, dq, J=7.0, 1.2 Hz), 1.55 (3H, d, J=6.1 Hz), 1.27 (3H, t, J=7.0 Hz).

Reference Example 40 ethyl (2E,4S)-4-hydroxypent-2-enoate

[Chemical Formula 83]

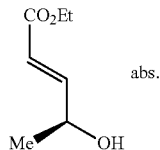

To a mixture of the compound (23.8 g, 167 mmol) of Reference Example 41 and methanol (478 mL) was added sodium borohydride (7.59 g, 201 mmol) at −35° C. The mixture was warmed to 0° C. over 1 hr, and to the reaction mixture was added saturated aqueous ammonium chloride solution (500 mL) under ice-cooling. The mixture was subjected to extraction with ethyl acetate (500 mL×three times), and the organic layer was dried over anhydrous magnesium sulfate, filtered, and concentrated. The concentrated residue was separated and purified by silica gel column chromatography (hexane/ethyl acetate), followed by concentration to give the title compound (17.0 g).

$^1$H-NMR (400 MHz, CDCl$_3$)

δ:6.78 (1H, dd, J=15.8, 4.9 Hz), 5.84 (1H, dd, J=15.8, 1.5 Hz), 4.35-4.26 (1H, m), 4.02 (2H, q, J=7.0 Hz), 1.16 (3H, d, J=6.7 Hz), 1.11 (3H, t, J=7.0 Hz).

Reference Example 41 ethyl (4S)-4-hydroxypent-2-ynoate

[Chemical Formula 84]

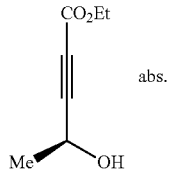

To a mixture of (S)-(−)-3-butyn-2-ol (14.5 g, 207 mmol), bis(trimethylsilyl)amine (18.4 g, 114 mmol) and tetrahydrofuran (104 mL) was added conc. sulfuric acid (0.110 mL) at room temperature. After stirring at 65° C. for 3 hr, the reaction mixture was cooled to −78° C. 2.69 mol/L n-Butyllithium (100 mL, 269 mmol) was added dropwise thereto at −78° C. After stirring at −78° C. for 30 min, a tetrahydrofuran solution (59 mL) of chloroethyl formate (26.6 mL, 279 mmol) was added dropwise thereto. After stirring at −78° C. for 1 hr, the reaction mixture was warmed to room temperature over 1 hr. To the reaction mixture was added 6 mol/L sulfuric acid (108 mL), and the mixture was stirred at room temperature for 15 hr. To the reaction mixture was added water (300 mL), the mixture was subjected to extraction with ethyl acetate (200 mL×three times), and the organic layer was dried over anhydrous magnesium sulfate, filtered, and concentrated. The concentrated residue was separated and purified by silica gel column chromatography (hexane/ethyl acetate), followed by concentration to give the title compound (23.4 g).

$^1$H-NMR (400 MHz, CDCl$_3$)

δ:4.64 (1H, q, J=6.7 Hz), 4.25 (2H, q, J=7.0 Hz), 1.52 (3H, d, J=6.7 Hz), 1.32 (3H, t, J=7.0 Hz).

Reference Examples 42 to 45

According to the methods described in Reference Examples 37 to 39, the compounds of Reference Examples 42 to 45 were obtained from the corresponding compounds, respectively.

TABLE 13

| Ref. No. | Chemical Structure | Instrumental analysis data |
|---|---|---|
| 42 | 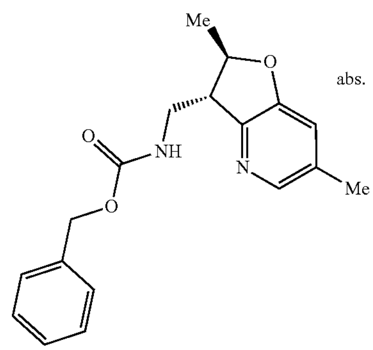 [SMILES: Cc1cnc2c(c1)O[C@H](C)[C@H]2CNC(=O)OCc1ccccc1] | $^1$H-NMR (400 MHz, CDCl$_3$) δ: 7.82 (1H, s), 7.37-7.26 (5H, m), 7.02 (1H, brs), 5.93 (1H, brs), 5.07 (2H, s), 4.85-4.67 (1H, m), 3.88-3.77 (1H, m), 3.60-3.50 (1 H, m), 3.39-3.28 (1H, m), 2.32 (3H, s), 1.52 (3H, d, J = 6.1 Hz). |
| 43 | 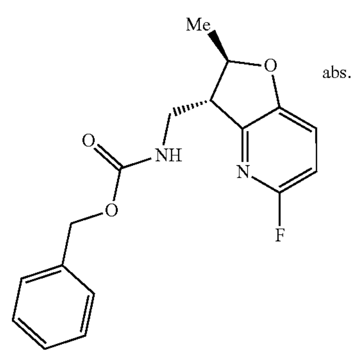 [SMILES: C[C@H]1Oc2ccc(F)nc2[C@@H]1CNC(=O)OCc1ccccc1] | LC-MS: R.T. = 0.953 min ObsMS = 317.2 [M + 1] |
| 44 | 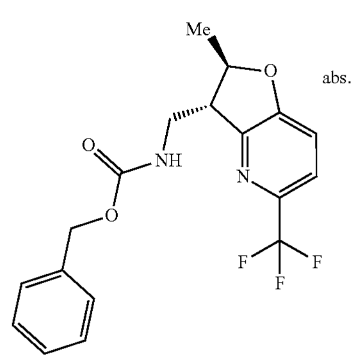 [SMILES: C[C@H]1Oc2ccc(C(F)(F)F)nc2[C@@H]1CNC(=O)OCc1ccccc1] | LC-MS: R.T. = 2.005 min ObsMS = 367.2 [M + 1] |

TABLE 13-continued

| Ref. No. | Chemical Structure | Instrumental analysis data |
|---|---|---|
| 45 | 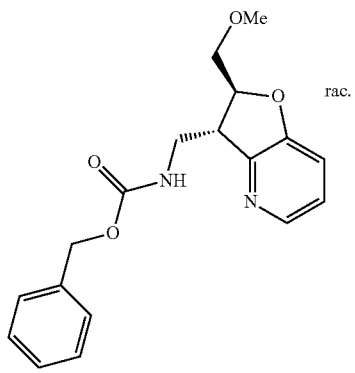 | LC-MS: R.T. = 2.024 min ObsMS = 367.2 [M + 1] |

Reference Example 46 rac-benzyl {[(2S,3S)-2-(methoxymethyl)-2,3-dihydrofuro[3,2-b]pyridin-3-yl]methyl}carbamate

[Chemical Formula 85]

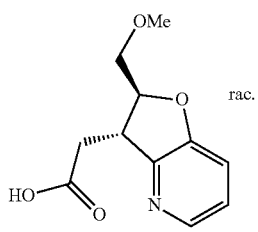

By the same method as in Reference Example 37, the title compound was obtained from the compound of Reference Example 47.

¹H-NMR (400 MHz, CDCl₃) δ:8.02 (1H, dd, J=3.4, 3.4 Hz), 7.36-7.26 (5H, m), 7.10-7.06 (2H, m), 5.75 (1H, brs), 5.09 (2H, s), 4.78-4.70 (1H, m), 3.83-3.72 (1H, m), 3.69-3.62 (2H, m), 3.60-3.47 (2H, m), 3.40 (3H, s).

Reference Example 47 rac-[(2S,3S)-2-(methoxymethyl)-2,3-dihydrofuro[3,2-b]pyridin-3-yl]acetic acid

[Chemical Formula 86]

To a methanol solution (5.0 mL) of the compound (324 mg, 1.37 mmol) of Reference Example 48 were added water (5.0 mL) and sodium hydroxide (546 mg, 13.7 mmol), and the mixture was stirred at room temperature for 30 min. Then, 6 mol/L hydrochloric acid was added to the reaction mixture until the mixture reached pH4, and the mixture was concentrated. The concentrated residue was separated and purified by silica gel column chromatography (chloroform/methanol) to give the title compound (258 mg).

¹H-NMR (400 MHz, CDCl₃) δ:8.05-7.98 (1H, m), 7.23-7.16 (2H, m), 4.69-4.64 (1H, m), 3.89-3.83 (1H, m), 3.79 (1H, dd, J=11.0, 3.0 Hz), 3.70 (1H, dd, J=11.0, 5.5 Hz), 3.42 (3H, s), 2.99 (1H, dd, J=16.5, 8.5 Hz), 2.86 (1H, dd, J=16.1, 5.2 Hz).

Reference Example 48 rac-methyl [(2S,3S)-2-(methoxymethyl)-2,3-dihydrofuro[3,2-b]pyridin-3-yl]acetate

[Chemical Formula 87]

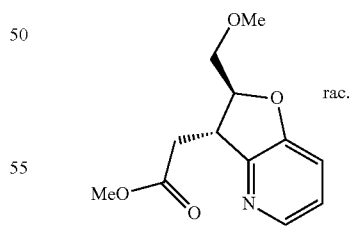

By the same method as in Reference Example 1-1, the title compound was obtained from the compound of Reference Example 49.

¹H-NMR (400 MHz, CDCl₃) δ:8.04 (1H, dd, J=4.3, 1.8 Hz), 7.06-7.00 (2H, m), 4.71 (1H, td, J=6.7, 3.0 Hz), 3.78-3.72 (1H, m), 3.70 (3H, s), 3.69-3.60 (2H, m), 3.42 (3H, s), 3.08 (1H, dd, J=16.8, 4.0 Hz), 2.64 (1H, dd, J=16.8, 10.1 Hz).

Reference Example 49 rac-methyl (2E)-4-[(2-bromopyridin-3-yl)oxy]-5-methoxypent-2-enoate

[Chemical Formula 88]

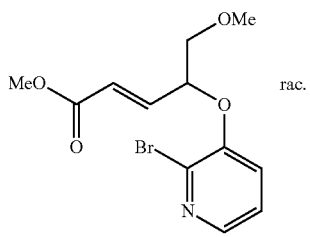

By the same methods as in Reference Example 30 to Reference Example 32, the title compound was obtained from methyl 2-bromo-3-methoxypropanoate.

$^1$H-NMR (400 MHz, CDCl$_3$) δ:8.00 (1H, dd, J=4.3, 1.8 Hz), 7.18-7.12 (2H, m), 6.97 (1H, dd, J=15.8, 4.9 Hz), 6.17 (1H, dd, J=15.8, 1.8 Hz), 5.00-4.94 (1H, m), 3.73 (3H, s), 3.70 (2H, dd, J=5.5, 3.7 Hz), 3.43 (3H, s).

Reference Example 50 rac-[(5aS,9aR,10R)-6,7,8,9,9a,10-hexahydro-5aH-[1]benzpyrano[3,2-b]pyridine-10-yl]acetic acid

[Chemical Formula 89]

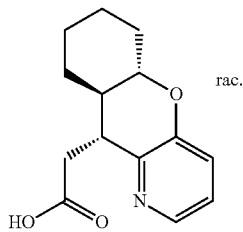

By the same methods as in Reference Example 8 to Reference Example 10 and Reference Example 14, the title compound was obtained from 2-(((tert-butyldimethylsilyl)oxy)methyl)cyclohexan-1-ol.

LC-MS: R.T.=1.353 min ObsMS=248.4 [M+1]

Reference Example 51

[(2R,3S)-2,7-dimethyl-2,3-dihydrofuro[3,2-b]pyridin-3-yl]acetic acid

[Chemical Formula 90]

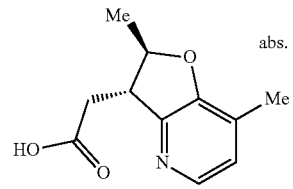

By the same methods as in Reference Example 38 and Reference Example 39, the title compound was obtained from 2-bromo-3-hydroxy-4-methylpyridine.

LC-MS: R.T.=0.449 min ObsMS=208.1 [M+1]

Reference Example 52 tert-butyl {[(2R,3S)-2,5-dimethyl-2,3-dihydrofuro[3,2-b]pyridin-3-yl]methyl}carbamate

[Chemical Formula 91]

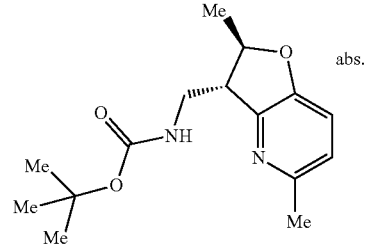

By the same methods as in Reference Example 13 and Reference Example 14, the title compound was obtained from 2-bromo-3-hydroxy-6-methylpyridine.

$^1$H-NMR (400 MHz, CDCl$_3$) δ: 6.91-6.84 (2H, m), 5.37 (1H, brs), 4.66-4.58 (1H, m), 3.71-3.58 (1H, m), 3.45-3.34 (1H, m), 3.10 (1H, dd, J=12.8, 7.3 Hz), 2.45 (3H, s), 1.49 (3H, d, J=6.1H z), 1.43 (9H, s).

Reference Examples 53 to 54

According to the methods described in Reference Examples 38 and 39, the compounds of Reference Examples 53 to 54 were obtained from the corresponding compounds, respectively.

TABLE 14

| Ref. No. | Chemical Structure | Instrumental analysis data |
|---|---|---|
| 53 | 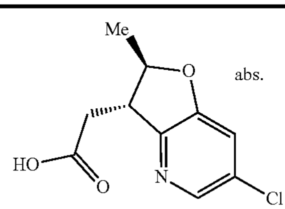 | $^1$H-NMR (400 MHz, CDCl$_3$) δ: 7.99 (1H, d, J = 2.4 Hz), 7.15 (1H, d, J = 1.8 Hz), 4.76-4.68 (1H, m), 3.50 (1H, q, J = 7.1 Hz), 2.94 (1H, dd, J = 16.5, 7.3 Hz), 2.81 (1H, dd, J = 15.8, 6.7 Hz), 1.58 (3H, d, J = 6.1 Hz). |

TABLE 14-continued

| Ref. No. | Chemical Structure | Instrumental analysis data |
|---|---|---|
| 54 | Me, O, abs., HO, O, N, Cl | LC-MS: R.T. = 1.537 min ObaMS = 228.3 [M + 1] |

Reference Example 55 benzyl {[(2R,3S)-6-fluoro-2-methyl-2,3-dihydrofuro[3,2-b]pyridin-3-yl]methyl}methylcarbamate

[Chemical Formula 92]

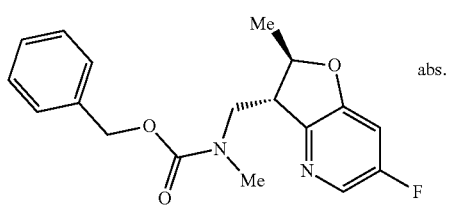

To a suspension of 55% sodium hydride (12.0 g, 276 mmol) in N-methylpyrrolidone (491 mL) was added an N-methylpyrrolidone solution (123 mL) of the compound (58.2 g, 184 mmol) of Reference Example 56 under ice-cooling. After stirring for 30 min, to the reaction mixture was added methyl iodide (23.0 mL, 368 mmol) under ice-cooling, and the mixture was stirred at room temperature for 2 hr. Then, to the reaction mixture was added water (500 mL) under ice-cooling, the mixture was subjected to extraction with ethyl acetate (1000 mL), and the organic layer was washed with water (200 mL×twice), dried over anhydrous sodium sulfate, filtered, and concentrated. The residue was separated and purified by silica gel column chromatography (hexane:ethyl acetate) to give the title compound (39.5 g).

$^1$H-NMR (400 MHz, CDCl$_3$) δ:7.87 (1H, dd, J=2.4, 1.2 Hz), 7.33-7.31 (5H, m), 6.75-6.72 (3H, m), 5.12 (2H, s), 4.92-4.74 (1H, m), 3.80-3.65 (2H, m), 3.25 (1H, br s), 2.92 (3H, d, J=14.6 Hz), 1.40-1.35 (3H, m).

Reference Example 56 benzyl {[(2R,3S)-6-fluoro-2-methyl-2,3-dihydrofuro[3,2-b]pyridin-3-yl]methyl}carbamate

[Chemical Formula 93]

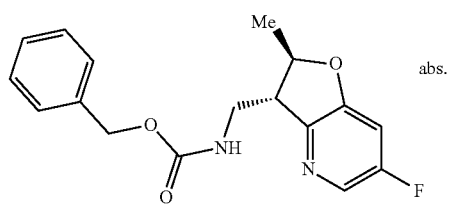

To a toluene solution (227 mL) of the compound (33.6 g, 159 mmol) of Reference Example 14 were added triethylamine (33.2 mL, 239 mmol) and diphenylphosphoryl azide (41.0 mL, 191 mmol) at room temperature. After stirring at room temperature for 1 hr, the reaction solution was heated to 90° C. After stirring at 90° C. for 20 min, to the reaction solution was added benzyl alcohol (18.0 mL, 175 mmol). After stirring at 90° C. for 3.5 hr, to the reaction mixture was added saturated aqueous sodium hydrogencarbonate solution (400 mL) under ice-cooling, and the mixture was subjected to extraction with ethyl acetate (200 mL). The organic layer was washed with water (400 mL), dried over anhydrous sodium sulfate, filtered, and concentrated to give the title compound (52 g).

$^1$H-NMR (400 MHz, CDCl$_3$) δ:7.86-7.86 (1H, m), 7.32 (5H, m), 6.75 (1H, dd, J=9.1, 2.4 Hz), 5.60 (1H, s), 5.11-5.09 (2H, m), 4.74-4.72 (1H, m), 3.73-3.72 (1H, m), 3.46-3.44 (1H, m), 3.16-3.15 (1H, m), 1.52 (3H, d, J=6.1 Hz).

Reference Examples 57 to 59

According to the methods described in Reference Example 7 to Reference Example 10, Reference Example 37 and Reference Example 47, the compounds of Reference Examples 57 to 59 were obtained from the corresponding compounds, respectively.

TABLE 15

| Ref. No. | Chemical Structure | Instrumental analysis data |
|---|---|---|
| 57 | (Me, abs.) structure with benzyl carbamate, methylpyrano-pyridine, F | LC-MS: R.T. = 1.042 min ObsMS = 331.2 [M + 1] |
| 58 | (Me, abs.) structure with benzyl carbamate, methylpyrano-pyridine, F | LC-MS: R.T. = 0.998 min ObsMS = 331.2 [M + 1] |
| 59 | (Me, Me, rac.) structure with benzyl carbamate, dimethylpyrano-pyridine | LC-MS: R.T. = 0.813 min ObsMS = 327.2 [M + 1] |

Reference Example 60 rac-tert-butyl {[6-(trifluoromethyl)-3,4-dihydro-2H-pyrano[3,2-b]pyridin-4-yl]methyl}carbamate

[Chemical Formula 94]

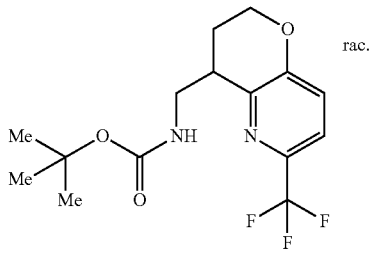

By the same methods as in Reference Example 1 to Reference Example 4 and Reference Example 6, the title compound was obtained from propane-1,3-diol and 2-bromo-6-(trifluoromethyl)pyridin-3-ol.

LC-MS: R.T.=1.133 min ObsMS=333.2 [M+1]

Reference Example 61 rac-tert-butyl [(1,2,3,4-tetrahydro-1,5-naphthyridin-4-yl)methyl]carbamate

[Chemical Formula 95]

To a mixture of the compound (261 mg, 1.01 mmol) of Reference Example 62 and tetrahydrofuran (5.0 mL) was added 0.90 mol/L tetrahydrofuran-borane tetrahydrofuran solution (2.24 mL, 2.01 mmol). After stirring at 60° C. for 2 hr, to the reaction mixture was added methanol (2.5 mL), and the mixture was stirred for 15 min. The reaction mixture was concentrated, the concentrated residue was dissolved in 2.0 mol/L hydrochloric acid (2.52 mL, 5.03 mmol), and the solution was stirred at 60° C. for 2 hr. The reaction mixture was concentrated, the concentrated residue was dissolved in chloroform (5.0 mL), and triethylamine (0.701 mL, 5.03 mmol) and di-tert-butyl dicarbonate (330 mg, 1.51 mmol) were added thereto. After stirring at room temperature for 1 day, to the reaction mixture was added water (5.0 mL), the mixture was subjected to extraction with chloroform (3.0 mL×twice), and the organic layer was dried over anhydrous magnesium sulfate, filtered, and concentrated. The concentrated residue was separated and purified by silica gel column chromatography (hexane/ethyl acetate) to give the title compound (100 mg).

$^1$H-NMR (400 MHz, CDCl$_3$)

δ: 7.87 (1H, dd, J=4.6, 1.5 Hz), 6.92 (1H, dd, J=7.9, 4.6 Hz), 6.74 (1H, dd, J=7.9, 1.5 Hz), 5.75 (1H, brs), 3.84 (1H, brs), 3.72-3.62 (1H, m), 3.40-3.27 (3H, m), 3.02-2.95 (1H, m), 2.08-1.99 (1H, m), 1.92-1.83 (1H, m), 1.44 (9H, s).

Reference Example 62 rac-tert-butyl 4-cyano-3,4-dihydro-1,5-naphthyridine-1(2H)-carboxylate

[Chemical Formula 96]

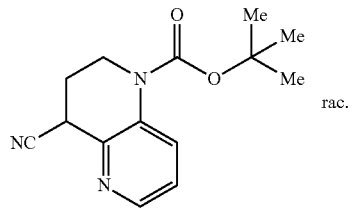

To a mixture of the compound (660 mg, 2.11 mmol) of Reference Example 63, trimethylsilylcyanide (0.523 mL, 4.21 mmol) and acetonitrile (14 mL) was added 1.0 mol/L tetrabutylammonium fluoride (4.21 mL, 4.21 mmol), and the mixture was stirred at 70° C. for 3 hr. The reaction mixture was concentrated, and the concentrated residue was separated and purified by silica gel column chromatography (hexane/ethyl acetate) to give the title compound (261 mg) as a white solid.

$^1$H-NMR (400 MHz, CDCl$_3$)

δ:8.31 (1H, dd, J=4.6, 1.5 Hz), 8.22 (1H, dd, J=8.5, 1.5 Hz), 7.23 (1H, dd, J=8.5, 4.6 Hz), 4.16 (1H, t, J=6.4 Hz), 3.92-3.87 (2H, m), 2.38-2.33 (2H, m), 1.54 (9H, s).

Reference Example 63 rac-tert-butyl 4-bromo-3,4-dihydro-1,5-naphthyridine-1(2H)-carboxylate

[Chemical Formula 97]

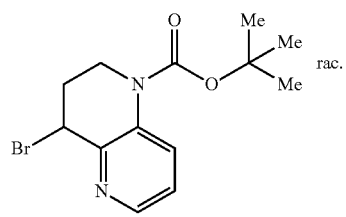

To a mixture of 1,1-dimethylethyl 3,4-dihydro-1,5-naphthyridine-1(2H)-carboxylate (560 mg, 2.39 mmol), N-bromosuccinimide (510 mg, 2.87 mmol) and carbon tetrachloride (12 mL) was added azobisisobutyronitrile (7.85 mg, 0.0480 mmol), and the mixture was heated under reflux for 5 hr. The reaction mixture was cooled to room temperature, the precipitated solid was filtered off, and the filtrate was concentrated. The concentrated residue was separated and purified by silica gel column chromatography (hexane/ethyl acetate) to give the title compound (510 mg).

$^1$H-NMR (400 MHz, CDCl$_3$)

δ:8.33 (1H, dd, J=8.8, 1.5 Hz), 8.27 (1H, dd, J=4.6, 1.5 Hz), 7.20 (1H, dd, J=8.8, 4.6 Hz), 5.53 (1H, t, J=3.0 Hz), 4.32-4.27 (1H, m), 3.88-3.81 (1H, m), 2.50 (1H, ddd, J=15.1, 3.3, 3.3 Hz), 2.44-2.35 (1H, m), 1.55 (9H, s).

Reference Examples 64 to 65

According to the methods described in Reference Example 37 to Reference Example 39, the compounds of Reference Examples 64 to 65 were obtained from the corresponding compounds, respectively.

TABLE 16

| Ref. No. | Chemical Structure | Instrumental analysis data |
|---|---|---|
| 64 | 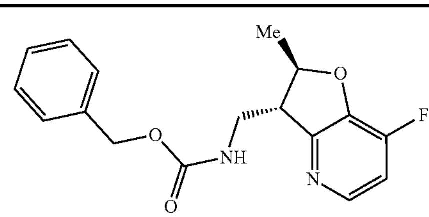 | $^1$H-NMR (400 MHz, CDCl$_3$) δ: 7.97 (1H, dd, J = 6.1, 6.1 Hz), 7.40-7.29 (5H, m), 6.89 (1H, dd, J = 10.4, 6.1 Hz), 5.69 (1H, brs), 5.11 (2H, s), 4.81-4.71 (1H, m), 3.77-.3.72 (1H, m), 3.52-3.43 (1H, m), 3.30-3.24 (1H, m), 1.58 (3H, d, J = 6.1 Hz). |
| 65 | 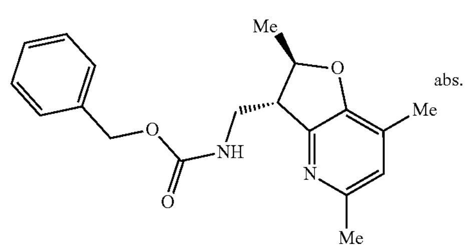 [SMILES: Cc1cc(C)c2c(n1)[C@H](CNC(=O)OCc1ccccc1)[C@@H](C)O2] | $^1$H-NMR (400 MHz, CDCl$_3$) δ: 7.38-7.35 (5H, m), 6.73 (1H, s), 5.79 (1H, brs), 5.11 (2H, s), 4.61-4.59 (1H, m), 3.79-3.73 (1H, m), 3.47-3.40 (1H, m), 3.16-3.14 (1H, m), 2.42 (3H, s), 2.16 (3H, s), 1.51 (3H, d, J = 6.7 Hz). |

Reference Example 66

2-iodo-4,6-dimethylpyridin-3-ol

[Chemical Formula 98]

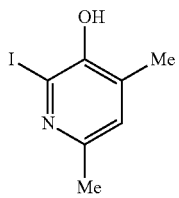

To a mixture of 4,6-dimethyl-3-hydroxypyridine (99.8 mg, 0.810 mmol), water (12 mL) and tetrahydrofuran (2.0 mL) was added iodine (247 mg, 0.972 mmol) at 0° C. After stirring at room temperature for 25 hr, to the reaction mixture was added 1 mol/L hydrochloric acid (4 mL), the mixture was subjected to extraction with ethyl acetate (10 mL×three times), and the organic layer was dried over anhydrous magnesium sulfate, filtered, and concentrated. The organic layer was washed with 0.1 mol/L aqueous sodium thiosulfate solution (10 mL×three times), dried over anhydrous sodium sulfate, filtered, and concentrated. The concentrated residue was separated and purified by silica gel column chromatography (hexane/ethyl acetate) to give the title compound (140 mg).
$^1$H-NMR (400 MHz, CDCl$_3$) δ:6.82 (1H, s), 2.42 (3H, s), 2.27 (3H, s).

Reference Example 67 benzyl {2-[(2R,3S)-2-methyl-2,3-dihydrofuro[3,2-b]pyridin-3-yl]propan-2-yl}carbamate

[Chemical Formula 99]

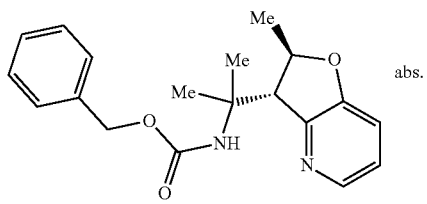

To a mixture of the compound (78.0 mg, 0.313 mmol) of Reference Example 68, methanol (0.70 mL) and water (0.35 mL) was added sodium hydroxide (37.5 mg, 0.939 mmol) at room temperature. After stirring at 60° C. for 2 hr, 3.0 mol/L hydrochloric acid was added to the aqueous layer until the layer reached pH5. The reaction solution was concentrated, and the concentrated residue was dissolved in methanol. The insoluble material was filtered off, and the filtrate was concentrated.

To a toluene solution (0.45 mL) of the obtained concentrated residue (69.0 mg) were added triethylamine (0.130 mL, 0.936 mmol) and diphenylphosphoryl azide (0.0800 mL, 0.374 mmol) at room temperature. After stirring at room temperature for 30 min, the reaction solution was heated to 90° C. After stirring at 90° C. for 1 hr, to the reaction solution was added benzyl alcohol (0.0482 mL, 0.468 mmol). After stirring at 90° C. for 3 hr, to the reaction mixture was added saturated aqueous sodium hydrogencarbonate solution (1.0 mL) under ice-cooling, the mixture was subjected to extraction with ethyl acetate (1.0 mL×twice), and the organic layer was dried over anhydrous magnesium sulfate, filtered, and concentrated. The concentrated residue was separated and purified by silica gel column chromatography (hexane/ethyl acetate) to give the title compound (53.0 mg).
$^1$H-NMR (400 MHz, CDCl$_3$) δ:8.00 (1H, dd, J=4.6, 1.5 Hz), 7.40-7.29 (5H, m), 7.06 (1H, dd, J=8.2, 4.6 Hz), 7.01 (1H, dd, J=8.2, 1.5 Hz), 6.18 (1H, brs), 5.11 (1H, d, J=12.8 Hz), 5.07 (1H, d, J=12.8 Hz), 4.80 (1H, dq, J=6.7, 4.3 Hz), 3.42 (1H, d, J=4.3 Hz), 1.39 (3H, d, J=6.7 Hz), 1.33 (3H, s), 1.31 (3H, s).

Reference Example 68 ethyl 2-methyl-2-[(2R,3S)-2-methyl-2,3-dihydrofuro[3,2-b]pyridin-3-yl]propanoate

[Chemical Formula 100]

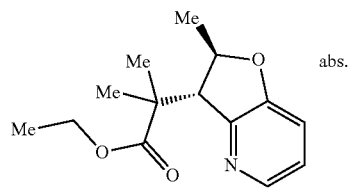

To a tetrahydrofuran solution (1.7 mL) of the compound (150 mg, 0.678 mmol) of Reference Example 69 was added dropwise 1.0 mol/L lithium bis(trimethylsilyl)amide toluene solution (1.63 mL, 1.63 mmol) at −78° C. After stirring at −78° C. for 30 min, iodomethane (1.63 mL, 1.63 mmol) was added thereto. After stirring for additional 1 hr, the reaction mixture was warmed to room temperature over 1 hr. To the reaction mixture was added saturated aqueous ammonium chloride solution (3.4 mL) under ice-cooling, the mixture was subjected to extraction with ethyl acetate (1.7 mL×twice), and the organic layer was dried over anhydrous magnesium sulfate, filtered, and concentrated. The concentrated residue was separated and purified by silica gel column chromatography (hexane/ethyl acetate) to give the title compound (78.0 mg).
$^1$H-NMR (400 MHz, CDCl$_3$)
δ:8.06 (1H, dd, J=4.6, 1.5 Hz), 7.04 (1H, dd, J=7.9, 4.6 Hz), 6.99 (1H, dd, J=7.9, 1.5 Hz), 4.67 (1H, dq, J=6.0, 3.7 Hz), 4.69-4.63 (2H, m), 3.34 (1H, d, J=3.7 Hz), 1.59 (2H, d, J=7.3 Hz), 1.41 (3H, d, J=6.0 Hz), 1.40 (3H, s), 1.26 (3H, t, J=7.3 Hz), 1.05 (3H, s).

Reference Example 69 ethyl [(2R,3S)-2-methyl-2,3-dihydrofuro[3,2-b]pyridin-3-yl]acetate

[Chemical Formula 101]

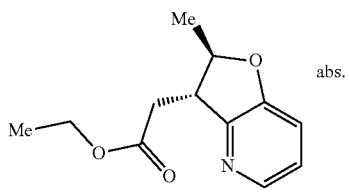

To a toluene solution (73 mL) of the compound (6.58 g, 21.9 mmol) of Reference Example 39 were added tributyltin hydride (9.77 mL, 37.3 mmol) and azobisisobutyronitrile (0.360 g, 2.19 mmol) at room temperature. After stirring at 90° C. for 1 hr, the reaction mixture was concentrated. The residue was separated and purified by silica gel column chromatography (hexane/ethyl acetate) to give the title compound (3.87 g) as a diastereomeric mixture (5:1).
Major Diastereomer
$^1$H-NMR (400 MHz, CDCl$_3$) δ:8.05-8.01 (1H, m), 7.13-7.01 (2H, m), 4.76-4.67 (1H, m), 4.21-4.09 (2H, m), 3.58-3.48 (1H, m), 3.07 (1H, dd, J=16.5, 3.7 Hz), 2.75-2.62 (1H, m), 1.53 (3H, d, J=6.1 Hz), 1.24 (3H, t, J=6.7 Hz).

Reference Example 70-1, Reference Example 70-2

Reference Example 70-1 benzyl {(1S)-1-[(2R,3S)-2-methyl-2,3-dihydrofuro[3,2-b]pyridin-3-yl]ethyl}carbamate

Reference Example 70-2 benzyl {(1R)-1-[(2R,3S)-2-methyl-2,3-dihydrofuro[3,2-b]pyridin-3-yl]ethyl}carbamate

[Chemical Formula 102]

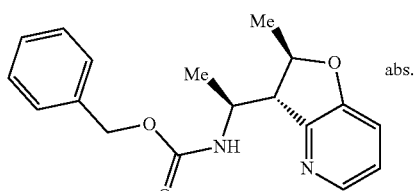

Ref. Example 70-1

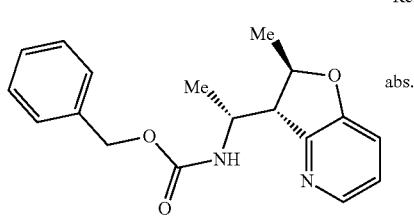

Ref. Example 70-2

By the same method as in Reference Example 67, the title compounds of Reference Example 70-1 and Reference Example 70-2 were obtained from the compound of Reference Example 71, respectively.

Reference Example 70-1

$^1$H-NMR (400 MHz, CDCl$_3$) δ:8.03 (1H, d, J=3.7 Hz), 7.40-7.30 (5H, m), 7.10-7.00 (2H, m), 6.29 (1H, d, J=8.5 Hz), 5.14 (1H, d, J=12.2 Hz), 5.09 (1H, d, J=12.2 Hz), 4.67 (1H, dq, J=6.7, 4.3 Hz), 4.12-4.07 (1H, m), 3.32-3.29 (1H, m), 1.49 (4H, d, J=6.7 Hz), 1.03 (3H, d, J=6.7 Hz).

Reference Example 70-2

$^1$H-NMR (400 MHz, CDCl$_3$) δ:8.01 (1H, d, J=4.9 Hz), 7.38-7.28 (5H, m), 7.08-6.99 (2H, m), 5.08 (1H, d, J=12.2 Hz), 5.03 (1H, d, J=12.2 Hz), 4.79-4.73 (1H, dq, J=6.7, 6.7 Hz), 4.13-4.03 (1H, m), 3.19 (1H, dd, J=5.5, 5.5 Hz), 1.47 (3H, d, J=6.7 Hz), 1.43 (3H, d, J=6.1 Hz).

Reference Example 71-1, Reference Example 71-2

Reference Example 71-1 ethyl (2S)-2-[(2R,3S)-2-methyl-2,3-dihydrofuro[3,2-b]pyridin-3-yl]propanoate

Reference Example 71-2 ethyl (2R)-2-[(2R,3S)-2-methyl-2,3-dihydrofuro[3,2-b]pyridin-3-yl]propanoate

[Chemical Formula 103]

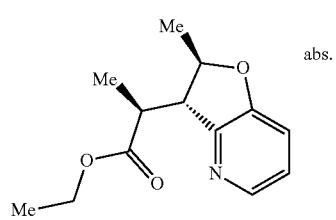

Ref. Example 71-1

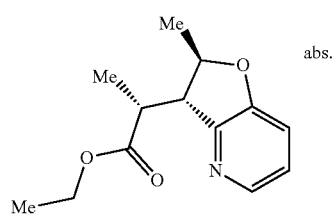

Ref. Example 71-2

To a tetrahydrofuran solution (9.0 mL) of the compound (800 mg, 3.62 mmol) of Reference Example 69 was added dropwise 1.0 mol/L lithium bis(trimethylsilyl)amide tetrahydrofuran solution (3.80 mL, 3.80 mmol) at −78° C. After stirring at −78° C. for 30 min, iodomethane (0.270 mL, 4.34 mmol) was added thereto. After stirring for additional 1 hr, the reaction mixture was warmed to room temperature over 1 hr. To the reaction mixture was added saturated aqueous ammonium chloride solution (18 mL) under ice-cooling, the mixture was subjected to extraction with ethyl acetate (18 mL×twice), and the organic layer was dried over anhydrous magnesium sulfate, filtered, and concentrated. The concentrated residue was separated and purified by silica gel column chromatography (hexane/ethyl acetate) to give the title compounds (826 mg) as a diastereomeric mixture (1.4:1) of Reference Example 71-1 and Reference Example 71-2.
Major Diastereomer $^1$H-NMR (400 MHz, CDCl$_3$) δ:8.08-8.05 (1H, m), 7.07-7.00 (2H, m), 4.85 (1H, dq, J=7.3, 5.5 Hz), 4.20-4.17 (2H, m), 3.53-3.52 (1H, m), 3.16-3.14 (1H, m), 1.37 (3H, d, J=7.3 Hz), 1.27 (3H, t, J=7.0 Hz), 1.01 (3H, d, J=7.3 Hz).

Reference Examples 72 to 73

According to the methods described in Reference Example 1 to Reference Example 4 and Reference Example 6, the compounds of Reference Examples 72 to 73 were obtained from the corresponding compounds, respectively.

TABLE 17

| Ref. No. | Chemical Structure | Instrumental analysis data |
|---|---|---|
| 72 | 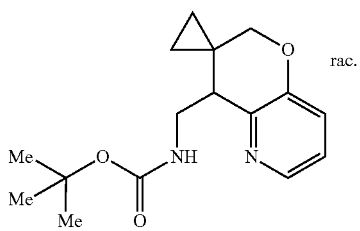 [SMILES: CC(C)(C)OC(=O)NCC1c2ncccc2OCC12CC2] | $^1$H-NMR (400 MHz, CDCl$_3$) δ: 8.14 (1H, dd, J = 4.3, 1.2 Hz), 7.18 (1H, brd, J = 7.3 Hz), 7.12 (1H, dd, J = 8.2, 4.3 Hz), 5.68 (1H, brs), 4.39 (1H, dd, J = 11.3, 1.5 Hz), 3.73-3.66 (1H, m), 3.40-3.29 (2H, m), 2.35-2.28 (1H, m), 1.44 (9H, s), 0.91-0.85 (1H, m), 0.69-0.60 (2H, m), 0.57-0.52 (1H, m). |
| 73 | 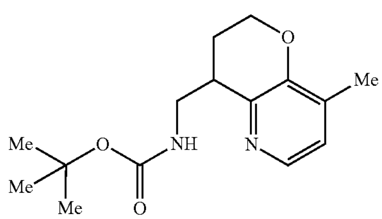 | LC-MS: R.T. = 1.675 min ObsMS = 278 [M] |

Reference Example 74 rac-benzyl {[(2R,3S)-2-methyl(2-$^2$H)-2,3-dihydro-furo[3,2-b]pyridin-3-yl]methyl}carbamate

[Chemical Formula 104]

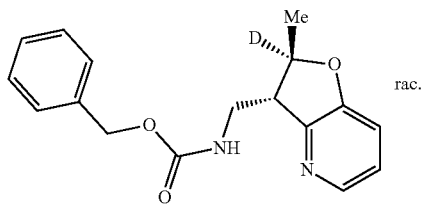

By the same methods as in Reference Example 8 to Reference Example 10, Reference Example 37 and Reference Example 38, the title compound was obtained from the compound of Reference Example 75.

$^1$H-NMR (400 MHz, CDCl$_3$) δ:8.01-7.97 (1H, m), 7.37-7.27 (5H, m), 7.08-7.03 (2H, m), 5.79 (1H, s), 5.10 (2H, s), 3.81-3.77 (1H, m), 3.50-3.40 (1H, m), 3.23-3.19 (1H, m), 1.53 (3H, s).

Reference Example 75 rac-1-{[tert-butyl(dimethyl)silyl]oxy} (2-$^2$H)propan-2-ol

[Chemical Formula 105]

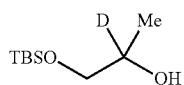

To a chloroform solution (45 mL) of propane-2-d-1,2-diol (1.04 g, 13.5 mmol) were added imidazole (0.919 g, 13.5 mmol) and tert-butyldimethylsilyl chloride (1.83 g, 12.2 mmol) at room temperature. After stirring at room temperature for 2 hr, to the reaction mixture was added water (200 mL), the mixture was subjected to extraction with chloroform (200 mL×twice), and the organic layer was dried over anhydrous sodium sulfate, filtered, and concentrated. The residue was separated and purified by silica gel column chromatography (hexane/ethyl acetate) to give the title compound (1.51 g).

¹H-NMR (400 MHz, CDCl₃) δ:3.64-3.58 (1H, m), 3.40-3.33 (1H, m), 1.15-1.10 (3H, m), 0.96-0.88 (9H, m), 0.13-0.05 (6H, m).

Reference Example 76-1, Reference Example 76-2

Reference Example 76-1 rac-benzyl {[(2R,4R)-2-ethyl-3,4-dihydro-2H-pyrano[3,2-b]pyridin-4-yl]methyl}carbamate Reference Example 76-2 rac-benzyl {[(2R,4S)-2-ethyl-3,4-dihydro-2H-pyrano[3,2-b]pyridin-4-yl]methyl}carbamate

[Chemical Formula 106]

Ref. Example 76-1

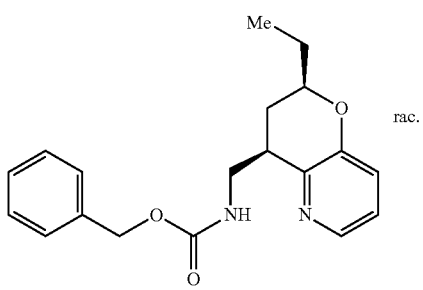

Ref. Example 76-2

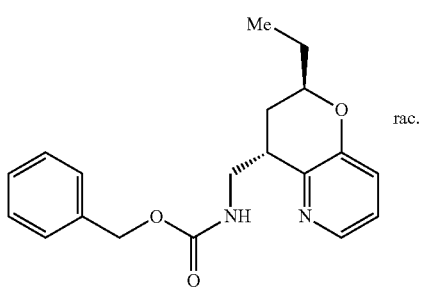

By the same methods as in Reference Example 8, Reference Example 37 and Reference Example 38, the title compounds of Reference Example 76-1 and Reference Example 76-2 were obtained from the compound of Reference Example 77, respectively.

Reference Example 76-1

¹H-NMR (400 MHz, CDCl₃) δ:8.13-8.10 (1H, m), 7.35-7.29 (5H, m), 7.13 (2H, d, J=8.5 Hz), 6.33 (1H, s), 5.08 (2H, s), 3.99-3.95 (1H, m), 3.89-3.86 (1H, m), 3.46-3.44 (1H, m), 3.18-3.15 (1H, m), 2.14-2.12 (1H, m), 1.80-1.60 (3H, m), 1.04-1.02 (3H, m).

Reference Example 76-2

¹H-NMR (400 MHz, CDCl₃) δ:8.10 (1H, s), 7.35-7.34 (5H, m), 7.10-7.05 (2H, m), 5.93 (1H, s), 5.09 (2H, s), 4.04-4.01 (1H, m), 3.68-3.66 (1H, m), 3.42-3.39 (1H, m), 3.01-2.99 (1H, m), 1.91-1.66 (4H, m), 1.03-1.01 (3H, m).

Reference Example 77 rac-3-[(2-bromopyridin-3-yl)oxy]pentan-1-ol

[Chemical Formula 107]

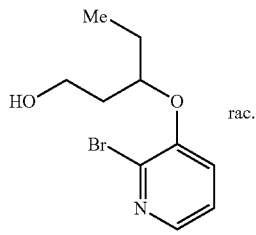

To a chloroform solution (13 mL) of the compound (1.73 g, 6.31 mmol) of Reference Example 78 was added 1 mol/L boron tribromide dichloromethane solution (12.6 mL, 12.6 mmol) under ice-cooling. After stirring at room temperature for 2 hr, to the reaction mixture was added saturated aqueous sodium hydrogencarbonate solution (100 mL), the mixture was subjected to extraction with chloroform (100 mL×twice), and the organic layer was dried over anhydrous sodium sulfate, filtered, and concentrated. The residue was separated and purified by silica gel column chromatography (hexane/ethyl acetate) to give the title compound (0.541 g).

¹H-NMR (400 MHz, CDCl₃)

δ:7.97 (1H, dd, J=4.6, 1.5 Hz), 7.25 (1H, dd, J=8.2, 1.5 Hz), 7.20 (1H, dd, J=7.9, 4.3 Hz), 4.55-4.48 (1H, m), 3.90-3.79 (2H, m), 2.08-1.92 (2H, m), 1.82-1.72 (2H, m), 1.00 (3H, t, J=7.3 Hz).

Reference Example 78 rac-2-bromo-3-[(1-methoxypentan-3-yl)oxy]pyridine

[Chemical Formula 108]

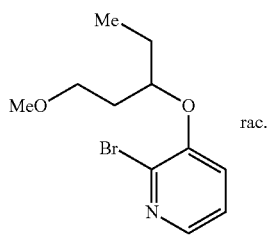

By the same method as in Reference Example 10, the title compound was obtained from 1-methoxypentan-3-ol.

¹H-NMR (400 MHz, CDCl₃) δ:7.97-7.93 (1H, m), 7.27-7.22 (1H, m), 7.21-7.16 (1H, m), 4.50-4.42 (1H, m), 3.50 (2H, t, J=5.5 Hz), 3.30 (3H, s), 2.03-1.88 (2H, m), 1.80-1.70 (2H, m), 1.00 (3H, t, J=7.0 Hz).

Reference Example 79 rac-benzyl [(3'H-spiro[cyclopropane-1,2'-furo[3,2-b]pyridine]-3'-yl)methyl]carbamate

[Chemical Formula 109]

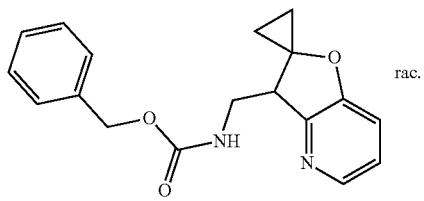

By the same methods as in Reference Example 30, Reference Example 31, Reference Example 37 and Reference Example 38, the title compound was obtained from the compound of Reference Example 80.

$^1$H-NMR (400 MHz, CDCl$_3$) δ:8.08-8.07 (1H, m), 7.35-7.33 (5H, m), 7.09-7.07 (1H, m), 7.02-7.00 (1H, m), 5.97 (1H, s), 5.14-5.10 (2H, m), 3.76-3.69 (1H, m), 3.51-3.49 (1H, m), 3.33-3.27 (1H, m), 1.24-1.19 (1H, m), 1.12-1.02 (2H, m), 0.76-0.70 (1H, m).

Reference Example 80 methyl 1-[(2-bromopyridin-3-yl)oxy]cyclopropane-1-carboxylate

[Chemical Formula 110]

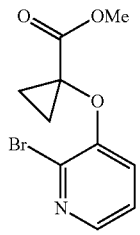

To a tetrahydrofuran solution (75 mL) of the compound (2.65 g, 7.51 mmol) of Reference Example 81 was added potassium tert-butoxide (0.842 g, 7.51 mmol) at 0° C. After stirring at room temperature for 90 min, additional potassium tert-butoxide (0.168 g, 1.50 mmol) was added thereto. After stirring at room temperature for 20 min, water was added thereto, the mixture was subjected to extraction with ethyl acetate, and the organic layer was dried over anhydrous sodium sulfate, filtered, and concentrated. The concentrated residue was separated and purified by silica gel column chromatography (hexane/ethyl acetate) to give the title compound (1.69 g).

$^1$H-NMR (400 MHz, CDCl$_3$) δ:8.05-8.04 (1H, m), 7.24-7.18 (2H, m), 3.76 (3H, s), 1.71-1.69 (2H, m), 1.42-1.40 (2H, m).

Reference Example 81 rac-methyl 4-bromo-2-[(2-bromopyridin-3-yl)oxy]butanoate

[Chemical Formula 111]

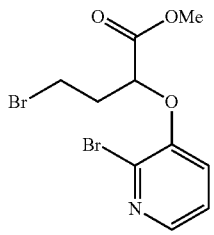

To an N,N-dimethylformamide solution (48.1 mL) of 2-bromo-3-hydroxypyridine (1.67 g, 9.62 mmol) were added potassium carbonate (2.66 g, 19.24 mmol) and methyl 2,4-dibromobutyrate (3.0 g, 11.54 mmol) at room temperature. After stirring at room temperature for 3 hr, to the reaction mixture was added water, and the mixture was subjected to extraction with ethyl acetate. The organic layer was washed three times with water, and the organic layer was dried over anhydrous sodium sulfate, filtered, and concentrated. The concentrated residue was separated and purified by silica gel column chromatography (hexane/ethyl acetate) to give the title compound (2.75 g).

$^1$H-NMR (400 MHz, CDCl$_3$) δ:8.04-8.03 (1H, m), 7.20-7.15 (1H, m), 7.08-7.06 (1H, m), 4.91-4.88 (1H, m), 3.77 (3H, s), 3.75-3.61 (2H, m), 2.63-2.58 (1H, m), 2.51-2.46 (1H, m).

Reference Example 82 tert-butyl {[(2R,3S)-2-methyl-2,3-dihydrofuro[3,2-b]pyridin-3-yl]methyl}prop-2-en-1-ylcarbamate

[Chemical Formula 112]

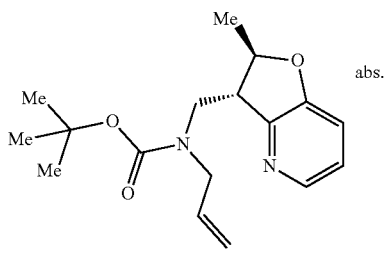

To a tetrahydrofuran solution (48.1 mL) of the compound (50 mg, 0.189 mmol) of Reference Example 83 was added 55% sodium hydride (24.76 mg, 0.567 mmol) at 0° C. After stirring at room temperature for 90 min, allyl bromide (0.048 mL, 0.567 mmol) was added thereto. After stirring at room temperature for 90 min, water was added thereto, the mixture was subjected to extraction with ethyl acetate, and the organic layer was dried over anhydrous sodium sulfate, filtered, and concentrated. The concentrated residue was separated and purified by silica gel column chromatography (hexane/ethyl acetate) to give the title compound (34.8 mg).

¹H-NMR (400 MHz, CDCl₃) δ:8.00-7.94 (1H, m), 6.99-6.89 (2H, m), 5.78-5.60 (1H, m), 5.13-4.98 (2H, m), 4.90-4.70 (1H, m), 3.86-3.51 (4H, m), 3.29-3.15 (1H, m), 1.43-1.37 (12H, m).

Reference Example 83 tert-butyl {[(2R,3S)-2-methyl-2,3-dihydrofuro[3,2-b]pyridin-3-yl]methyl}carbamate

[Chemical Formula 113]

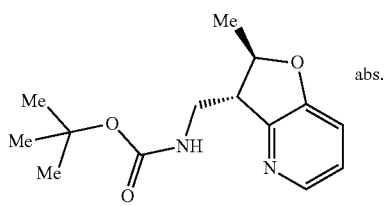

By the same method as in Example 5, the title compound was obtained from the compound of Example 27.

¹H-NMR (400 MHz, CDCl₃)

δ:8.02 (1H, dd, J=4.6, 1.5 Hz), 7.03 (1H, dd, J=8.2, 4.6 Hz), 6.98 (1H, dd, J=7.9, 1.2 Hz), 5.40 (1H, brs), 4.68-4.60 (1H, m), 3.73-3.62 (1H, m), 3.44-3.33 (1H, m), 3.19-3.13 (1H, m), 1.52 (3H, d, J=6.7 Hz), 1.43 (9H, s).

Reference Example 84 tert-butyl {[(2R,3S)-2-methyl-2,3-dihydrofuro[3,2-b]pyridin-3-yl]methyl}propylcarbamate

[Chemical Formula 114]

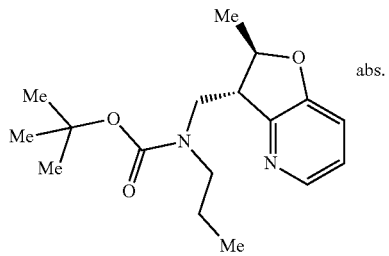

To a methanol solution (1.0 mL) of the compound (34.8 mg, 0.114 mmol) of Reference Example 82 was added 10% palladium/carbon (25 mg). After stirring under hydrogen atmosphere at room temperature for 2 hr, the mixture was filtered through Celite, and the filtrate was concentrated. The concentrated residue was separated and purified by silica gel column chromatography (hexane/ethyl acetate) to give the title compound (32.0 mg).

¹H-NMR (400 MHz, CDCl₃) δ:7.97 (1H, d, J=3.7 Hz), 6.98-6.91 (2H, m), 4.83 (1H, brs), 3.73-3.58 (2H, m), 3.23-3.12 (3H, m), 1.53-1.41 (2H, m), 1.40 (3H, d, J=6.1 Hz), 1.39 (9H, s), 0.78 (3H, t, J=7.3 Hz).

Reference Examples 85 to 87

According to the method described in Reference Example 82, the compounds of Reference Examples 85 to 87 were obtained from the corresponding compounds, respectively.

TABLE 18

| Ref. No. | Chemical Structure | Instrumental analysis data |
|---|---|---|
| 85 | ![structure] | ¹H-NMR (400 MHz, CDCl₃) δ: 8.05 (1H, d, J = 4.3 Hz), 7.05-6.99 (2H, m), 4.86 (1H, s), 3.85-3.65 (2H, m), 3.56-3.43 (5H, m), 3.34 (3H, s), 1.48 (3H, d, J = 4.3 Hz), 1.48 (9H, s). |
| 86 | ![structure] | ¹H-NMR (400 MHz, CDCl₃) δ: 7.98-7.97 (1H, m), 6.97-6.94 (2H, m), 4.84 (1H, brs), 3.71-3.59 (2H, m), 3.24-3.21 (3H, m), 1.41 (3H, d, J = 6.7 Hz), 1.40 (9H, s), 1.02 (3H, brs). |

TABLE 18-continued

| Ref. No. | Chemical Structure | Instrumental analysis data |
|---|---|---|
| 87 | (benzyl carbamate with methyl-d3, connected to 2-methyl-2,3-dihydrofuro[3,2-b]pyridine, abs.) | $^1$H-NMR (400 MHz, CDCl$_3$) δ: 7.87 (1H, dd, J = 2.4, 1.2 Hz), 7.39-7.26 (6H, m), 6.77-6.69 (1H, m), 5.14-5.07 (2H, m), 4.96-4.70 (1H, m), 3.87-3.57 (2H, m), 3.29-3.19 (1H, m), 1.45-1.29 (3H, m). |

Reference Example 88-1, Reference Example 88-2, Reference Example 88-3, Reference Example 88-4

Reference Example 88-1 rac-benzyl {[(2R,3R,4R)-2,3-dimethyl-3,4-dihydro-2H-pyrano[3,2-b]pyridin-4-yl]methyl}carbamate Reference Example 88-2 rac-benzyl {[(2R,3S,4R)-2,3-dimethyl-3,4-dihydro-2H-pyrano[3,2-b]pyridin-4-yl]methyl}carbamate Reference Example 88-3 rac-benzyl {[(2S,3R,4R)-2,3-dimethyl-3,4-dihydro-2H-pyrano[3,2-b]pyridin-4-yl]methyl}carbamate Reference Example 88-4 rac-benzyl {[(2S,3S,4R)-2,3-dimethyl-3,4-dihydro-2H-pyrano[3,2-b]pyridin-4-yl]methyl}carbamate

[Chemical Formula 115]

Ref. Example 88-1

Ref. Example 88-2

Ref. Example 88-3

Ref. Example 88-4

By the same methods as in Reference Example 8 to Reference Example 10, Reference Example 37, Reference Example 38 and Reference Example 75, the title compounds of Reference Example 88-1, Reference Example 88-2, Reference Example 88-3 and Reference Example 88-4 were obtained from 2-methylbutane-1,3-diol, respectively.

Reference Example 88-1

$^1$H-NMR (400 MHz, CDCl$_3$) δ:8.05-8.05 (1H, m), 7.36-7.30 (5H, m), 7.05-6.98 (2H, m), 6.72 (1H, brs), 5.15-5.07 (2H, m), 4.31-4.30 (1H, m), 3.79-3.73 (1H, m), 3.37-3.34 (1H, m), 3.24-3.19 (1H, m), 2.11-2.09 (1H, m), 1.35 (3H, d, J=6.7 Hz), 0.79 (3H, d, J=6.7 Hz).

Reference Example 88-2

$^1$H-NMR (400 MHz, CDCl$_3$) δ:8.09-8.08 (1H, m), 7.34-7.26 (5H, m), 7.06-7.03 (2H, m), 6.07 (1H, brs), 5.09-5.05 (2H, m), 4.03-3.99 (1H, m), 3.80-3.75 (1H, m), 3.43-3.37 (1H, m), 2.66-2.61 (1H, m), 1.65-1.60 (1H, m), 1.40 (3H, d, J=6.1 Hz), 1.16 (3H, d, J=6.1 Hz).

Reference Example 88-3

$^1$H-NMR (400 MHz, CDCl$_3$) δ:8.02-8.01 (1H, m), 7.33-7.22 (5H, m), 7.02-7.00 (2H, m), 6.47 (1H, d, J=6.7 Hz), 5.06-5.03 (2H, m), 4.08-4.04 (1H, m), 3.75-3.68 (1H, m), 3.22-3.16 (1H, m), 2.99-2.94 (1H, m), 2.02-1.98 (1H, m), 1.27 (3H, d, J=6.7 Hz), 0.97 (3H, d, J=7.3 Hz).

Reference Example 88-4

$^1$H-NMR (400 MHz, CDCl$_3$) δ:8.13-8.11 (1H, m), 7.37-7.27 (5H, m), 7.10-7.06 (2H, m), 5.88 (1H, s), 5.09 (2H, s), 4.30-4.28 (1H, m), 3.80-3.73 (1H, m), 3.43-3.37 (1H, m), 2.70-2.68 (1H, m), 2.00-1.97 (1H, m), 1.31 (3H, d, J=6.4 Hz), 0.98 (3H, d, J=6.9 Hz).

Reference Example 89 rac-tert-butyl [(6'-chloro-3'H-spiro[cyclopropane-1,2'-furo[3,2-b]pyridine]-3'-yl)methyl]carbamate

[Chemical Formula 116]

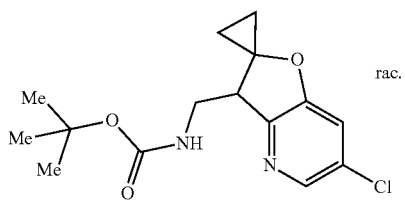

By the same methods as in Reference Example 6, Reference Example 7, Reference Example 30 and Reference Example 31, the title compound was obtained from the compound of Reference Example 90.

$^1$H-NMR (400 MHz, CDCl$_3$)

δ:7.99 (1H, d, J=1.8 Hz), 6.95 (1H, d, J=1.8 Hz), 5.38 (1H, s), 3.58-3.52 (1H, m), 3.36-3.34 (1H, m), 3.16-3.12 (1H, m), 1.37 (9H, s), 1.22-1.11 (1H, m), 1.02-0.99 (2H, m), 0.69-0.63 (1H, m).

Reference Example 90 methyl 1-[(2-bromo-5-chloropyridin-3-yl)oxy]cyclopropane-1-carboxylate

[Chemical Formula 117]

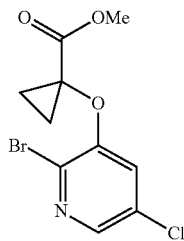

By the same methods as in Reference Example 80 and Reference Example 81, the title compound was obtained from 2-bromo-5-chloro-3-hydroxypyridine.

$^1$H-NMR (400 MHz, CDCl$_3$)

δ:8.00 (1H, d, J=1.8 Hz), 7.16 (1H, d, J=1.8 Hz), 3.74 (3H, s), 1.70-1.68 (2H, m), 1.40-1.39 (2H, m).

Reference Example 91 rac-2-[(2-methoxy-5,6,7,8-tetrahydroquinolin-8-yl)methyl]-1H-isoindole-1,3(2H)-dione

[Chemical Formula 118]

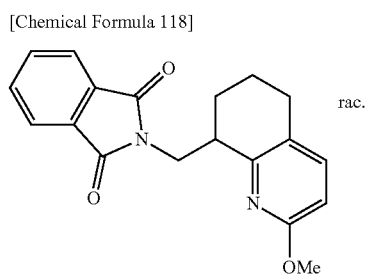

To a mixture of the compound (110 mg, 0.337 mmol) of Reference Example 92, dimethyl sulfoxide (1.68 mL) and methanol (1.68 mL) was added sodium methoxide (364 mg, 6.73 mmol) at room temperature. After stirring at 100° C., to the reaction mixture was added water, the mixture was subjected to extraction with ethyl acetate, and the organic layer was dried over sodium sulfate, filtered, and concentrated. The concentrated residue was separated and purified by silica gel column chromatography (hexane/ethyl acetate) to give the title compound (9 mg).

$^1$H-NMR (400 MHz, CDCl$_3$) δ:7.84-7.83 (2H, m), 7.70-7.69 (2H, m), 7.25-7.24 (1H, m), 6.49 (1H, d, J=8.5 Hz), 4.41-4.37 (1H, m), 3.79-3.76 (1H, m), 3.66 (3H, s), 3.33 (1H, s), 2.68-2.66 (2H, m), 1.81-1.72 (4H, m).

Reference Example 92 rac-2-[(2-chloro-5,6,7,8-tetrahydroquinolin-8-yl)methyl]-1H-isoindole-1,3(2H)-dione

[Chemical Formula 119]

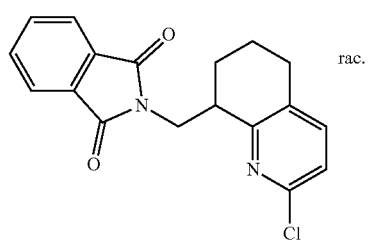

To the compound (440 mg, 1.427 mmol) of Reference Example 93 was added phosphoryl chloride (2.0 mL, 21.46 mmol) at room temperature. After stirring at 90° C. for 4 hr, to the reaction mixture was added ice water. Then, 4 mol/L sodium hydroxide was added thereto, the mixture was subjected to extraction with ethyl acetate, and the organic layer was dried over sodium sulfate, filtered, and concentrated. The concentrated residue was separated and purified by silica gel column chromatography (hexane/ethyl acetate) to give the title compound (110 mg).

$^1$H-NMR (400 MHz, CDCl$_3$) δ:7.85-7.81 (2H, m), 7.72-7.68 (2H, m), 7.30 (1H, d, J=8.5 Hz), 7.01 (1H, d, J=7.9 Hz), 4.26-4.23 (1H, m), 3.82-3.78 (1H, m), 3.44-3.42 (1H, m), 2.75-2.70 (2H, m), 1.93-1.88 (2H, m), 1.75-1.66 (2H, m).

Reference Example 93 rac-2-[(1-oxo-5,6,7,8-tetrahydro-1λ⁵-quinolin-8-yl)methyl]-1H-isoindole-1,3(2H)-dione

[Chemical Formula 120]

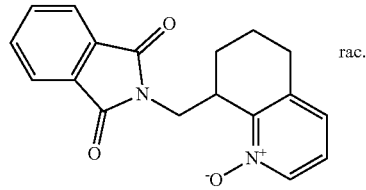

To a chloroform solution (10.4 mL) of the compound (608 mg, 2.080 mmol) of Reference Example 94 was added 70% 3-chloroperbenzoic acid (564 mg, 2.29 mmol) at 0° C. After stirring at 0° C. for 4 hr, to the reaction mixture was added saturated aqueous sodium bicarbonate, the mixture was subjected to extraction with chloroform, and the organic layer was dried over sodium sulfate, filtered, and concentrated to give the title compound (646 mg).

¹H-NMR (400 MHz, CDCl₃) δ:8.30-8.29 (1H, m), 7.86-7.83 (2H, m), 7.73-7.70 (2H, m), 7.18 (2H, d, J=4.3 Hz), 4.37-4.34 (1H, m), 4.15-4.14 (1H, m), 4.00-3.97 (1H, m), 2.93-2.88 (1H, m), 2.83-2.74 (1H, m), 2.03-1.93 (2H, m), 1.83-1.74 (2H, m).

Reference Example 94 rac-2-[(5,6,7,8-tetrahydroquinolin-8-yl)methyl]-1H-isoindole-1,3(2H)-dione

[Chemical Formula 121]

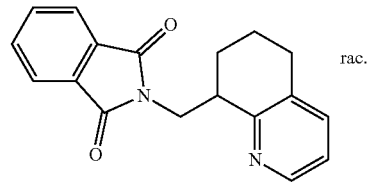

To a chloroform solution (25 mL) of 5,6,7,8-tetrahydroquinolin-8-ylmethanamine (400 mg, 2.47 mmol) was added phthalic anhydride (548 mg, 3.70 mmol). After stirring at 70° C. for 5 hr, the reaction mixture was concentrated. The concentrated residue was separated and purified by silica gel chromatography (hexane/ethyl acetate) to give the title compound (608 mg).

¹H-NMR (400 MHz, CDCl₃) δ:8.31 (1H, d, J=4.3 Hz), 7.84-7.83 (2H, m), 7.71-7.68 (2H, m), 7.38 (1H, d, J=7.3 Hz), 7.05-7.03 (1H, m), 4.34-4.30 (1H, m), 3.87-3.84 (1H, m), 3.47-3.44 (1H, m), 2.85-2.70 (2H, m), 2.00-1.82 (2H, m), 1.77-1.68 (2H, m).

Reference Examples 95 to 96

According to the methods described in Reference Example 79 to Reference Example 81, the compounds of Reference Examples 95 to 96 were obtained from the corresponding compounds, respectively.

TABLE 19

| Ref. No. | Chemical Structure | Instrumental analysis data |
|---|---|---|
| 95 | (rac.) | ¹H-NMR (400 MHz, CDCl₃) δ: 7.39-7.27 (5H, m), 7.08 (1H, d, J = 8.5 Hz), 6.96 (1H, d, J = 7.9 Hz), 5.47 (1H, s), 5.09 (2H, s), 3.68-3.65 (1H, m), 3.45-3.43 (1H, m), 3.35-3.29 (1H, m), 1.20-1.18 (1H, m), 1.08-1.05 (2H, m), 0.72-0.68 (1H, m). |
| 96 | (rac.) | ¹H-NMR (400 MHz, CDCl₃) δ: 7.37-7.27 (5H, m), 7.09-7.06 (1H, m), 6.70-6.68 (1H, m), 5.49 (1H, s), 5.08 (2H, s), 3.69-3.63 (1H, m), 3.44-3.42 (1H, m), 3.32-3.26 (1H, m), 1.19-1.16 (1H, m), 1.07-1.04 (2H,m), 0.72-0.66 (1H, m). |

Reference Example 97 rac-tert-butyl [(4-chloro-6,7-dihydro-5H-cyclopenta[b]pyridin-7-yl)methyl]carbamate

[Chemical Formula 122]

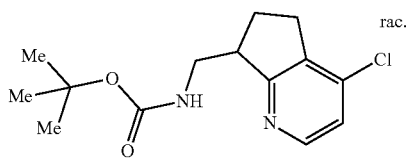

To a toluene solution (1.374 mL) of the compound (49.1 mg, 0.275 mmol) of Reference Example 98 was added 1 mol/L diisobutylaluminium hydride toluene solution (0.825 mL, 0.825 mmol) at 0° C. After stirring at room temperature for 3 hr, to the reaction mixture were added 30% aqueous potassium sodium tartrate solution, saturated aqueous sodium bicarbonate and ethyl acetate. To this mixed solution was added di-tert-butyl dicarbonate (90 mg, 0.412 mmol) at room temperature. After stirring at room temperature for 1 hr, to the reaction mixture was added water, and the mixture was subjected to extraction with ethyl acetate. The organic layer was dried over anhydrous sodium sulfate, filtered, and concentrated. The concentrated residue was separated and purified by silica gel column chromatography (hexane/ethyl acetate) to give the title compound (30.9 mg) as a pale-yellow oil.

$^1$H-NMR (400 MHz, CDCl$_3$)

δ:8.24 (1H, d, J=5.5 Hz), 7.08 (1H, d, J=5.5 Hz), 5.64 (1H, s), 3.68-3.65 (1H, m), 3.34-3.29 (2H, m), 3.01-2.97 (1H, m), 2.92-2.84 (1H, m), 2.33-2.30 (1H, m), 1.84-1.79 (1H, m), 1.43 (9H, s).

Reference Example 98 rac-4-chloro-6,7-dihydro-5H-cyclopenta[b]pyridine-7-carbonitrile

[Chemical Formula 123]

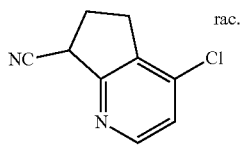

To a toluene solution (1.965 mL) of 4-chloro-6,7-dihydro-5H-cyclopenta[B]pyridin-7-ol (100 mg, 0.590 mmol) and acetone cyanohydrin (0.081 mL, 0.884 mmol) was added cyanomethylenetributylphosphorane (0.464 mL, 1.769 mmol). After stirring at 60° C. for 1 hr, to the reaction mixture was added water, the mixture was subjected to extraction with ethyl acetate, and the organic layer was dried over anhydrous sodium sulfate, filtered, and concentrated. The concentrated residue was separated and purified by silica gel column chromatography (hexane/ethyl acetate) to give the title compound (49.1 mg).

$^1$H-NMR (400 MHz, CDCl$_3$)

δ:8.33 (1H, d, J=5.5 Hz), 7.17 (1H, d, J=5.5 Hz), 4.20-4.18 (1H, m), 3.20-3.09 (1H, m), 3.00-2.94 (1H, m), 2.65-2.55 (1H, m), 2.42 (1H, ddt, J=17.0, 9.4, 3.1 Hz).

Reference Example 99 rac-tert-butyl [(4-ethoxy-6,7-dihydro-5H-cyclopenta[b]pyridin-7-yl)methyl]carbamate

[Chemical Formula 124]

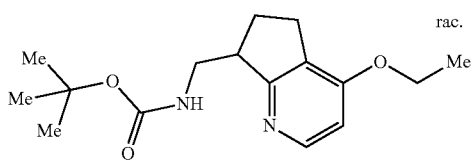

To a toluene solution (1.89 mL) of the compound (50 mg, 0.189 mmol) of Reference Example 100, ethanol (0.055 mL, 0.946 mmol) and triphenylphosphine (74.4 mg, 0284 mmol) was added bis(2-methoxyethyl) azodicarboxylate at 0° C. After stirring at room temperature for 1 hr, to the reaction mixture was added methanol, and the mixture was concentrated. The concentrated residue was separated and purified by silica gel column chromatography (hexane/ethyl acetate) to give the title compound (35 mg).

$^1$H-NMR (400 MHz, CDCl$_3$)

δ:8.23 (1H, d, J=5.5 Hz), 6.56 (1H, d, J=5.5 Hz), 5.79 (1H, s), 4.10-4.06 (2H, m), 3.67-3.65 (1H, m), 3.27-3.22 (2H, m), 2.89-2.85 (1H, m), 2.78-2.69 (1H, m), 2.28-2.25 (1H, m), 1.80-1.73 (1H, m), 1.43 (9H, s), 1.41 (3H, t, J=6.6 Hz).

Reference Example 100 rac-tert-butyl [(4-hydroxy-6,7-dihydro-5H-cyclopenta[b]pyridin-7-yl)methyl]carbamate

[Chemical Formula 125]

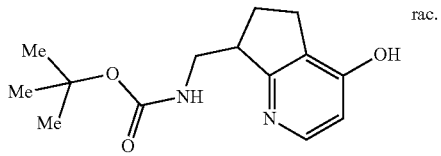

To an N-methyl-2-pyrrolidone suspension (1.46 mL) of the compound (248 mg, 0.877 mmol) of Reference Example 97 and potassium carbonate (606 mg, 4.39 mmol) was added acetohydroxamic acid (198 mg, 2.63 mmol). After stirring at 100° C. for 6 hr, the reaction mixture was filtered through Celite, and the filtrate was concentrated. The concentrated residue was separated and purified by silica gel column chromatography (chloroform/methanol) to give the title compound (128 mg).

$^1$H-NMR (400 MHz, CDCl$_3$)

δ:7.39 (1H, s), 6.32 (1H, s), 5.22 (1H, s), 4.26 (1H, s), 3.36-3.26 (3H, m), 2.87-2.83 (1H, m), 2.70-2.62 (1H, m), 2.31-2.27 (1H, m), 1.75-1.67 (1H, m), 1.42 (9H, s).

Reference Example 101 rac-2-{[4-(4-methylphenyl)-5,6,7,8-tetrahydroquinolin-8-yl]methyl}-1H-isoindole-1,3(2H)-dione

[Chemical Formula 126]

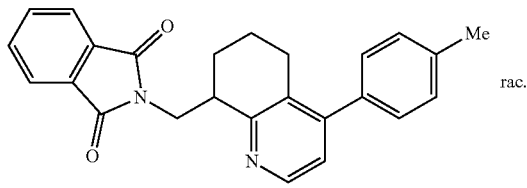

To a toluene suspension (2.3 mL) of the compound (100 mg, 0.306 mmol) of Reference Example 102, 4,5-bis(diphenylphosphino)-9,9-dimethylxanthene (53.1 mg, 0.092 mmol), 4-methylphenylboronic acid (125 mg, 0.918 mmol) and cesium carbonate (199 mg, 0.612 mmol) was added tris(dibenzylideneacetone)dipalladium(0) (56 mg, 0.061 mmol). After stirring at 130° C., to the reaction mixture was added water, the mixture was subjected to extraction with ethyl acetate, and the organic layer was dried over anhydrous sodium sulfate, filtered, and concentrated. The concentrated residue was separated and purified by silica gel column chromatography (hexane/ethyl acetate) to give the title compound (26.5 mg).

$^1$H-NMR (400 MHz, CDCl$_3$) δ:8.40 (1H, d, J=4.9 Hz), 7.86-7.84 (2H, m), 7.72-7.69 (2H, m), 7.23 (2H, d, J=4.9 Hz), 7.17 (2H, d, J=7.9 Hz), 7.05-7.04 (1H, m), 4.40-4.37 (1H, m), 4.00-3.97 (1H, m), 3.63 (1H, s), 2.66-2.61 (2H, m), 2.39 (3H, s), 1.90-1.60 (4H, m).

Reference Example 102 rac-2-[(4-chloro-5,6,7,8-tetrahydroquinolin-8-yl)methyl]-1H-isoindole-1,3(2H)-dione

[Chemical Formula 127]

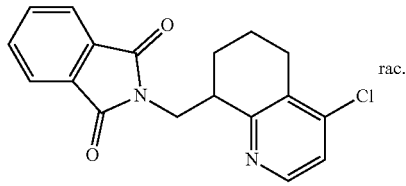

To the compound (500 mg, 1.62 mmol) of Reference Example 93 was added phosphoryl chloride (1.5 mL, 16.22 mmol) at room temperature. After stirring at 90° C. for 4 hr, to the reaction mixture was added ice water. Then, 4 mol/L sodium hydroxide was added thereto, the mixture was subjected to extraction with ethyl acetate, and the organic layer was dried over sodium sulfate, filtered, and concentrated. The concentrated residue was separated and purified by silica gel column chromatography (hexane/ethyl acetate) to give the title compound (256 mg).

$^1$H-NMR (400 MHz, CDCl$_3$) δ:8.21 (1H, d, J=4.9 Hz), 7.87-7.84 (2H, m), 7.73-7.70 (2H, m), 7.15 (1H, d, J=4.9 Hz), 4.35-4.30 (1H, m), 3.86-3.84 (1H, m), 3.49-3.46 (1H, m), 2.87-2.75 (2H, m), 2.03-2.00 (1H, m), 1.85-1.79 (3H, m).

Reference Example 103-1, Reference Example 103-2

Reference Example 103-1 rac-benzyl {[(3R,4S)-3-ethyl-3,4-dihydro-2H-pyrano[3,2-b]pyridin-4-yl]methyl}carbamate

Reference Example 103-2 rac-benzyl {[(3S,4S)-3-ethyl-3,4-dihydro-2H-pyrano[3,2-b]pyridin-4-yl]methyl}carbamate

[Chemical Formula 128]

Ref. Example 103-1

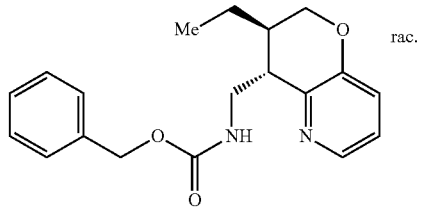

Ref. Example 103-2

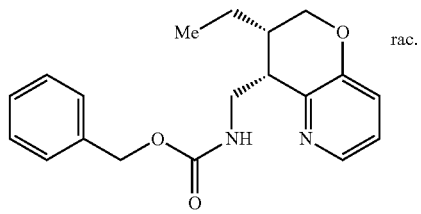

By the same methods as in Reference Example 2 to Reference Example 4, Reference Example 37 and Reference Example 38, the title compounds of Reference Example 103-1 and Reference Example 103-2 were obtained from 2-ethylpropane-1,3-diol, respectively.

Reference Example 103-1

$^1$H-NMR (400 MHz, CDCl$_3$) δ:8.02 (1H, dd, J=3.7, 1.8 Hz), 7.34-7.22 (5H, m), 7.04-6.97 (2H, m), 6.43-6.35 (1H, m), 5.04 (2H, s), 4.07-3.98 (2H, m), 3.74-3.66 (1H, m), 3.24-3.15 (1H, m), 3.11-3.04 (1H, m), 2.08-1.98 (1H, m), 1.46-1.34 (1H, m), 1.32-1.21 (1H, m), 0.96 (3H, t, J=7.3 Hz).

Reference Example 103-2

$^1$H-NMR (400 MHz, CDCl$_3$) δ:8.11 (1H, dd, J=4.3, 1.2 Hz), 7.37-7.27 (5H, m), 7.11-7.02 (2H, m), 5.92 (1H, brs), 5.09 (2H, s), 4.20 (1H, dd, J=11.0, 3.0 Hz), 3.93 (1H, dd, J=11.0, 6.1 Hz), 3.86-3.77 (1H, m), 3.42-3.33 (1H, m), 2.77-2.70 (1H, m), 1.84-1.75 (1H, m), 1.66-1.56 (1H, m), 1.44-1.32 (1H, m), 0.98 (3H, t, J=7.3 Hz).

Reference Example 104 rac-4-methyl-5,6,7,8-tetrahydroquinoline-8-carbonitrile

[Chemical Formula 129]

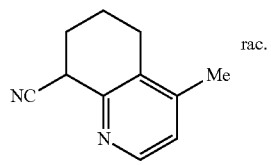

By the same method as in Reference Example 62, the title compound was obtained from the compound of Reference Example 105.

¹H-NMR (400 MHz, CDCl₃) δ:8.35 (1H, d, J=4.9 Hz), 7.04 (1H, d, J=4.9 Hz), 4.11 (1H, t, J=6.1 Hz), 2.78-2.61 (2H, m), 2.28-2.15 (2H, m), 2.24 (3H, s), 2.14-2.04 (1H, m), 1.97-1.88 (1H, m).

Reference Example 105 rac-8-bromo-4-methyl-5,6,7,8-tetrahydroquinoline

[Chemical Formula 130]

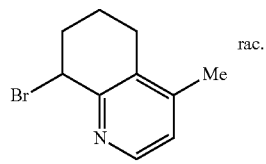

To a chloroform solution (5.3 mL) of the compound (87.0 mg, 0.530 mmol) of Reference Example 106 was added phosphorus tribromide (0.0747 mL, 0.795 mmol). After stirring at 70° C. for 2 hr, to the reaction mixture was added saturated aqueous sodium hydrogencarbonate solution (30 mL), the mixture was subjected to extraction with chloroform (30 mL×twice), and the organic layer was dried over anhydrous sodium sulfate, filtered, and concentrated to give the title compound (118 mg).

¹H-NMR (400 MHz, CDCl₃)

δ:8.34 (1H, d, J=4.9 Hz), 6.99 (1H, d, J=4.9 Hz), 5.55-5.53 (1H, m), 2.87 (1H, dd, J=17.7, 5.5 Hz), 2.70-2.61 (1H, m), 2.49-2.44 (1H, m), 2.36-2.13 (2H, m), 2.23 (3H, s), 2.04-1.96 (1H, m).

Reference Example 106 rac-4-methyl-5,6,7,8-tetrahydroquinolin-8-ol

[Chemical Formula 131]

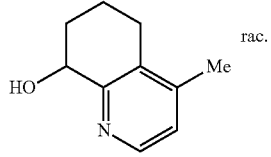

To a methanol solution (5.3 mL) of the compound (85.5 mg, 0.530 mmol) of Reference Example 107 was added sodium borohydride (30.1 mg, 0.796 mmol) under ice-cooling. After stirring at room temperature for 3 hr, to the reaction mixture was added saturated aqueous ammonium chloride solution (30 mL), the mixture was subjected to extraction with chloroform (30 mL×twice), and the organic layer was dried over anhydrous sodium sulfate, filtered, and concentrated to give the title compound (93.7 mg).

¹H-NMR (400 MHz, CDCl₃)

δ:8.28 (1H, d, J=4.9 Hz), 6.99 (1H, d, J=4.9 Hz), 4.68 (1H, dd, J=8.9, 5.2 Hz), 4.17 (1H, brs), 2.74-2.62 (2H, m), 2.33-2.26 (1H, m), 2.23 (3H, s), 2.10-2.02 (1H, m), 1.87-1.70 (2H, m).

Reference Example 107

4-methyl-6,7-dihydroquinolin-8 (5H)-one

[Chemical Formula 132]

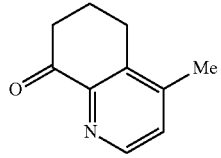

A mixture of 4-chloro-6,7-dihydroquinolin-8 (5H)-one (302 mg, 1.67 mmol), trimethylboroxin (0.756 mL, 5.45 mmol), 1,1'-bis(diphenylphosphino)ferrocene palladium(II) chloride (130 mg, 0.159 mmol), potassium carbonate (388 mg, 2.81 mmol) and dichloroethane (2.0 mL) was stirred under microwave irradiation at 120° C. for 2 hr. Then, the reaction mixture was separated and purified by silica gel column chromatography (chloroform/methanol) to give the title compound (85.5 mg).

¹H-NMR (400 MHz, CDCl₃)

δ:8.57 (1H, d, J=4.3 Hz), 7.24 (1H, d, J=4.9 Hz), 2.94 (2H, t, J=6.1 Hz), 2.79 (2H, t, J=6.7 Hz), 2.36 (3H, s), 2.24-2.18 (2H, m).

Reference Example 108-1, Reference Example 108-2

Reference Example 108-1 rac-(5R,7R)-5-methyl-6,7-dihydro-5H-cyclopenta[b]pyridine-7-carbonitrile

Reference Example 108-2 rac-(5R,7S)-5-methyl-6,7-dihydro-5H-cyclopenta[b]pyridine-7-carbonitrile

[Chemical Formula 133]

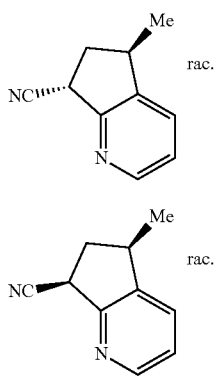

Ref. Example 108-1

Ref. Example 108-2

By the same methods as in Reference Example 104 and Reference Example 105, the title compounds were obtained as a diastereomeric mixture (1:1) of Reference Example 108-1 and Reference Example 108-2 from the compound of Reference Example 109.

$^1$H-NMR (400 MHz, CDCl$_3$) δ:8.51-8.48 (1H, m), 7.58-7.54 (1H, m), 7.25-7.22 (1H, m), 4.23-4.12 (1H, m), 3.54-3.21 (1H, m), 2.87-2.65 (1H, m), 2.17-1.96 (1H, m), 1.41-1.31 (3H, m).

Reference Example 109-1, Reference Example 109-2

Reference Example 109-1 rac-(5R,7R)-5-methyl-6,7-dihydro-5H-cyclopenta[b]pyridin-7-ol

Reference Example 109-2 rac-(5R,7S)-5-methyl-6,7-dihydro-5H-cyclopenta[b]pyridin-7-ol

[Chemical Formula 134]

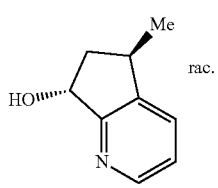

Ref. Example 109-1

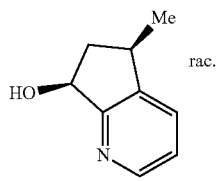

Ref. Example 109-2

To a chloroform solution (2.0 mL) of the compound (232 mg, 1.55 mmol) of Reference Example 110 was added trifluoroacetic anhydride (3.0 mL, 21.4 mmol) under ice-cooling. After stirring at room temperature for 20 hr, to the reaction mixture was added 1 mol/L aqueous sodium hydroxide solution (30 mL), the mixture was subjected to extraction with chloroform (30 mL×twice), and the organic layer was dried over anhydrous sodium sulfate, filtered, and concentrated to give the title compounds (125 mg) as a diastereomeric mixture (1:1) of Reference Example 109-1 and Reference Example 109-2.

$^1$H-NMR (400 MHz, CDCl$_3$) δ:8.50-8.38 (1H, m), 7.61-7.47 (1H, m), 7.22-7.14 (1H, m), 5.32-5.11 (1H, m), 3.58-3.38 (0.5H, m), 3.14-3.01 (1H, m), 2.89-2.72 (1H, m), 2.42-2.27 (0.5H, m), 2.11-1.97 (0.5H, m), 1.70-1.53 (0.5H, m), 1.44-1.18 (3H, m).

Reference Example 110 rac-5-methyl-1-oxo-6,7-dihydro-5H-1λ$^5$-cyclopenta[b]pyridine

[Chemical Formula 135]

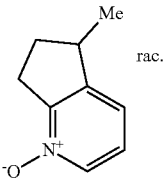

By the same method as in Reference Example 93, the title compound was obtained from 5-methyl-6,7-dihydro-5H-cyclopenta[b]pyridine.

$^1$H-NMR (400 MHz, CDCl$_3$) δ:8.06 (1H, d, J=6.1 Hz), 7.12-7.07 (2H, m), 3.36-3.18 (2H, m), 3.10-3.01 (1H, m), 2.47-2.37 (1H, m), 1.77-1.68 (1H, m), 1.31 (3H, d, J=6.7 Hz).

Reference Example 111-1, Reference Example 111-2

Reference Example 111-1 rac-tert-butyl {[(5R,8S)-5-methyl-5,6,7,8-tetrahydroquinolin-8-yl]methyl}carbamate

Reference Example 111-2 rac-tert-butyl {[(5R,8R)-5-methyl-5,6,7,8-tetrahydroquinolin-8-yl]methyl}carbamate

[Chemical Formula 136]

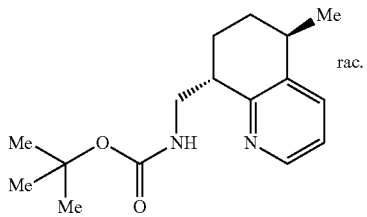

Ref. Example 111-1

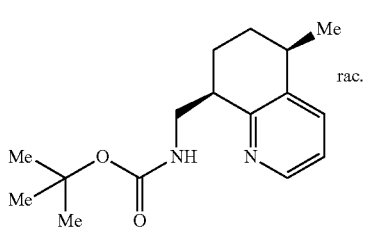

Ref. Example 111-2

By the same method as in Reference Example 61, the title compounds were obtained as a diastereomeric mixture of Reference Example 111-1 and Reference Example 111-2 from the compound of Reference Example 112.

$^1$H-NMR (400 MHz, CDCl$_3$) δ:8.39-8.36 (1H, m), 7.53-7.46 (1H, m), 7.09 (1H, dd, J=7.6, 4.6 Hz), 5.87 (1H, brs), 3.71-3.57 (1H, m), 3.38-3.27 (1H, m), 2.98-2.85 (2H, m), 2.10-1.87 (2H, m), 1.67-1.59 (2H, m), 1.45 (9H, s), 1.28-1.26 (3H, m).

Reference Example 112-1, Reference Example 112-2

Reference Example 112-1 rac-(5R,8R)-5-methyl-5,6,7,8-tetrahydroquinoline-8-carbonitrile

Reference Example 112-2 rac-(5R,8S)-5-methyl-5,6,7,8-tetrahydroquinoline-8-carbonitrile

[Chemical Formula 137]

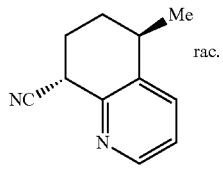

Ref. Example 112-1

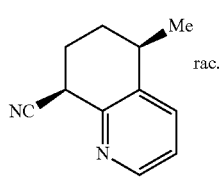

Ref. Example 112-2

By the same methods as in Reference Example 104, Reference Example 105, Reference Example 109 and Reference Example 110, the title compounds were obtained as a diastereomeric mixture of Reference Example 112-1 and Reference Example 112-2 from 5-methyl-5,6,7,8-tetrahydroquinoline.

$^1$H-NMR (400 MHz, CDCl$_3$) δ:8.48-8.47 (1H, m), 7.60-7.57 (1H, m), 7.22 (1H, dd, J=7.9, 4.9 Hz), 4.13-4.07 (1H, m), 3.06-2.89 (1H, m), 2.40-2.28 (1H, m), 2.23-1.55 (3H, m), 1.35-1.29 (3H, m).

Reference Examples 113 to 114

According to the methods described in Reference Example 5 and Reference Example 55, the compounds of Reference Examples 113 and 114 were obtained from the corresponding compounds of Examples, respectively.

TABLE 20

| Ref.No. | Chemical Structure | Instrumental analysis data |
|---|---|---|
| 113 | 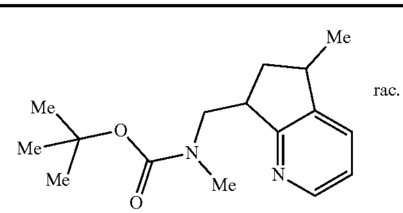 | $^1$H-NMR (400 MHz, CDCl$_3$) δ: 8.38 (1H, d, J = 4.9 Hz), 7.45 (1H, d, J = 7.3 Hz), 7.08 (1H, dd, J = 7.3, 4.9 Hz), 3.88-3.84 (1H, m), 3.62 (1H, m), 3.42-3.34 (1H, m), 3.18-3.08 (1H, m), 2.90 (3H, s), 2.55-2.48 (1H, m), 1.51-1.44 (1H, m), 1.47 (9H, s), 1.34 (3H, d, J = 7.3 Hz). |

| Ref.No. | Chemical Structure | Instrumental analysis data |
|---|---|---|
| 114 | 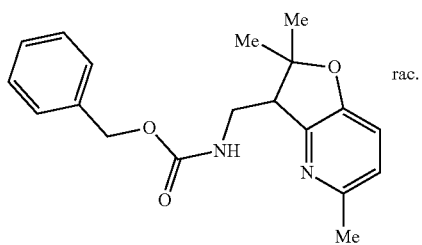 rac. | $^1$H-NMR (400 MHz, CDCl$_3$) δ: 6.89 (2H, d, J = 7.9 Hz), 4.07-3.98 (1H, m), 3.01-2.97 (1H, m), 2.84 (3H, s), 2.47-2.43 (1H, m), 1.46 (3 H, s), 1.40 (6H, s), 1.20 (9H, s). |

Reference Example 115 rac-benzyl [(2,2,5-trimethyl-2,3-dihydrofuro[3,2-b]pyridin-3-yl)methyl]carbamate

[Chemical Formula 138]

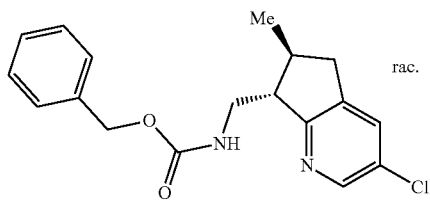

By the same methods as in Reference Example 30 to Reference Example 32, Reference Example 37 and Reference Example 38, the title compound was obtained from 2-bromo-6-methylpyridin-3-ol and ethyl 2-bromo-2-methylpropanoate.

$^1$H-NMR (400 MHz, CDCl$_3$) δ:7.41-7.28 (5H, m), 6.90 (2H, s), 6.39-6.37 (1H, m), 5.14 (2H, s), 3.85-3.81 (1H, m), 3.27-3.24 (1H, m), 3.18-3.16 (1H, m), 2.45 (3H, s), 1.52 (3H, s), 1.37 (3H, s).

Reference Example 116 rac-benzyl {[(6S,7S)-3-chloro-6-methyl-6,7-dihydro-5H-cyclopenta[b]pyridin-7-yl]methyl}carbamate

[Chemical Formula 139]

By the same methods as in Reference Example 30, Reference Example 37 and Reference Example 38, the title compound was obtained from the compound of Reference Example 117.

$^1$H-NMR (400 MHz, CDCl$_3$) δ:8.26 (1H, s), 7.44 (1H, s), 7.38-7.29 (5H, m), 6.07 (1H, brs), 5.11 (2H, s), 3.88-3.81 (1H, m), 3.34-3.28 (1H, m), 3.03-2.99 (1H, m), 2.83-2.80 (1H, m), 2.56-2.49 (1H, m), 2.30-2.18 (1H, m), 1.26 (3H, d, J=7.3 Hz).

Reference Example 117 rac-3-(2-bromo-5-chloropyridin-3-yl)-2-methylpropan-1-ol

[Chemical Formula 140]

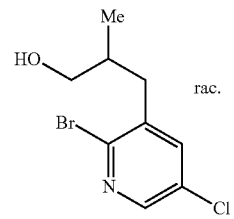

To a mixture of 2-bromo-5-chloronicotinaldehyde (999 mg, 4.30 mmol) and toluene (11 mL) was added ethyl 2-(triphenylphosphoranylidene)propionate (1.64 g, 4.52 mmol) under ice-cooling. After stirring at 90° C. for 3 hr, the reaction mixture was concentrated. The concentrated residue was separated and purified by silica gel column chromatography (hexane/ethyl acetate).

To a mixture of the obtained purified product (1.29 g) and tetrahydrofuran (42.5 mL) was added dropwise 4 mol/L lithium borohydride tetrahydrofuran solution (1.28 mL, 5.10 mmol) over 5 min under ice-cooling. After stirring at room temperature for 15 min, the mixture was stirred at 60° C. for 2 hr, and methanol (5 mL) and 1 mol/L hydrochloric acid (10 mL) were added thereto under ice-cooling. The mixture was subjected to extraction with ethyl acetate (20 mL×three times), and the organic layer was dried over anhydrous sodium sulfate, filtered, and concentrated. The concentrated residue was separated and purified by amino silica gel column chromatography (hexane/ethyl acetate) to give the title compound (469 mg).

$^1$H-NMR (400 MHz, CDCl$_3$)

δ:8.21 (1H, d, J=2.4 Hz), 7.51 (1H, d, J=3.0 Hz), 4.25 (1H, brs), 3.56-3.55 (2H, m), 2.94-2.90 (1H, m), 2.53-2.49 (1H, m), 2.14-2.09 (1H, m), 0.98 (3H, d, J=22.5 Hz).

Reference Example 118 rac-benzyl [(5-fluoro-2,2-dimethyl-2,3-dihydrofuro[3,2-b]pyridin-3-yl)methyl]carbamate

[Chemical Formula 141]

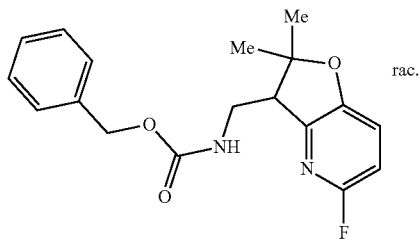

By the same methods as in Reference Example 30 to Reference Example 32, Reference Example 37 and Reference Example 38, the title compound was obtained from 2-bromo-6-fluoropyridin-3-ol and ethyl 2-bromo-2-methyl-propanoate.

$^1$H-NMR (400 MHz, CDCl$_3$) δ:7.40-7.29 (5H, m), 7.08-7.06 (1H, m), 6.69-6.67 (1H, m), 5.87-5.85 (1H, brm), 5.17-5.09 (2H, m), 3.83-3.79 (1H, m), 3.31-3.25 (1H, m), 3.22-3.20 (1H, m), 1.54 (3H, s), 1.38 (3H, s).

Test Example 1: Evaluation of Agonist Activity on Human TAAR1 Receptor

TAAR1 is a G protein-coupled receptor that binds to G proteins (Gas), and activation of the TAAR1 receptor by agonists induces an increase in intracellular cAMP levels. Therefore, the agonist activity of the sample on the human TAAR1 receptor was evaluated using the cAMP assay method.

cAMP Hunter™ CHO-K1 TAAR1 Gs Cell Line, a cell expressing human TAAR1 receptor, was purchased. Human TAAR1-expressing CHO cells were seeded in a 96-well plate, and after culturing for 24 hours, a sample dissolved in DMSO was added and incubated at 37° C. for 30 minutes. A sample for cAMP measurement was prepared according to the cAMPHiRange kit protocol. The amount of cAMP produced by the sample was measured by time-resolved fluorescence using EnVision (excitation wavelength: 330 nm, fluorescence wavelength 620 mm/665 nm).

Sample %=100×{(Csamp)−(Cblank)}/{(Ctyramine)−(Cblank)}

Csamp: count of sample, Ctyramine: count of 100 μM tyramine, Cblank: count of blank

TABLE 21

| | TAAR1 agonist activity at each concentration (%) | | |
|---|---|---|---|
| Example | 100 nM | 1000 nM | 10000 nM |
| 1 | 2 | 18 | 54 |
| 2 | 7 | 37 | 75 |
| 3 | 0 | 1 | 9 |
| 4 | 17 | 55 | 67 |
| 5 | 24 | 68 | 90 |
| 6 | 16 | 57 | 75 |
| 7 | 17 | 56 | 75 |
| 8 | 24 | 63 | 75 |
| 9 | 15 | 53 | 70 |
| 10 | 18 | 66 | 91 |
| 11 | 20 | 58 | 79 |
| 12 | 21 | 58 | 75 |
| 13 | 4 | 31 | 63 |
| 14 | 10 | 47 | 74 |
| 15 | 24 | 67 | 90 |
| 16 | 6 | 37 | 76 |
| 17 | 0 | 4 | 25 |
| 18 | 29 | 73 | 87 |
| 19 | 2 | 13 | 51 |
| 20 | 33 | 88 | 107 |
| 21 | 0 | 23 | 81 |
| 22 | 11 | 56 | 84 |
| 23 | 35 | 74 | 91 |
| 24 | 25 | 71 | 101 |
| 25 | 2 | 21 | 63 |
| 26 | 0 | 25 | 73 |
| 27 | 40 | 81 | 95 |
| 28 | 7 | 38 | 71 |
| 29 | 51 | 93 | 104 |
| 30 | 2 | 18 | 63 |
| 31 | 1 | 3 | 12 |
| 32 | 1 | 4 | 22 |
| 33 | 4 | 22 | 52 |
| 34 | 10 | 48 | 83 |
| 35 | 57 | 82 | 87 |
| 36 | 0 | 20 | 67 |
| 37 | 13 | 49 | 72 |
| 38 | 52 | 86 | 93 |
| 39 | 1 | 12 | 48 |
| 40 | 25 | 57 | 68 |
| 41 | 12 | 38 | 65 |
| 42 | 25 | 70 | 90 |
| 43 | 0 | 0 | 7 |
| 44 | 13 | 48 | 79 |
| 45 | 13 | 51 | 77 |
| 46 | 31 | 70 | 80 |
| 47 | 13 | 52 | 84 |
| 48 | 38 | 74 | 86 |
| 49 | 25 | 63 | 75 |
| 50 | 12 | 45 | 63 |
| 51 | 10 | 46 | 77 |
| 52 | 1 | 8 | 48 |
| 53 | 0 | 3 | 18 |
| 54 | 15 | 63 | 94 |
| 55 | 31 | 75 | 87 |
| 56 | 23 | 67 | 82 |
| 57 | 32 | 72 | 79 |
| 58 | 36 | 74 | 82 |
| 59 | 19 | 65 | 84 |
| 60 | 7 | 40 | 82 |
| 61 | 2 | 22 | 66 |
| 62 | 2 | 20 | 66 |
| 63 | 3 | 22 | 62 |
| 64 | 0 | 7 | 40 |
| 65 | 0 | 28 | 67 |
| 66 | 21 | 66 | 82 |
| 67 | 1 | 10 | 39 |
| 68 | 3 | 23 | 68 |
| 69 | 4 | 30 | 62 |
| 70 | 0 | 23 | 57 |
| 71 | 0 | 6 | 29 |
| 72 | 0 | 4 | 23 |
| 73 | 0 | 9 | 40 |
| 74 | 7 | 46 | 92 |
| 75 | 0 | 26 | 75 |
| 76 | 0 | 6 | 33 |
| 77 | 0 | 11 | 47 |
| 78 | 0 | 5 | 27 |
| 79 | 36 | 77 | 90 |
| 80 | 17 | 48 | 62 |
| 81 | 48 | 86 | 95 |
| 82 | 51 | 92 | 101 |
| 83 | 59 | 91 | 99 |
| 84 | 15 | 51 | 79 |
| 85 | 6 | 37 | 70 |

TABLE 21-continued

| | TAAR1 agonist activity at each concentration (%) | | |
|---|---|---|---|
| Example | 100 nM | 1000 nM | 10000 nM |
| 86 | 1 | 8 | 40 |
| 87 | 4 | 25 | 63 |
| 88 | 11 | 38 | 65 |
| 89 | 0 | 23 | 48 |
| 90 | 54 | 85 | 94 |
| 91 | 0 | 14 | 49 |
| 92 | 0 | 0 | 0 |
| 93 | 0 | 12 | 45 |
| 94 | 1 | 4 | 28 |
| 95 | 59 | 90 | 96 |
| 96 | 3 | 28 | 66 |
| 97 | 70 | 101 | 96 |
| 98 | 1 | 9 | 37 |
| 99 | 9 | 39 | 62 |
| 100 | 0 | 17 | 50 |
| 101 | 62 | 79 | 84 |
| 102 | 1 | 18 | 59 |
| 103 | 60 | 84 | 89 |
| 104 | 0 | 5 | 31 |
| 105 | 64 | 77 | 79 |
| 106 | 38 | 70 | 78 |

Test Example 2-1: Phencyclidine-Induced Hyperlocomotion Suppression Test

Eight-week-old C57BL/6J male mice were used. A 0.5% methylcellulose solution was used as a solvent to prepare a solution for administration of the sample, and used in turbid condition, and for preparation of an administration solution for phencyclidine, physiological saline was used as a solvent and used after dissolution.

The phencyclidine-induced hyperlocomotion suppression is test was conducted as follows using Muromachi Kikai Co., Ltd.'s Supermex, the data acquisition program CompACT AMS, and a transparent plastic cage.

The animal was placed in the cage described above, and locomotion measurement was started. Thirty minutes later, the mouse was gently removed, a compound administration solution (vehicle or sample suspension) was orally administered, and the mouse was returned to its cage. Thirty minutes after administration, Phencyclidine administration solution or physiological saline solution was administered subcutaneously. After both administrations, the mouse was immediately returned to the locomotor activity measurement cage for each channel, and locomotor activity measurement was continued. The amount of exercise was measured for 120 minutes from the start of the measurement with a measurement interval of 5 minutes. The data for 90 minutes from 30 minutes to 120 minutes after the start of exercise measurement was used as the test results, and the exercise amount of each individual for 90 minutes was totaled.

Parametric Dunnett-type multiple comparisons (significance level: 5% on both sides) were performed between the sample administration group and the vehicle administration group. If the sample administration group showed significant inhibition of locomotor activity compared to the vehicle administration group, it was judged to have antipsychotic effects.

The results of the above test using the compound of Example 27 are shown in FIG. 1.

Test Example 2-2: Phencyclidine-Induced Hyperlocomotion Suppression Test

Eight-week-old C57BL/6J male mice were used. Physiological saline was used as a solvent to prepare the sample administration solution, and used in turbid condition, and physiological saline was used as the solvent to prepare the phencyclidine administration solution, and dissolution was attained before use.

The phencyclidine-induced hyperlocomotion suppression test was conducted as follows using an activity meter equipped with a photo assembly and an electric counter.

Mice to which a compound administration solution (vehicle or sample suspension) was subcutaneously administered were placed in the above-mentioned apparatus, and locomotion measurement was started. Thirty minutes after the start of the measurement, the mice were gently removed and Phencyclidine administration solution or physiological saline was administered subcutaneously. After administration, the mouse was immediately returned to the device, and locomotor activity measurement continued for 60 minutes. The measurement interval for exercise measurement was 5 minutes. Data for 60 minutes from 30 minutes to 90 minutes after the start of exercise measurement was used as the test result, and the exercise amount of each individual over the 60 minutes was totaled.

Parametric Dunnett-type multiple comparisons (significance level: 5% on both sides) were performed between the sample administration group and the vehicle administration group. If the sample administration group showed significant inhibition of locomotor activity compared to the vehicle administration group, it was judged to have antipsychotic effects.

The results of the above tests using the compounds of Example 8 and Example 49 are shown in FIGS. 2 and 3.

Test Example 3: Evaluation of hERG Channel Inhibitory Activity

The hERG channel inhibitory effect of the disclosed compounds was measured by a whole-cell patch clamp method using an autopatch clamp system using CHO cells wherein hERG channels involved in human rapidly activated delayed rectifier potassium current ($I_{Kr}$) were forcibly expressed.

(Preparation of Cell Suspension)

hERG-CHO cells purchased from ChanTest were cultured at 37° C. in a $CO_2$ incubator, and immediately before hERG current measurement, they were detached from the flask using trypsin to prepare a cell suspension.

(Solution Preparation)

Extracellular fluid and intracellular fluid used for measurement were prepared as follows.

Extracellular fluid: 2 mmol/L $CaCl_2$, 1 mmol/L $MgCl_2$, 10 mmol/L HEPES, 4 mmol/L KCl, 145 mmol/L NaCl, 10 mmol/L glucose Intracellular fluid: 10 mmol/L HEPES, 10 mmol/L EGTA, 20 mmol/L KCl, 130 mmol/L KF Sample solution: A sample solution was prepared by dissolving the sample in DMSO to a concentration of 2 mmol/L or mmol/L. Furthermore, the sample solution was diluted 200 times with extracellular fluid, and serially diluted with the extracellular fluid to prepare sample solutions at various concentrations necessary for calculating the hERG inhibition $IC_{50}$ value, and then applied.

(Current Value Measurement and Data Analysis)

A cell suspension, an extracellular solution, an intracellular solution, and a measurement plate were installed in an autopatch clamp system, and hERG current measurement was performed using the whole cell patch clamp method. The voltage protocol was such that the holding potential was −80 mV, a depolarizing pulse was applied at from −50 mV to +20 mV for 5 seconds, and then a repolarizing pulse was applied at −50 mV for 5 seconds to return to the holding potential. The interval between each pulse was 15 seconds. For data analysis, analysis software for Qube (Sophion: provided by Sophion Bioscience) was used. Four concentrations of each sample were applied incrementally, and the average value of the maximum outward current (Peaktail current) obtained in the final three stimulations of each applied concentration was used as evaluation data. In addition, the $IC_{30}$ value was calculated from the current inhibition rate at each concentration of each sample relative to the value before application using the software according to Hill equation.

The results are shown in the table below.

TABLE 22

| Example | hERG inhibition $IC_{50}$ (μmol/L) |
|---|---|
| 2 | >100 |
| 5 | >100 |
| 6 | >100 |
| 7 | >100 |
| 8 | >100 |
| 9 | >100 |
| 11 | >100 |
| 12 | >100 |
| 14 | >100 |
| 15 | >100 |
| 16 | 68.6 |
| 18 | >100 |
| 22 | >100 |
| 23 | >100 |
| 24 | 6.9 |
| 25 | 5.8 |
| 27 | >100 |
| 29 | >100 |
| 34 | >100 |
| 35 | >100 |
| 37 | >100 |
| 38 | >100 |
| 40 | >100 |
| 41 | >100 |
| 42 | >100 |
| 44 | >100 |
| 45 | >100 |
| 46 | >100 |
| 47 | >100 |
| 48 | >100 |
| 49 | >100 |
| 50 | >100 |
| 51 | >100 |
| 58 | >100 |
| 79 | >100 |
| 83 | >100 |
| 84 | >100 |
| 88 | >100 |
| 90 | 71.8 |
| 97 | >100 |

Test Example 4: Evaluation of Binding Activity to Side Effect-Related Receptors

The binding affinity of the disclosed compound to receptors associated with side effects (e.g., dopamine D2 receptors and adrenergic α1A receptors) can be measured by the following method.

A binding evaluation test is performed as follows using a CHO cell membrane fraction expressing a human type target receptor. After mixing the sample dissolved in dimethyl sulfoxide (DMSO), various receptor membrane specimens diluted with a buffer solution, and [$^3$H]-labeled ligands that have strong binding activity to each target receptor, and incubating each at room temperature, these were immediately added onto a glass fiber filter plate (Multiscreen FB, produced by Millipore) and filtered under reduced pressure. The radioactivity remaining on the filter is measured using a liquid scintillation counter (produced by PerkinElmer). The rate of inhibiting binding is calculated using the following formula. To calculate the amount of nonspecific binding to the receptor membrane specimen, a control compound that has strong binding activity to the target receptor is used instead of the sample.

Rate of inhibiting binding to target receptor (%)=100−100×{(amount of [$^3$H]-labeled ligand bound in the presence of sample)}−(amount of [$^3$H]-labeled ligand bound in the presence of 10 μmol/L control compound))}/{(amount of [$^3$H]-labeled ligand bound in the absence of sample)}−(amount of [$^3$H]-labeled ligand bound in the presence of 10 μmol/L control compound)}

(Note)

As described above, although the present disclosure has been illustrated using the preferable embodiments thereof, it is understood that the scope of the present disclosure should be interpreted only by the claims. This application claims priority to Japanese Patent Application No. 2021-66825 (filed on Apr. 10, 2021) and Japanese Patent Application No. 2021-150394 (filed on Sep. 15, 2021), and their contents are incorporated herein by reference in their entirety. It is understood that the patents, patent applications, scientific literature, and other documents cited herein should be incorporated by reference into this specification to the same extent as if the contents themselves were specifically set forth herein.

The disclosed compounds have agonist activity on the trace amine-associated receptor TAAR1 receptor, and are therefore effective in treating psychiatric disorders. The disclosed compounds are also effective on central nervous system diseases.

The invention claimed is:

1. A compound selected from the group consisting of:
1-[(2R,3S)-6-fluoro-2-methyl-2,3-dihydrofuro[3,2-b]pyridin-3-yl]methanamine;
1-[(2R,3S)-2-methyl-2,3-dihydrofuro[3,2-b]pyridin-3-yl]methanamine;
N-methyl-1-[(2R,3S)-2-methyl-2,3-dihydrofuro[3,2-b]pyridin-3-yl]methanamine;
1-[(2R,3S)-6-fluoro-2-methyl-2,3-dihydrofuro[3,2-b]pyridin-3-yl]-N-methylmethanamine; and
1-[(2R,3S)-6-fluoro-2-methyl-2,3-dihydrofuro[3,2-b]pyridin-3-yl]-N-(2H3)methylmethanamine,
or a pharmaceutically acceptable salt thereof.

2. The compound or a pharmaceutically acceptable salt thereof according to claim 1, wherein the compound is 1-[(2R,3S)-6-fluoro-2-methyl-2,3-dihydrofuro[3,2-b]pyridin-3-yl]methanamine.

3. The compound or a pharmaceutically acceptable salt thereof according to claim 1, wherein the compound is 1-[(2R,3S)-2-methyl-2,3-dihydrofuro[3,2-b]pyridin-3-yl]methanamine.

4. The compound or a pharmaceutically acceptable salt thereof according to claim 1, wherein the compound is N-methyl-1-[(2R,3S)-2-methyl-2,3-dihydrofuro[3,2-b]pyridin-3-yl]methanamine.

5. The compound or a pharmaceutically acceptable salt thereof according to claim 1, wherein the compound is 1-[(2R,3S)-6-fluoro-2-methyl-2,3-dihydrofuro[3,2-b]pyridin-3-yl]-N-methylmethanamine.

6. The compound or a pharmaceutically acceptable salt thereof according to claim 1, wherein the compound is 1-[(2R,3S)-6-fluoro-2-methyl-2,3-dihydrofuro[3,2-b]pyridin-3-yl]-N-(2H3)methylmethanamine.

7. A pharmaceutical composition, comprising:
    a compound or a pharmaceutically acceptable salt thereof; and
    a pharmaceutically acceptable excipient or additive, wherein the compound is selected from the group consisting of:
    1-[(2R,3S)-6-fluoro-2-methyl-2,3-dihydrofuro[3,2-b]pyridin-3-yl]methanamine;
    1-[(2R,3S)-2-methyl-2,3-dihydrofuro[3,2-b]pyridin-3-yl]methanamine;
    N-methyl-1-[(2R,3S)-2-methyl-2,3-dihydrofuro[3,2-b]pyridin-3-yl]methanamine;
    1-[(2R,3S)-6-fluoro-2-methyl-2,3-dihydrofuro[3,2-b]pyridin-3-yl]-N-methylmethanamine; and
    1-[(2R,3S)-6-fluoro-2-methyl-2,3-dihydrofuro[3,2-b]pyridin-3-yl]-N-(2H3)methylmethanamine.

8. The pharmaceutical composition according to claim 7, wherein the compound is 1-[(2R,3S)-6-fluoro-2-methyl-2,3-dihydrofuro[3,2-b]pyridin-3-yl]methanamine.

9. The pharmaceutical composition according to claim 7, wherein the compound is 1-[(2R,3S)-2-methyl-2,3-dihydrofuro[3,2-b]pyridin-3-yl]methanamine.

10. The pharmaceutical composition according to claim 7, wherein the compound is N-methyl-1-[(2R,3S)-2-methyl-2,3-dihydrofuro[3,2-b]pyridin-3-yl]methanamine.

11. The pharmaceutical composition according to claim 7, wherein the compound is 1-[(2R,3S)-6-fluoro-2-methyl-2,3-dihydrofuro[3,2-b]pyridin-3-yl]-N-methylmethanamine.

12. The pharmaceutical composition according to claim 7, wherein the compound is 1-[(2R,3S)-6-fluoro-2-methyl-2,3-dihydrofuro[3,2-b]pyridin-3-yl]-N-(2H3)methylmethanamine.

13. A method for treating a neurological or psychiatric disorder in a subject, comprising:
    administering to the subject a therapeutically effective amount of the compound of claim 1 or a pharmaceutically acceptable salt thereof,
    wherein the neurological or psychiatric disorder is depression, bipolar disorder, schizophrenia, obsessive-compulsive disorder, addiction, social disorder, attention deficit/hyperactivity disorder, anxiety disorder, movement disorder, epilepsy, autism, cognitive dysfunction, psychosis in Alzheimer's disease/Parkinson's disease, irritation/aggression of Parkinson's disease, mood disorders, irritation, agitation, or aggression associated with Alzheimer's disease or hyperphagia.

14. The method according to claim 13, wherein the compound is 1-[(2R,3S)-6-fluoro-2-methyl-2,3-dihydrofuro[3,2-b]pyridin-3-yl]methanamine.

15. The method according to claim 13, wherein the compound is 1-[(2R,3S)-2-methyl-2,3-dihydrofuro[3,2-b]pyridin-3-yl]methanamine.

16. The method according to claim 13, wherein the compound is N-methyl-1-[(2R,3S)-2-methyl-2,3-dihydrofuro[3,2-b]pyridin-3-yl]methanamine.

17. The method according to claim 13, wherein the compound is 1-[(2R,3S)-6-fluoro-2-methyl-2,3-dihydrofuro[3,2-b]pyridin-3-yl]-N-methylmethanamine.

18. The method according to claim 13, wherein the compound is 1-[(2R,3S)-6-fluoro-2-methyl-2,3-dihydrofuro[3,2-b]pyridin-3-yl]-N-(2H3)methylmethanamine.

19. The method according to claim 13, wherein the neurological or psychiatric disorder is depression, schizophrenia, obsessive-compulsive disorder, anxiety disorder, psychosis in Alzheimer's disease/Parkinson's disease, mood disorders, or irritation, agitation, or aggression associated with Alzheimer's disease.

20. The method according to claim 19, wherein the compound is 1-[(2R,3S)-6-fluoro-2-methyl-2,3-dihydrofuro[3,2-b]pyridin-3-yl]methanamine.

21. The method according to claim 19, wherein the compound is 1-[(2R,3S)-2-methyl-2,3-dihydrofuro[3,2-b]pyridin-3-yl]methanamine.

22. The method according to claim 19, wherein the compound is N-methyl-1-[(2R,3S)-2-methyl-2,3-dihydrofuro[3,2-b]pyridin-3-yl]methanamine.

23. The method according to claim 19, wherein the compound is 1-[(2R,3S)-6-fluoro-2-methyl-2,3-dihydrofuro[3,2-b]pyridin-3-yl]-N-methylmethanamine.

24. The method according to claim 19, wherein the compound is 1-[(2R,3S)-6-fluoro-2-methyl-2,3-dihydrofuro[3,2-b]pyridin-3-yl]-N-(2H3)methylmethanamine.

25. The method according to claim 13, wherein the neurological or psychiatric disorder is depression, schizophrenia, psychosis in Alzheimer's disease, or irritation, agitation, or aggression associated with Alzheimer's disease.

* * * * *